US009594239B1

(12) United States Patent
Ludwig et al.

(10) Patent No.: US 9,594,239 B1
(45) Date of Patent: *Mar. 14, 2017

(54) OPTICAL TOMOGRAPHY FOR MICROSCOPY, CELL CYTOMETRY, MICROPLATE ARRAY INSTRUMENTATION, CRYSTALLOGRAPHY, AND OTHER APPLICATIONS

(71) Applicant: Lester F. Ludwig, Belmont, CA (US)

(72) Inventors: Lester F. Ludwig, Belmont, CA (US); Karen Hao, Arlington, MA (US); Frank Hu, San Francisco, CA (US); Alice Huang, Belle Mead, NJ (US); Pooncharas Tipgunlakant, San Francisco, CA (US)

(73) Assignee: Lester F. Ludwig, San Antonio, TX (US)

( * ) Notice: Subject to any disclaimer, the term of this patent is extended or adjusted under 35 U.S.C. 154(b) by 602 days.

This patent is subject to a terminal disclaimer.

(21) Appl. No.: 13/963,917

(22) Filed: Aug. 9, 2013

Related U.S. Application Data

(63) Continuation-in-part of application No. 12/817,107, filed on Jun. 16, 2010, now Pat. No. 8,885,035.

(60) Provisional application No. 61/268,900, filed on Jun. 16, 2009.

(51) Int. Cl.
*H04N 7/18* (2006.01)
*G02B 21/06* (2006.01)

(52) U.S. Cl.
CPC .................................. *G02B 21/06* (2013.01)

(58) Field of Classification Search
None
See application file for complete search history.

(56) References Cited

U.S. PATENT DOCUMENTS 7,068,361 B2 *  6/2006  Cimino ................. A61L 2/0011
                                                            356/213
7,829,968 B2 * 11/2010  Yun .................... H01L 27/14627
                                                            257/436
8,885,035 B2 * 11/2014  Ludwig ............... G01N 15/1475
                                                            348/79

(Continued)

*Primary Examiner* — Gims Philippe
*Assistant Examiner* — Dakshesh Parikh
(74) *Attorney, Agent, or Firm* — Procopio, Cory, Hargreaves & Savitch LLP

(57) ABSTRACT

An electronic imaging flow-microscope for remote environmental sensing, bioreactor process monitoring, and optical microscopic tomography applications is described. A fluid conduit has a port on each end of a thin flat transparent fluid transport region. A planar illumination surface contacts one flat side of the transparent fluid transport region and a planar image sensing surface contacts the other flat side. Light from the illumination surface travels through the transparent fluid transport region to the planar image sensing surface, producing a light field affected by the fluid and objects present. The planar image sensing surface creates electrical image signals responsive to the light field. The planar illumination surface can be light emitting elements such as LEDs, OLEDs, or OLET. whose illumination can be sequenced in an image formation process. The flow microscope can further comprise flow-restricting valves, pumps, energy harvesting arrangements, and power management.

20 Claims, 64 Drawing Sheets

(56) References Cited

U.S. PATENT DOCUMENTS

| | | | |
|---|---|---|---|
| 2002/0039183 A1* | 4/2002 | Yagita | G01N 21/9027 356/240.1 |
| 2003/0165398 A1* | 9/2003 | Waldo | A61L 2/0011 422/22 |
| 2008/0054389 A1* | 3/2008 | Yun | H01L 27/14627 257/432 |
| 2012/0127298 A1* | 5/2012 | Sieracki | G01N 21/05 348/79 |

* cited by examiner

| | pixels / sq.mm | mm/px | μm/px | # pixels | Amoeba - 700μm | Amoeba - 1000μm | sensor area size (sq.mm) |
|---|---|---|---|---|---|---|---|
| Andanta Ultra-High Res CCD | 4933 | 0.00020272 | 0.2027164 | 111000000 | 3453.1 | 4933 | 22500 |
| Megaplus ER 11000 (lower) | 12732 | 7.8542E-05 | 0.07854226 | 11000000 | 8912.4 | 12732 | 864 |
| Megaplus ER 11000 (upper) | 111111 | 9E-06 | 0.00900001 | 96000000 | 77777.7 | 111111 | 864 |
| Kodak KAI-11002 | 12458 | 8.027E-05 | 0.08026971 | 11100000 | 8720.6 | 12458 | 891 |
| DCU 223 M/C Sony | 10971 | 9.1149E-05 | 0.09114939 | 786432 | 7679.7 | 10971 | 71.68 |
| DCU 224 M/C Sony | 8126 | 0.00012306 | 0.12306178 | 1310720 | 5688.2 | 8126 | 161.28 |
| Kodak KAI-08050 | 33653 | 2.9715E-05 | 0.02971503 | 8147712 | 23557.1 | 33653 | 242.11 |

Figure 12a

| | pixels / sq.mm | mm/px | μm/px | # pixels | Protozoa (type A) - 10μm | Protozoa (type B) - 50μm | Protozoa (type C) - 1000μm | sensor area size (sq.mm) |
|---|---|---|---|---|---|---|---|---|
| Andanta Ultra-High Res CCD | 4933 | 0.00020272 | 0.2027164 | 111000000 | 49.33 | 246.65 | 4933 | 22500 |
| Megaplus ER 11000 (lower) | 12732 | 7.8542E-05 | 0.07854226 | 11000000 | 127.32 | 636.6 | 12732 | 864 |
| Megaplus ER 11000 (upper) | 111111 | 9E-06 | 0.00900001 | 96000000 | 1111.11 | 5555.55 | 111111 | 864 |
| Kodak KAI-11002 | 12458 | 8.027E-05 | 0.08026971 | 11100000 | 124.58 | 622.9 | 12458 | 891 |
| DCU 223 M/C Sony | 10971 | 9.1149E-05 | 0.09114939 | 786432 | 109.71 | 548.55 | 10971 | 71.68 |
| DCU 224 M/C Sony | 8126 | 0.00012306 | 0.12306178 | 1310720 | 81.26 | 406.3 | 8126 | 161.28 |
| Kodak KAI-08050 | 33653 | 2.9715E-05 | 0.02971503 | 8147712 | 336.53 | 1682.65 | 33653 | 242.11 |

Figure 12b

| | pixels / sq.mm | mm/px | µm/px | # pixels | Rotifiers (type A) - 100µm | Rotifiers (type A) - 500µm | Rotifiers (type B) - 50µm | Rotifiers (type B) - 2000µm | sensor area size (sq.mm) |
|---|---|---|---|---|---|---|---|---|---|
| Andanta Ultra-High Res CCD | 4933 | 0.00020272 | 0.2027164 | 111000000 | 493.3 | 2466.5 | 246.65 | 9866 | 22500 |
| Megaplus ER 11000 (lower) | 12732 | 7.8542E-05 | 0.07854226 | 11000000 | 1273.2 | 6366 | 636.6 | 25464 | 864 |
| Megaplus ER 11000 (upper) | 111111 | 9E-06 | 0.00900001 | 96000000 | 11111.1 | 55555.5 | 5555.55 | 222222 | 864 |
| Kodak KAI-11002 | 12458 | 8.027E-05 | 0.08026971 | 11100000 | 1245.8 | 6229 | 622.9 | 24916 | 891 |
| DCU 223 M/C Sony | 10971 | 9.1149E-05 | 0.09114939 | 786432 | 1097.1 | 5485.5 | 548.55 | 21942 | 71.68 |
| DCU 224 M/C Sony | 8126 | 0.00012306 | 0.12306178 | 1310720 | 812.6 | 4063 | 406.3 | 16252 | 161.28 |
| Kodak KAI-08050 | 33653 | 2.9715E-05 | 0.02971503 | 8147712 | 3365.3 | 16826.5 | 1682.65 | 67306 | 242.11 |

Figure 12c

| | pixels / sq.mm | mm/px | µm/px | # pixels | Amoeba 700µm | Amoeba 1000µm |
|---|---|---|---|---|---|---|
| Canon D30, 3MP | 95.4 | 0.0104822 | 10.48218 | 3000000 | 66.78 | 95.4 |
| Nikon Coolpix 995, 3MP | 290 | 0.0034483 | 3.4482759 | 3000000 | 203 | 290 |
| Minolta Xi, 3MP | 384 | 0.0026042 | 2.6041667 | 3000000 | 268.8 | 384 |
| OmniVision OV5620, 5MP | | | 2.2 | 5000000 | 318.1818 | 454.5455 |
| OmniVision OV5630/5633, 5MP | | | 1.75 | 5000000 | 400 | 571.4286 |
| OmniVision OV8810/8812, 8MP | | | 1.4 | 8000000 | 500 | 714.2857 |

Figure 13

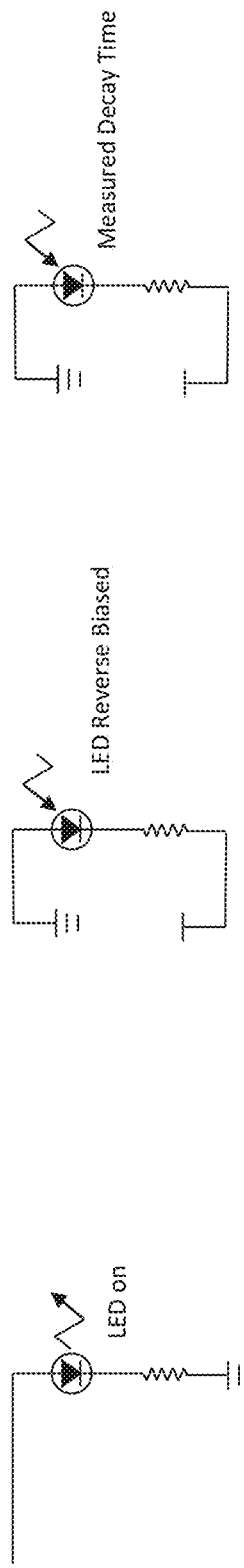

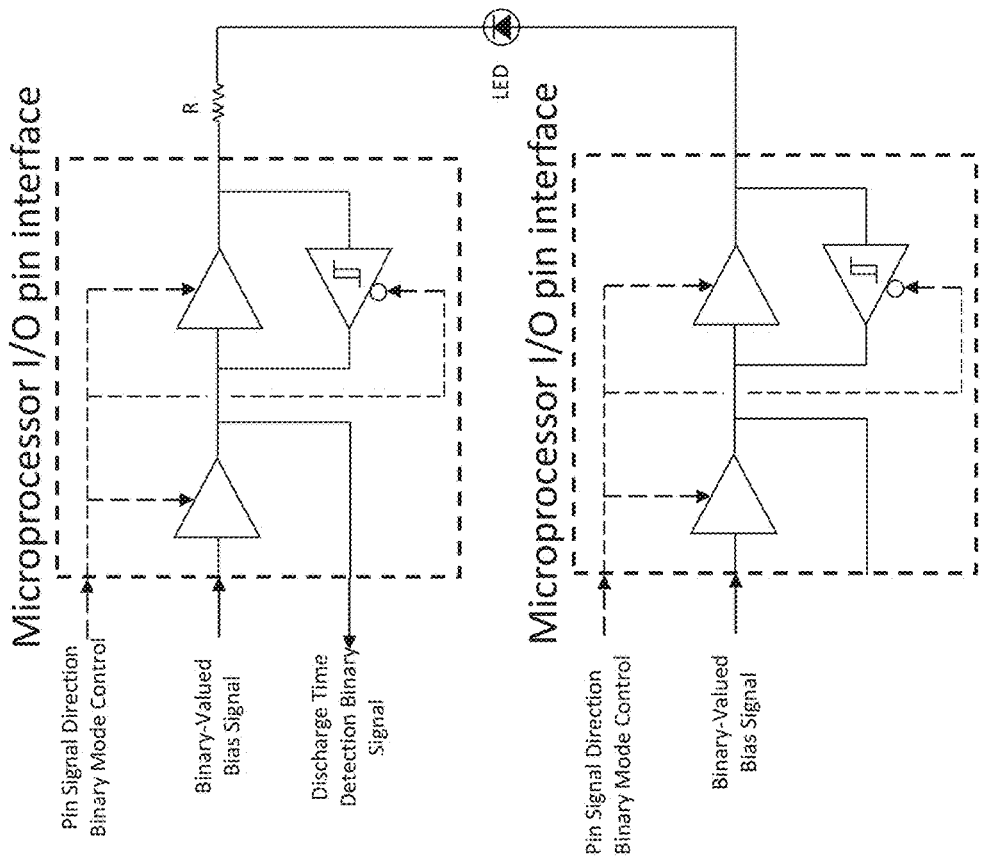
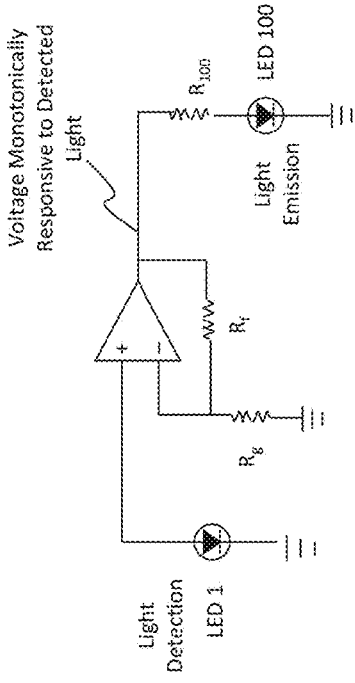
Figure 36
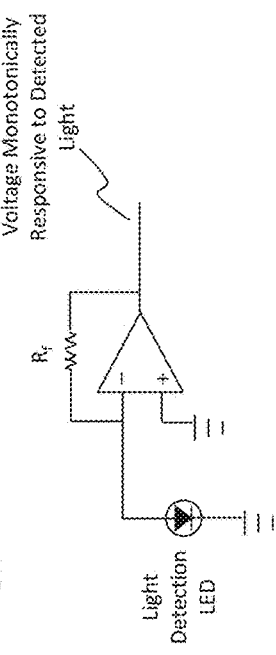
Figure 37
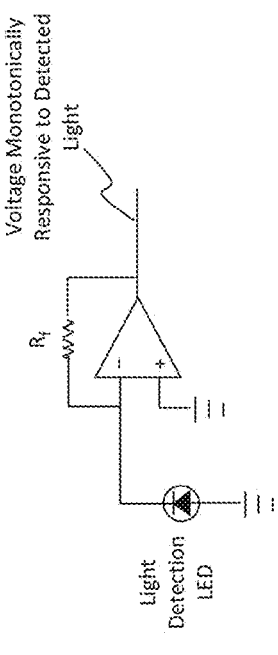
Figure 38
Figure 39

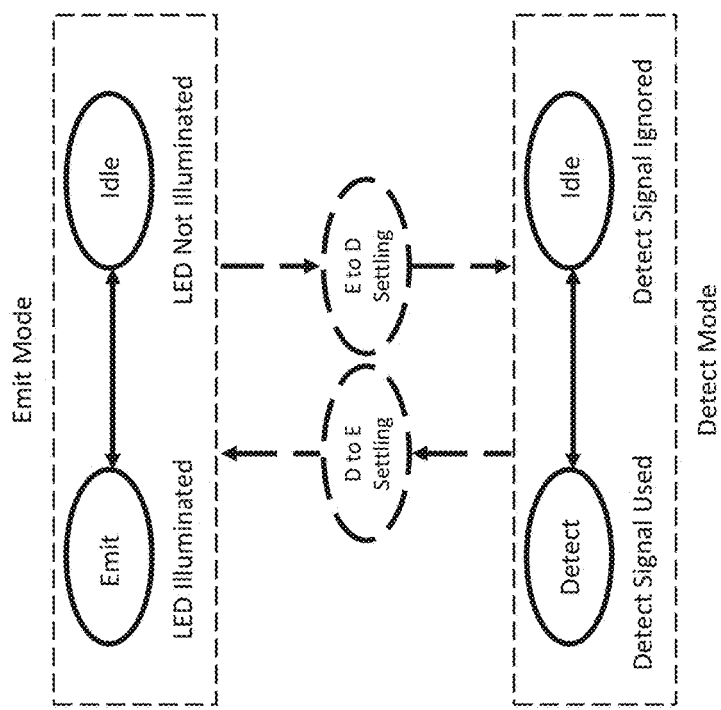
Figure 46
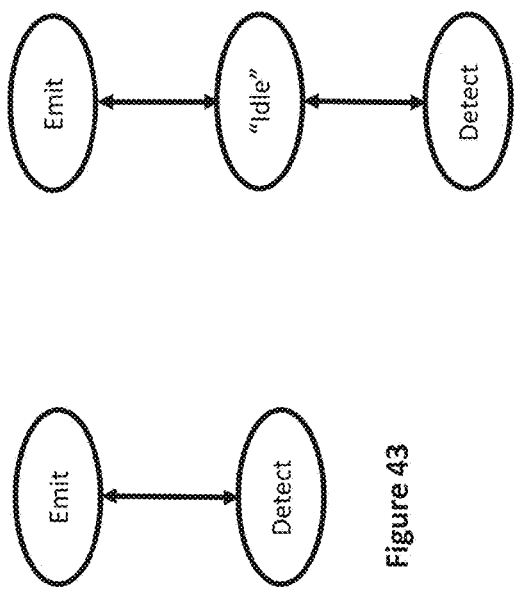
Figure 44
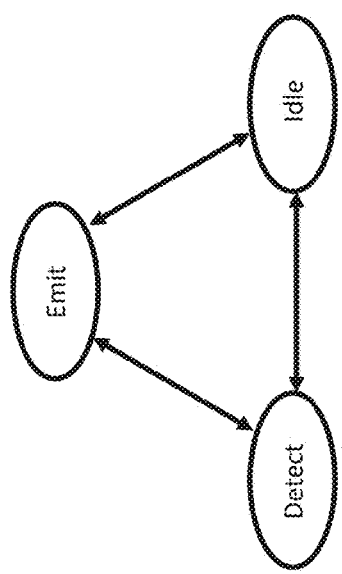
Figure 45
Figure 43

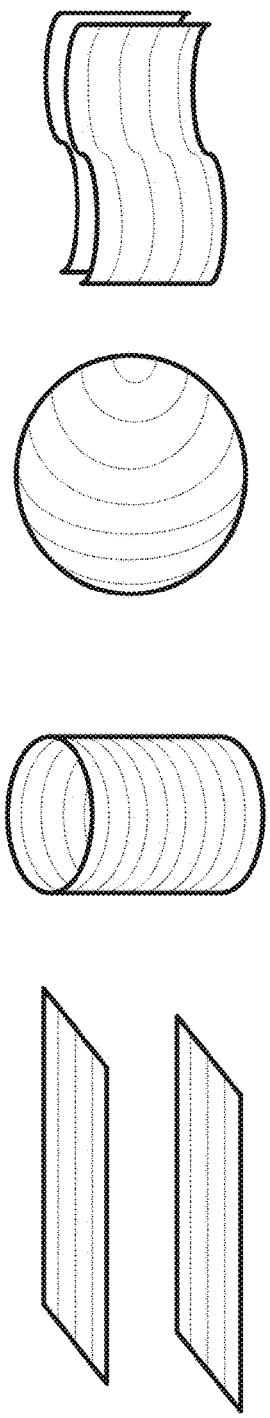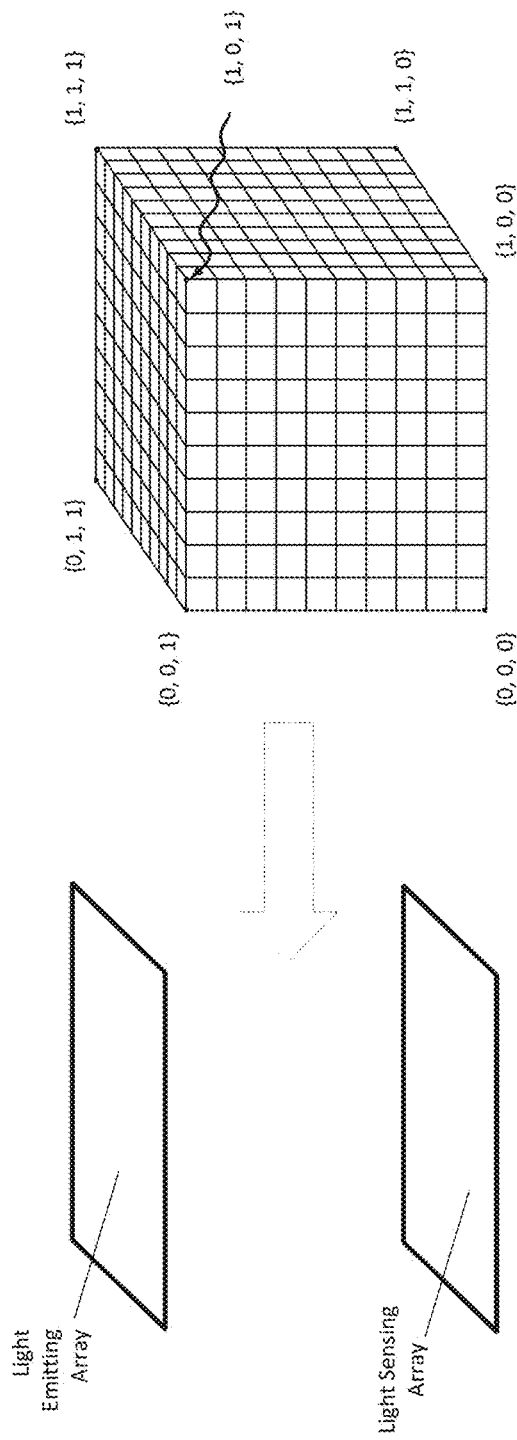

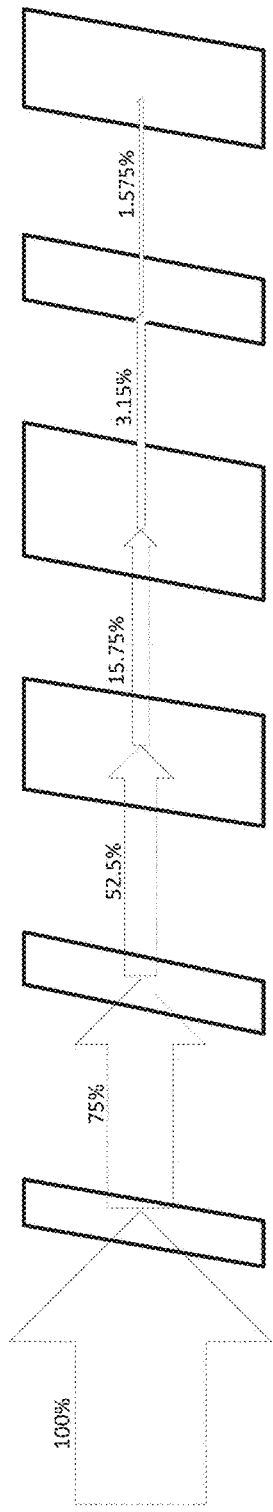

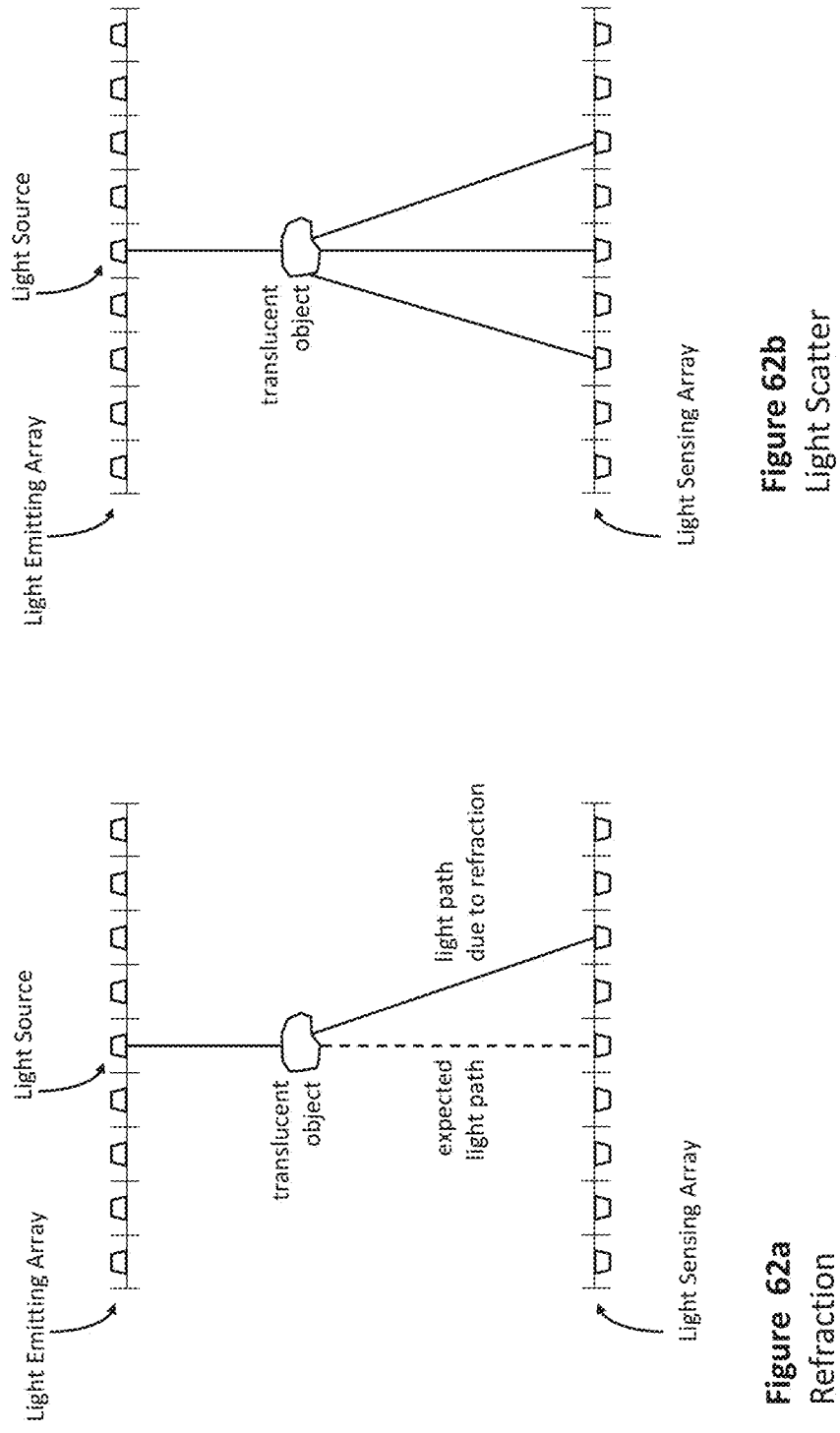

Reflection

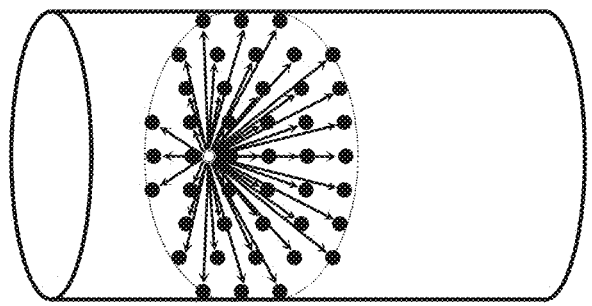
Figure 63f
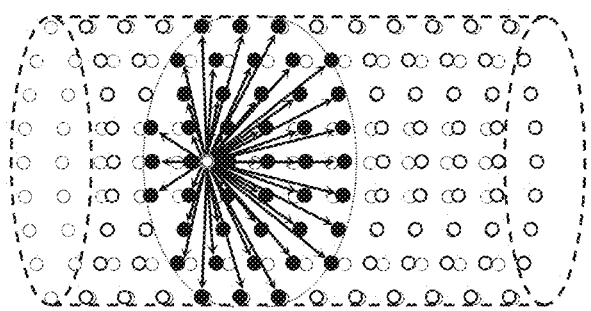
Figure 63e
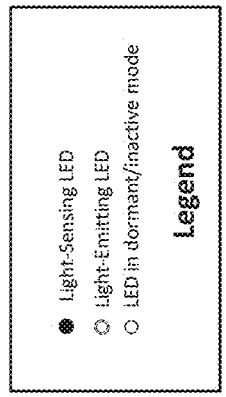
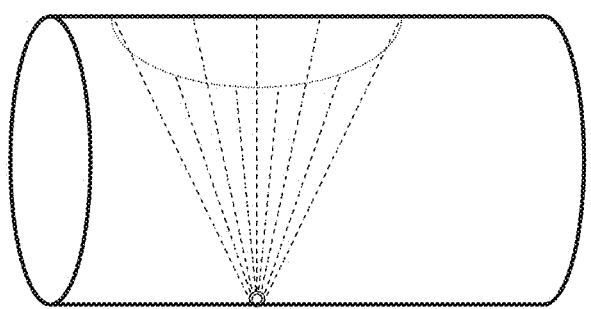
Figure 63d

Adapted from: Cappelli, Raffaele; Ferrara, Matteo; Maltoni, Davide. "Minutia Cylinder-Code: A New Representation and Matching Technique for Fingerprint Recognition." IEEE Transactions on Pattern Analysis and Machine Intelligence. December 2010 (Vol. 32 No. 12). Pp 2128-2141.

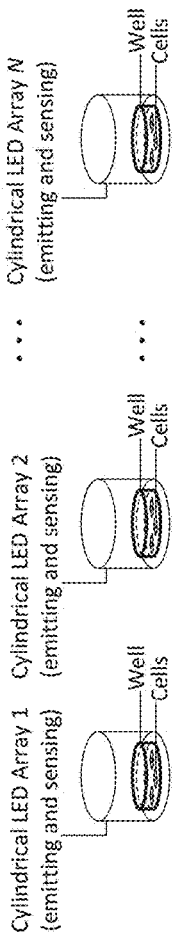
Figure 81a
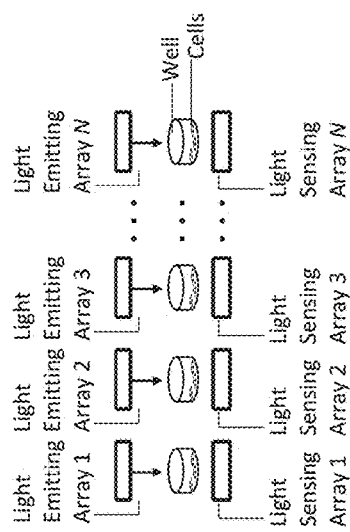
Figure 81a
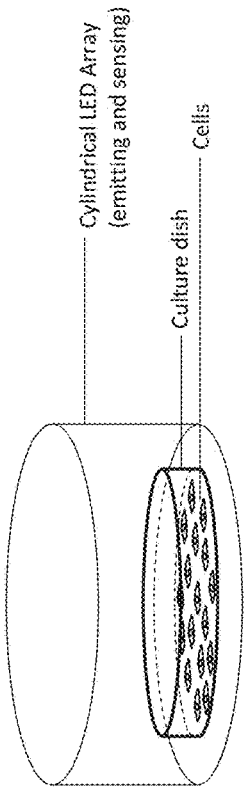
Figure 81b
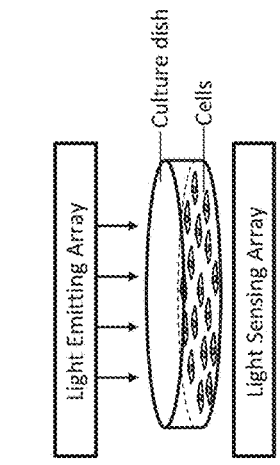
Figure 82b
Figure 82a

OPTICAL TOMOGRAPHY FOR MICROSCOPY, CELL CYTOMETRY, MICROPLATE ARRAY INSTRUMENTATION, CRYSTALLOGRAPHY, AND OTHER APPLICATIONS

CROSS-REFERENCE TO RELATED APPLICATIONS

This application is a Continuation-In-Part of U.S. patent application Ser. No. 12/817,107, filed Jun. 16, 2010, now U.S. Pat. No. 8,885,035, issued on Nov. 11, 2014 which claims benefit of priority from Provisional U.S. Patent Application Ser. No. 61/268,900, filed Jun. 16, 2009, the contents of which were incorporated by reference.

COPYRIGHT & TRADEMARK NOTICES

A portion of the disclosure of this patent document may contain material, which is subject to copyright protection. Certain marks referenced herein may be common law or registered trademarks of the applicant, the assignee or third parties affiliated or unaffiliated with the applicant or the assignee. Use of these marks is for providing an enabling disclosure by way of example and shall not be construed to exclusively limit the scope of the disclosed subject matter to material associated with such marks.

BACKGROUND OF THE INVENTION

Field of the Invention

The present invention generally relates to electronic cameras electronic imaging, fluid flow microscopes, and image processing, and in particular to how these may be combined in various ways to create a small low-power inexpensive flow microscope element for applications in environmental remote telemetry sensing, bioreactor monitoring, and other applications.

The present invention pertains to tomography and 3D imaging, and more specifically to optical tomography for microscopy, cell cytometry, microplate array instrumentation, and other applications.

BACKGROUND

Powerful new sensor capabilities and telemetry costs are radically evolving and have been integrated into environmental and contamination monitoring systems and Geographic Information Systems (GIS) as described in related U.S. patent application Ser. No. 12/817,074 filed on Jun. 16, 2010. Still-image, video, and audio field sensors can provide very useful environmental information as argued therein. Among the more useful possible applications for still-image and video is an inexpensive submersible flow microscope that can be used to visually monitor micro-organism and other microscopic affairs in flowing or standing surface water (among other uses). Such a flow microscope would need to be physically small, sturdy, low-energy consuming, easy to use, inexpensive, and remotely controllable by electrical or data signals. Once crafted, the resulting technology can be used as a laboratory instrument, for example as can be used in conjunction with a bioreactor.

To facilitate the above goals, a number of technology developments and particulars of possible flow microscope optical arrangements can be leveraged. In particular, image sensing elements are decreasing in cost as they increase in resolution and decrease in sensor array area size. These trends, together with the small size of objects to be viewed (assuming the incoming fluid is adequately clear of pre-filtered) permit a (2-dimensional) "contact imaging" approach, not unlike the 1-dimensional scanning bar arrangements employed in contemporary fax machines. Additional technology additions provide a wider range of performance, features, and capabilities, including opportunities for optical microscopic tomography. Additional advancements in power management electronics and image processing facilitate support other aforementioned needs of a flow microscope for environmental monitoring applications.

Tomography refers to imaging by sections or sectioning, through the use of any kind of penetrating wave, such as x-rays as in computer tomography, gamma rays, radio-frequency waves, electron-positron annihilation, electrons, ions, magnetic particles, etc. Optical tomography is a form of computed tomography that creates a digital volumetric model of an object by reconstructing images made from light transmitted and scattered through an object. Optical tomography relies on the object under study being at least partially transparent. The present invention presents applications and opportunities in optical tomography which have remained largely unexplored and undeveloped. Light emitting diodes, or LEDs, have both light emitting and sensing properties. With the abundance of high and low performance LEDs at an economical price, leveraging the properties of LEDS, organic LEDs (OLEDs), etc., is an important reason to consider such an invention. For example, OLEDs arrays are already in wide use in many types of electronic displays and they can be fabricated via printed electronics on a variety of surfaces such as glass, mylar, plastics, paper, etc. Leveraging some of the properties of such materials, LED arrays can be readily bent, printed on curved surfaces, etc. Such properties create vast opportunities for 3-D imaging in areas such as microscopy, cell cytometry, microplate array instrumentation, and other applications.

SUMMARY OF THE INVENTION

The invention comprises a fluid conduit comprising a port on each end of a thin flat transparent fluid transport region. The transparent fluid transport region comprises two parallel flat sides. A planar illumination surface is in contact with one of the flat sides; and a planar image sensing surface is in contact with the other flat side for receiving light fields and responsively creating electrical image signals. The light from the planar illumination surface travels into the transparent fluid transport region and produces a resulting light field affected by the fluid and any organisms or objects in the fluid. The resulting light field is presented to the planar image sensing surface, and the planar image sensing surface creates electrical image signals responsive to the resulting light field.

Various aspects of the invention may include a funnel port to capture water for environmental monitoring, an screen attached or adjacent to the funnel to filter out water-borne debris, and one or more electric knife valve(s) for trapping fluids for a fixed view or for removing debris at fluid constrictions. One or more pumps may be incorporated to facilitate desired fluid flow or to clear blockages or debris from the system.

The inventive system may also include power management electronics wherein electrical power is generated by fluid flow.

Electric illumination provides a light source from the bottom and a video and/or imaging sensor is positioned on the opposite side of a transparent flat fluidic passageway. The imaging sensor captures the images of particles of microscopic organisms that are suspended in the water. The imaging sensor can be implemented (with or without lenses) in a 2-dimensional manner similar to the 1-dimensional imaging arrangements of a document scanner. The source of illumination may be a light-emitting array. The planar illumination surface may be individual light-emitting pixels wherein the individual light-emitting pixels can be sequenced.

The light-emitting array may provide sequenced spatially modulated illumination, the sequence operated as part of the imaging system producing a fully-formed image output. The array may produce a partially-formed image output that can be subsequent processed by another processor to produce a fully-formed image output.

The invention provides data that can be used for optical tomography or used to produce tomography output.

BRIEF DESCRIPTION OF THE DRAWINGS

The above and other aspects, features, and advantages of the present invention will become more apparent upon consideration of the following description of preferred embodiments, taken in conjunction with the accompanying drawing figures.

FIG. 2b depicts an adaptation of the exemplary embodiment of FIG. 1c further comprising an internal pump servicing the opposite port than the adaptation of FIG. 2a.

FIG. 4b depicts flow in one direction through the exemplary fitting and housing arrangement of FIG. 4a.

FIG. 4c depicts flow in the opposite direction as that for FIG. 4b through the exemplary fitting and housing arrangement of FIG. 4a.

FIG. 12a is a table comparing attributes example contemporary high-resolution optical image-sensing element products to the width of example Amoeba sizes.

FIG. 12b is a table comparing attributes example contemporary high-resolution optical image-sensing element products to the width of example Protozoa sizes.

FIG. 12c is a table comparing attributes example contemporary high-resolution optical image-sensing element products to the width of example Rotifer sizes.

FIG. 13 is a table comparing attributes example contemporary miniature inexpensive cell-phone camera image-sensing element products to the width of example Amoeba sizes.

FIG. 14b depicts the exemplary single-cell organism in comparison an exemplary image sensor pixel array spacing of twice the resolution of that in FIG. 14a.

FIG. 14c depicts the exemplary single-cell organism in comparison an exemplary image sensor pixel array spacing of four times the resolution of that in FIG. 14a.

FIG. 30a shows an example schematic diagram of a light-emitting LED.

FIG. 30b shows an example schematic diagram of a light-sensing LED in a reverse-bias arrangement.

FIG. 30c shows an example schematic diagram of a light-sensing LED measuring decay time.

FIGS. 36-39 depict various exemplary circuits demonstrating various exemplary approaches to detecting light with an LED.

FIGS. 43-46 depict exemplary state diagrams for the operation of the LED and the use of input signals and output signals.

FIGS. 47a-47d shows exemplary geometries of light emitting and light sensing arrangements for various optical tomography systems.

FIG. 48 shows an example embodiment of a discretized space between a planar light emitting and light sensing arrangement in an optical tomography system.

FIG. 53a depicts an example cascade of non-uniform light loss transmission through objects of different thicknesses.

FIG. 53b depicts an example set of data based on FIG. 53a showing a relationship between transmittance and percentage of light loss.

FIG. 62a depicts an example of refraction of a light path transmitted through a transparent object between light emitting and light sensing arrangement.

FIG. 62b depicts an example of light scattering of a light path transmitted through a translucent object between light emitting and light sensing arrangement.

FIG. 63d depicts an example side view of emitting LED from the back side of the cylindrically shaped system to the front side.

FIG. 63e depicts an example emitting LED emitting light in and among LEDs in an emitting array from the back side of the cylindrically shaped system to the front side wherein a plurality of sensing LEDs sense the emitted light among LEDs in a sensing array.

FIG. 63f depicts an example emitting LED emitting light from the back side of the cylindrically shaped system to the front side wherein a plurality of sensing LEDs sense the emitted light.

FIGS. 66a-66b show an example embodiment of a discretization of space for a cylindrical light emitting and light sensing arrangement in an optical tomography system, wherein FIG. 66b shows increased discretization.

FIG. 68b illustrates a side view of the example holding module of FIG. 68a.

FIG. 69b illustrates a side view of the example holding module of FIG. 69a.

FIG. 70b illustrates a side view of the example holding module of FIG. 70a.

FIG. 74b depicts an exemplary graphical rendering in a visualizer module of an activation of discrete voxels intersected by the light path in discretized three-dimensional space.

FIG. 78b illustrates a side view of FIG. 78a.

FIG. 81a depicts an example embodiment of a microplate with a planar light emitting and light sensing arrangement applied to each well of the microplate in an optical tomography system.

FIG. 81b depicts an example embodiment of a microplate with a cylindrical light emitting and light sensing arrangement applied to each well of the microplate in an optical tomography system.

FIG. 82a depicts an example embodiment of a culture dish with a planar light emitting and light sensing arrangement in an optical tomography system.

FIG. 82b depicts an example embodiment of a culture dish with a cylindrical light emitting and light sensing arrangement in an optical tomography system.

FIG. 83 depicts an example embodiment of a microfluidic plate with a planar light emitting and light sensing arrangement in an optical tomography system.

FIG. 84 depicts another example microfluidic plate with a planar light emitting and light sensing arrangement in an optical tomography system.

FIG. 85 depicts an example embodiment of a culture chamber, with a planar light emitting and light sensing arrangement in an optical tomography system.

DETAILED DESCRIPTION

In the following detailed description, reference is made to the accompanying drawing figures which form a part hereof, and which show by way of illustration specific embodiments of the invention. It is to be understood by those of ordinary skill in this technological field that other embodiments can be utilized, and structural, electrical, as well as procedural changes can be made without departing from the scope of the present invention. Wherever possible, the same element reference numbers will be used throughout the drawings to refer to the same or similar parts.

The present invention is an electronic imaging flow-microscope for use in applications such as environmental remote telemetry sensing and bioreactor process monitoring. The invention can also be used in a wide range of other applications, such as monitoring in manufacturing processes or monitoring body fluids in medical applications.

Figure 1A:
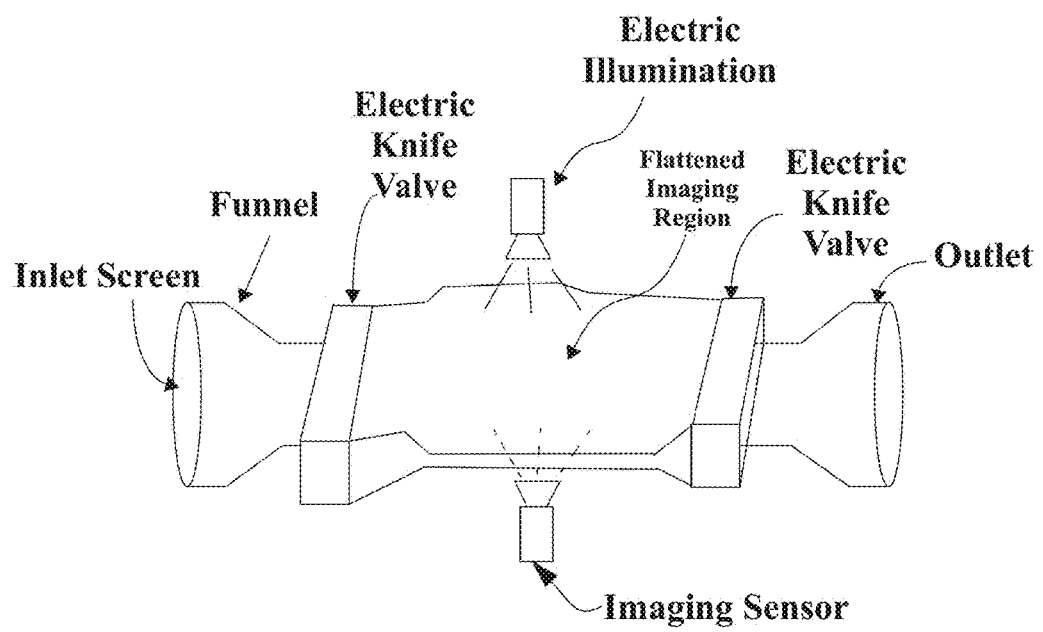
FIG. 1a depicts an exemplary embodiment of the invention with exemplary features for environmental remote telemetry sensing applications.

FIG. 1a depicts the invention with features for environmental remote telemetry sensing applications. For environmental monitoring, monitored water can flow into the funnel. In some applications, a screen attached within or adjacent to the funnel can filter out debris in the water. Electric illumination provides light source from the bottom and a video and/or imaging sensor on the opposite side of a transparent flat fluidic passageway captures the images of particles of microscopic organisms that are suspended in the water. In some applications, the imaging sensor can be implemented (without lenses) in a 2-dimensional manner similar to the 1-dimensional imaging arrangements of a document scanner. The imaging sensor may include a light-emitting array as the source of illumination providing sequenced spatially modulated illumination, the sequence operated as part of the imaging system. This arrangement produces a fully-formed image output. The arrangement may also produce a partially-formed image output that can be subsequent processed by another processor to produce a fully-formed image output. The arrangement also can be used to produce tomography output. The imaging sensor also can have magnifying lenses.

One or more electric knife valve(s) may be operated to trap fluids for a fixed view. The knife valves may be designed in conjunction with the filters so as to not create a situation wherein small water organisms are injured. In some applications, the electric knife valve(s) can be operated in such a manner as to remove debris at fluid constrictions.

Figure 1B:
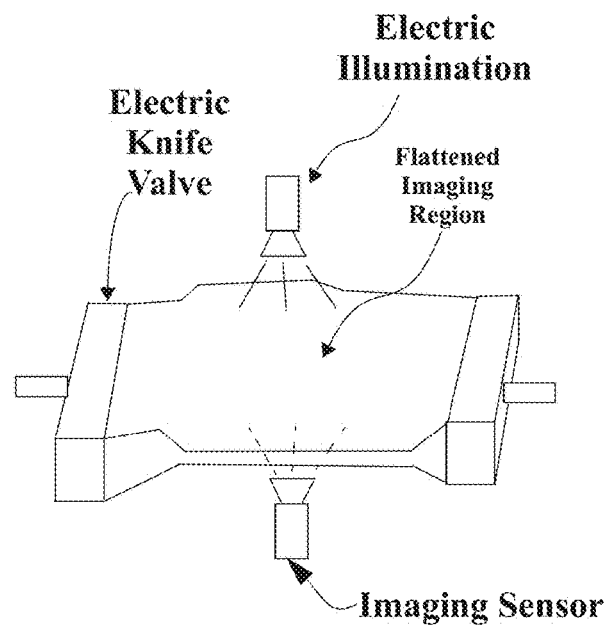
FIG. 1b depicts an exemplary embodiment of the invention with exemplary features for bioreactor monitoring applications.

FIG. 1b depicts exemplary features for applications such as bioreactor process monitoring, manufacturing process monitoring, monitoring of body fluids in medical applications, etc. In such applications the funnel, screen, and/or valves may be replaced with tubing ports, size filters, or other elements and/or arrangements as advantageous for the application.

Figure 1C:
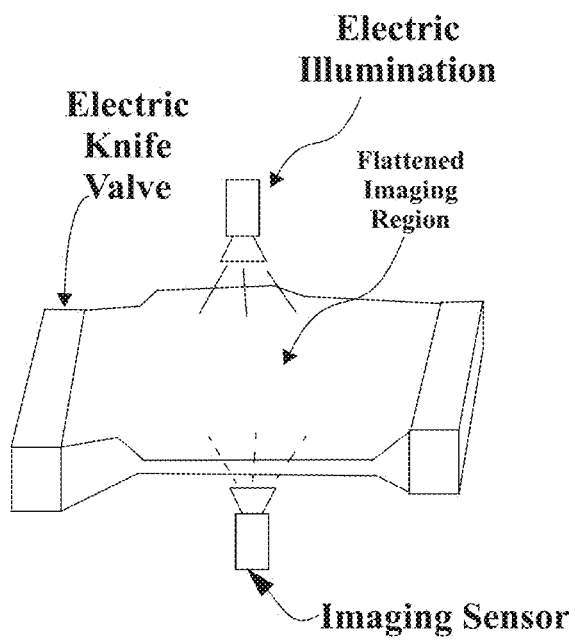
FIG. 1c depicts a generic form of an exemplary embodiment of the invention that can be augmented with different types of external flow fittings on the ports of the device so as to selectively form the exemplary embodiments of FIG. 1a and FIG. 1b as well as other configurations arrangements.

FIG. 1c depicts a generic form of the invention that can be augmented with different types of external flow fittings on the ports of the device so as to selectively form the embodiments of FIG. 1a and FIG. 1b as well as other configurations arrangements.

In one arrangement, the invention can comprise a fluid conduit comprising a port on each end and a thin flat transparent fluid transport region between the ports, the transparent fluid transport region comprising two parallel flat sides; a planar illumination surface in contact with one of the flat sides of the transparent fluid transport region; and a planar image sensing surface in contact with the other of the flat sides of the transparent fluid transport region for receiving light fields and responsively creating electrical image signals.

In such an arrangement, light from the planar illumination surface travels into the transparent fluid transport region, producing a resulting light field affected by the fluid and any microscopic organisms and/or microscopic objects in the fluid, the resulting light field is presented to the planar image sensing surface, and the planar image sensing surface creates electrical image signals responsive to the resulting light field.

Figure 2A:
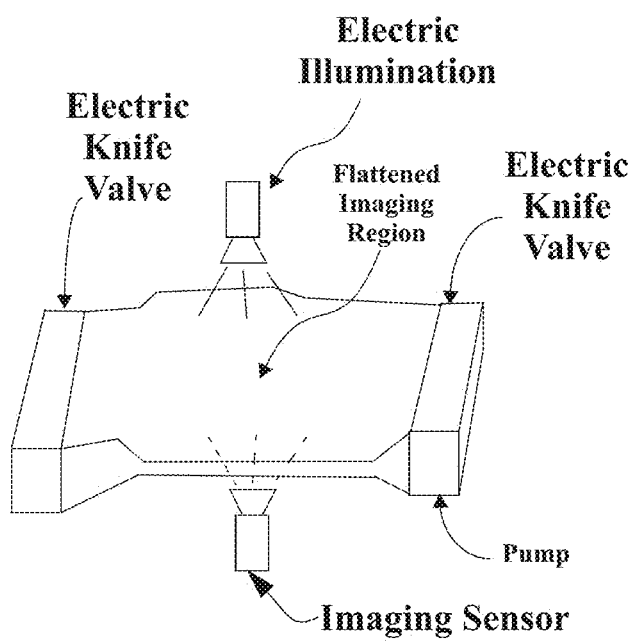
FIG. 2a depicts an adaptation of the exemplary embodiment of FIG. 1c further comprising an internal pump servicing one port.
Figure 2B:
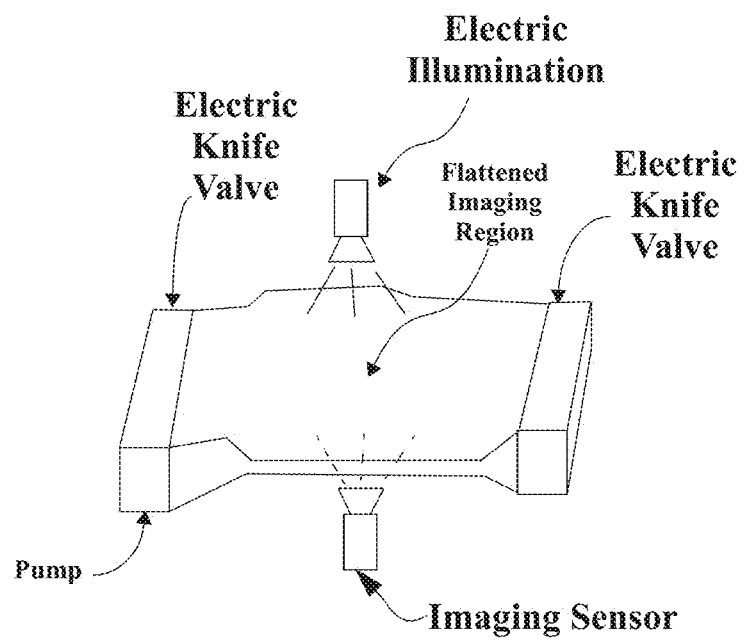
Figure 2C:
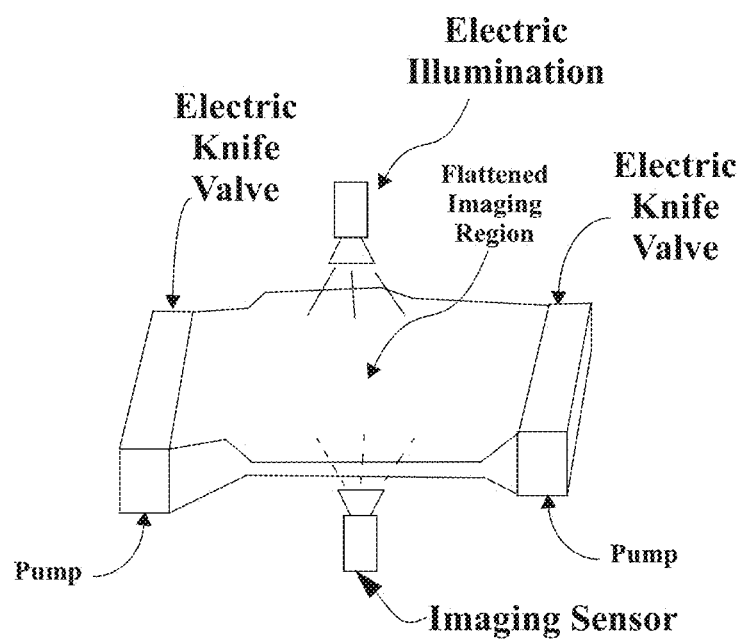
FIG. 2c depicts an adaptation of the exemplary embodiment of FIG. 1c further comprising two internal pumps, one to service each port.

In some situations, the water or fluid to flow through the flow microscope has enough inherent pressure to flow through the flow microscope at an adequate pace. In some situations, the inherent pressure may be too high and the invention can operate the electric knife valves to restrict the flow rate. In other situations, there may be inadequate inherent pressure or contrary-direction inherent pressure. In such situations, the invention can be further provided with one or more internal fluid pump(s). The pump(s) can be unidirectional. In other implementations, the pump(s) can be bidirectional. The pump(s) can be a diaphragm pump, a rotating vane or turbine pump. When the pump(s) are a rotating vane or turbine pump, the pump may also be used in a passive unpowered mode to generate an electrical signal responsive to rotation of the rotating vane or turbine. The electrical signal also can be used for flow-rate measurements. FIG. 2a depicts an adaptation of FIG. 1c further comprising an internal pump servicing one port. FIG. 2b depicts an adaptation of FIG. 1c having an internal pump servicing the opposite port than the adaptation of FIG. 2a. FIG. 2c depicts an adaptation of FIG. 1c further comprising two internal pumps, one to service each port. In a variation of the arrangement depicted in FIG. 2c, one of the pump elements can be used as a pump and the other used as a flowmeter. In a further adaptation of this, one of the pumps can be replaced with flowmeter. When employing one or more pumps, the pumps can be, preventatively or as needed, be operated in pulsed and/or direction-reversing modes to prevent clogs, or clear accumulated debris, etc.

Exemplary Embodiments for Environmental Monitoring Applications

The invention can be used as a component in an environmental monitoring system or environmental GIS system as described in related U.S. patent application Ser. No. 12/817,074 filed on Jun. 16, 2010. For such applications, the invention can advantageously further internally comprise other types of sensors such as an oxygen sensor, pH sensor, temperature sensor, specialized ion sensor, affinity sensor, biomolecule sensor, etc.

Figure 3:
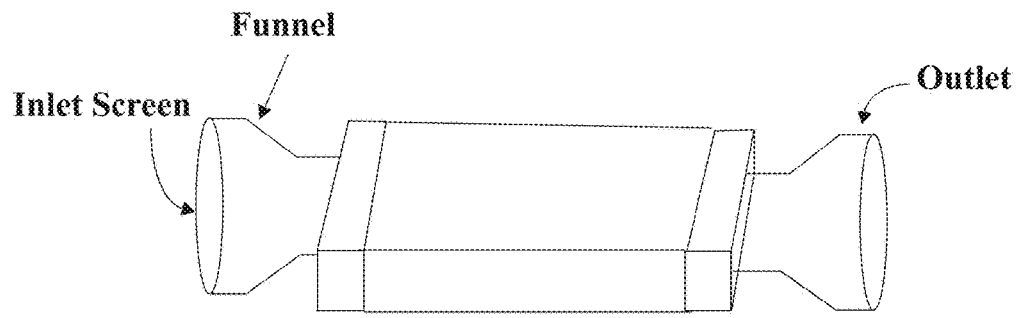
FIG. 3 depicts an exemplary housing arrangement for the exemplary embodiment of FIG. 1a, designed for flow in one direction.
Figure 4A:
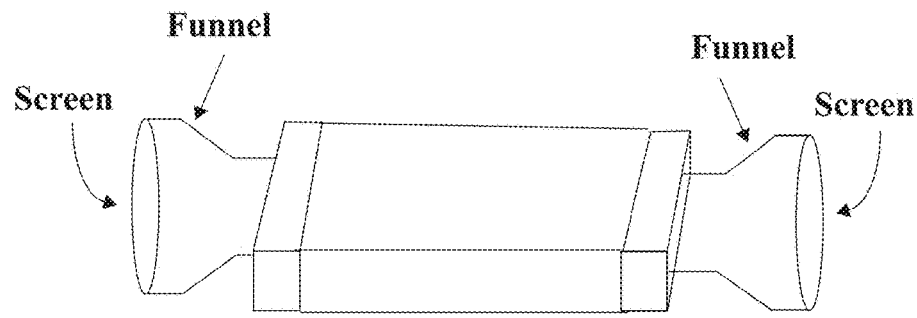
FIG. 4a depicts an exemplary fitting and housing arrangement as may be used in conjunction with the exemplary embodiments of FIGS. 2a-2c, designed for flow in both directions.
Figure 4B:
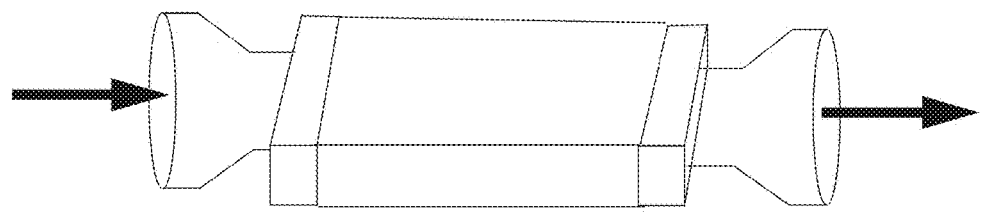
Figure 4C:
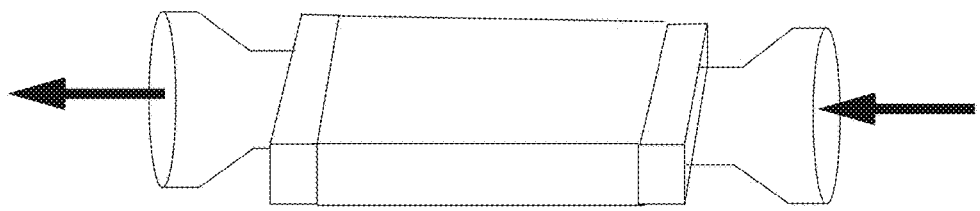
Figure 5A:
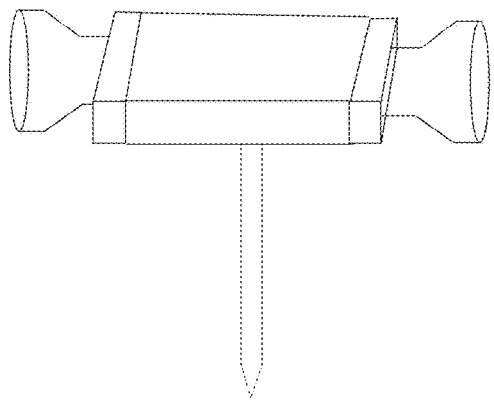
FIGS. 5a-5d depicts various exemplary staking arrangements for example as can be used to secure a flow camera in a flowing waterway or standing body of water.
Figure 5B:
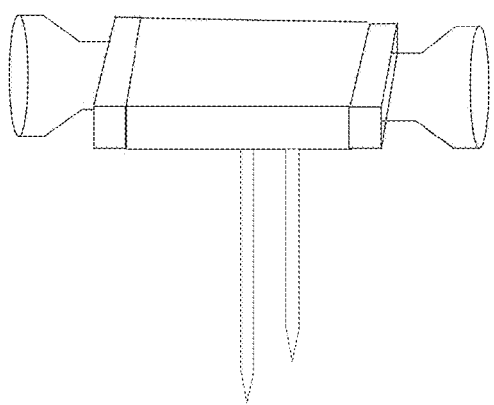
Figure 5C:
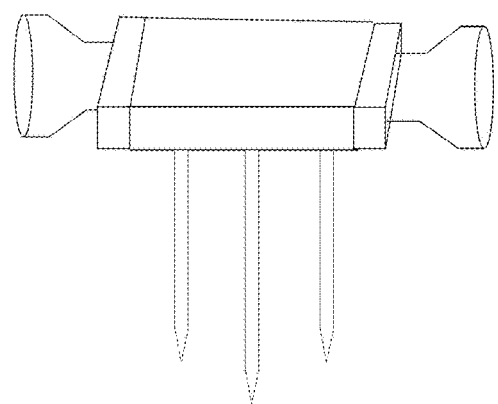
Figure 5D:
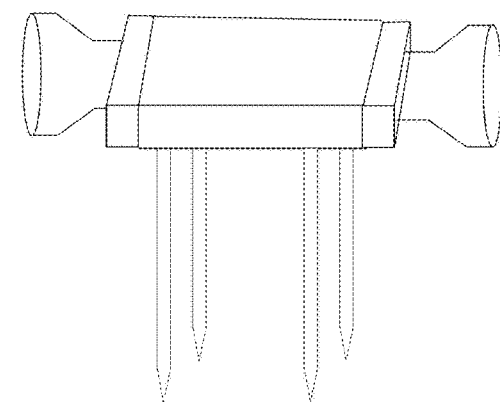

FIG. 3 depicts a housing arrangement of FIG. 1a, designed for flow in one direction. As another example, FIG. 4a depicts an fitting and housing arrangement as may be used in conjunction with FIGS. 2a-2c, designed for flow in both directions. Accordingly, FIG. 4b depicts flow in one direction through the fitting and housing arrangement of FIG. 4a, while FIG. 4c depicts flow in the opposite direction.

The invention may be deployed in flowing waterways (rivers, stream, brooks, tidal paths, estuaries, etc.), standing bodies of water (lakes, bays, shoreline coastal water, bogs, sloughs, swamps, etc.), or other volumes of moving, standing, or occasional water (underground water wells, urban piping, storm sewers, drainage ditches, levy areas, etc.). The invention in these cases is typically submerged when in operation (at least part of the time) and in most implementations may be provided with an electrical cable for signals In some deployments of the invention, the flow microscope preferably will be secured at a fixed location at a fixed distance from the water floor or shoring. In wild areas, the invention may be secured by stakes that can be pushed, hammered, or screwed into the ground. FIGS. 5a-5d depicts various exemplary staking geometry arrangements for example as can be used to secure a flow camera in a flowing waterway or standing body of water.

Figure 6:
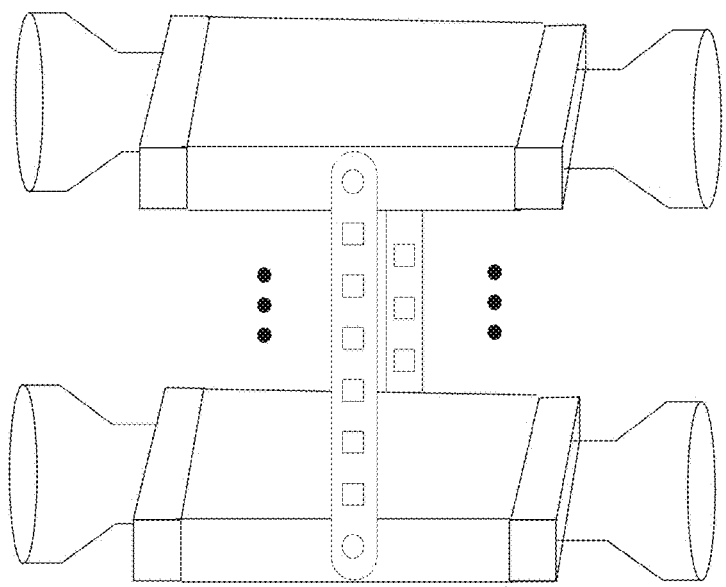
FIG. 6 depicts an exemplary aligned ganging arrangement as for example can be used to secure a group of flow camera in a surface waterway or body of water.
Figure 7:
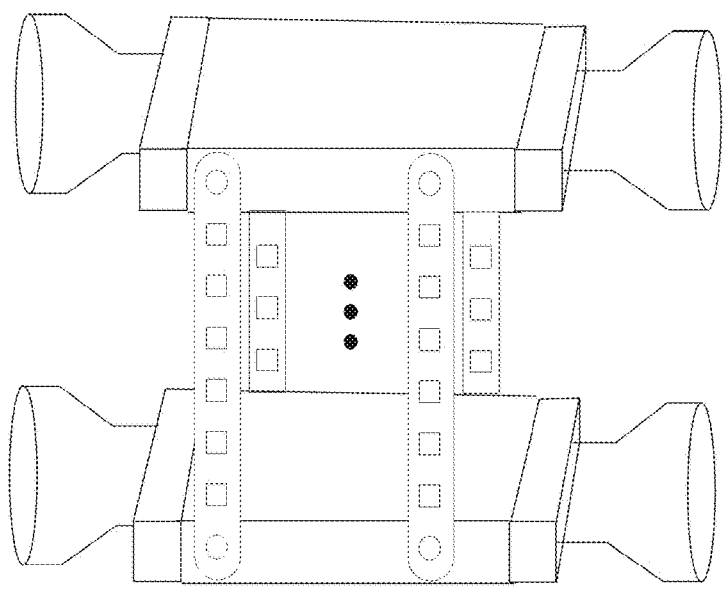
FIG. 7 depicts another exemplary aligned ganging arrangement providing more alignment stability that the arrangement of FIG. 6.

In some deployments of the invention, a plurality of flow microscopes will preferably be co-deployed in the same immediate location. For example, water may be sampled at various heights from the water floor, or various distances from the water shoring. FIG. 6 depicts an aligned ganging arrangement that can secure a group of flow cameras in a surface waterway or body of water. Here, any of a number of types and/or combinations of keyed holes (here depicted as squares), extrusions, mounting ears, aligning pins, keyed fasteners, etc. can be used to ensure a firm orthogonal mounting angle between each secured flow microscope and a mounting strap may be used to gang two or more flow microscopes together. FIG. 7 depicts another aligned ganging arrangement providing more alignment stability that the arrangement of FIG. 6. Other mounting, ganging, aligning, and fastener arrangements are of course possible and provided for by the invention. For example, the flow microscopes may be additionally or alternatively attached on other portions of the housing, flow fittings, etc. Resultantly ganged pluralities of flow microscopes can be vertically oriented, horizontal oriented, etc. Additionally, pluralities of ganged flow microscopes can themselves be ganged to create larger or more complex arrays.

Figure 8:
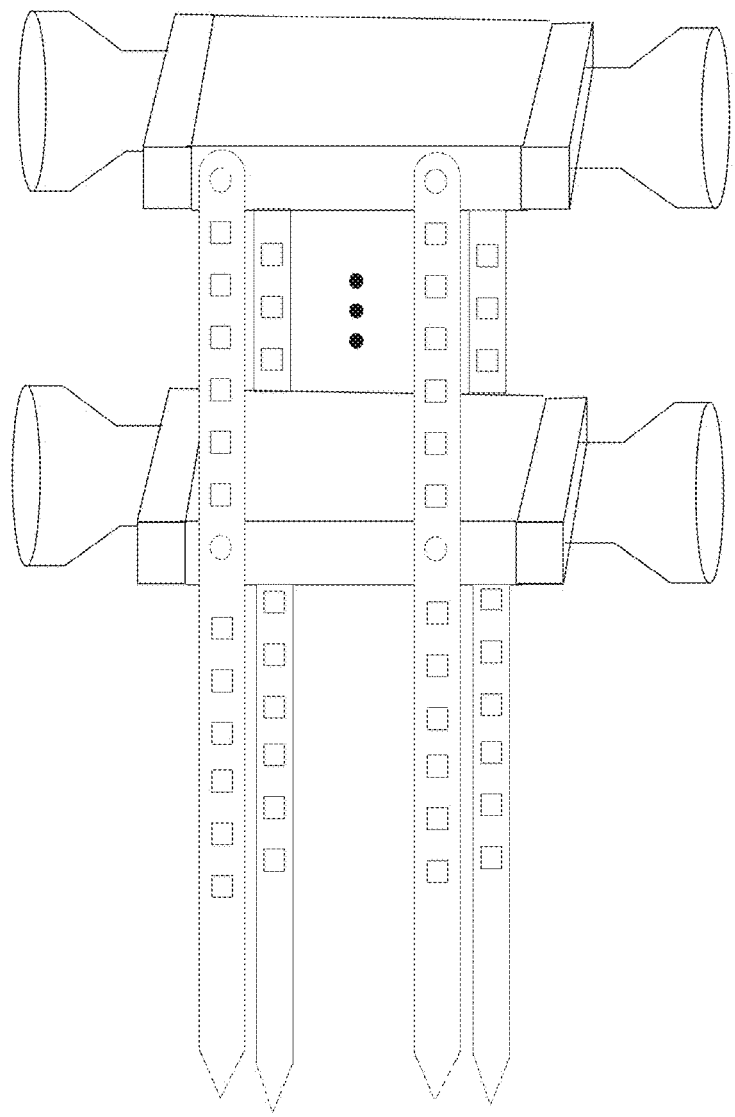
FIG. 8 depicts the exemplary aligned ganging arrangement of FIG. 7 adapted to provide staking as can be used to secure a flow camera in a surface waterway or body of water.

Such ganged pluralities of flow microscopes can be secured to the water floor or shoring in various ways. As one example, the ganging arrangements of FIG. 6 FIG. 7, etc. may be combined with a staking arrangement (for example, those depicted in any of FIGS. 5a-5d) on one of the flow microscopes. Alternatively, FIG. 8 depicts the aligned ganging arrangement of FIG. 7 adapted to provide staking as can be used to secure a flow camera in a surface waterway or body of water. Other arrangements are of course also possible and provided for by the invention.

Figure 9:
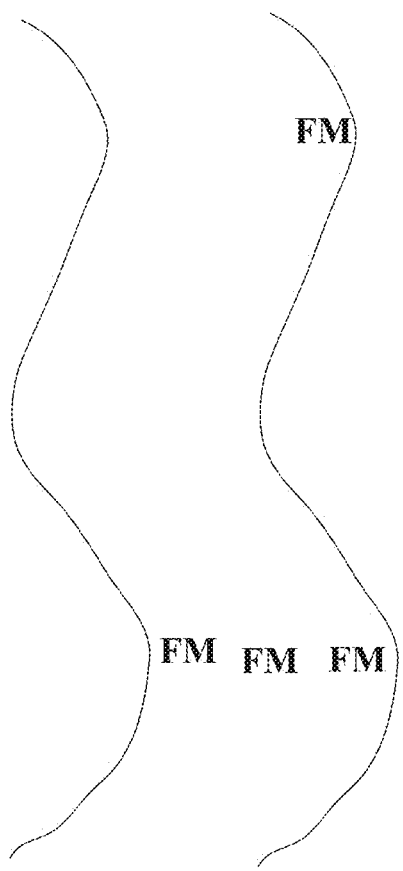
FIG. 9 depicts exemplary locations where one or more flow cameras may be located in a flowing waterway.

FIG. 9 depicts locations in a flowing waterway where one or more flow microscopes can be located in the manner described above.

Exemplary Embodiments for Bioreactor Monitoring Applications

Figure 10:
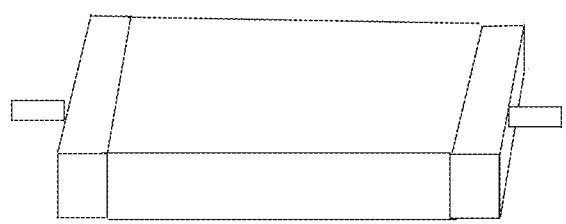
FIG. 10 depicts an exemplary housing arrangement for the exemplary embodiment of FIG. 1b.

As another application setting, the invention can be used in bioreactor process monitoring. FIG. 10 depicts a housing arrangement for FIG. 1b. As described earlier, the invention can include valves, pumps, and additional sensors (such as oxygen sensor, carbon dioxide sensor, pH sensor, temperature sensor, specialized ion sensor, affinity sensor, biomolecule sensor, etc.) as can be advantageous in a product or an application.

Figure 11:
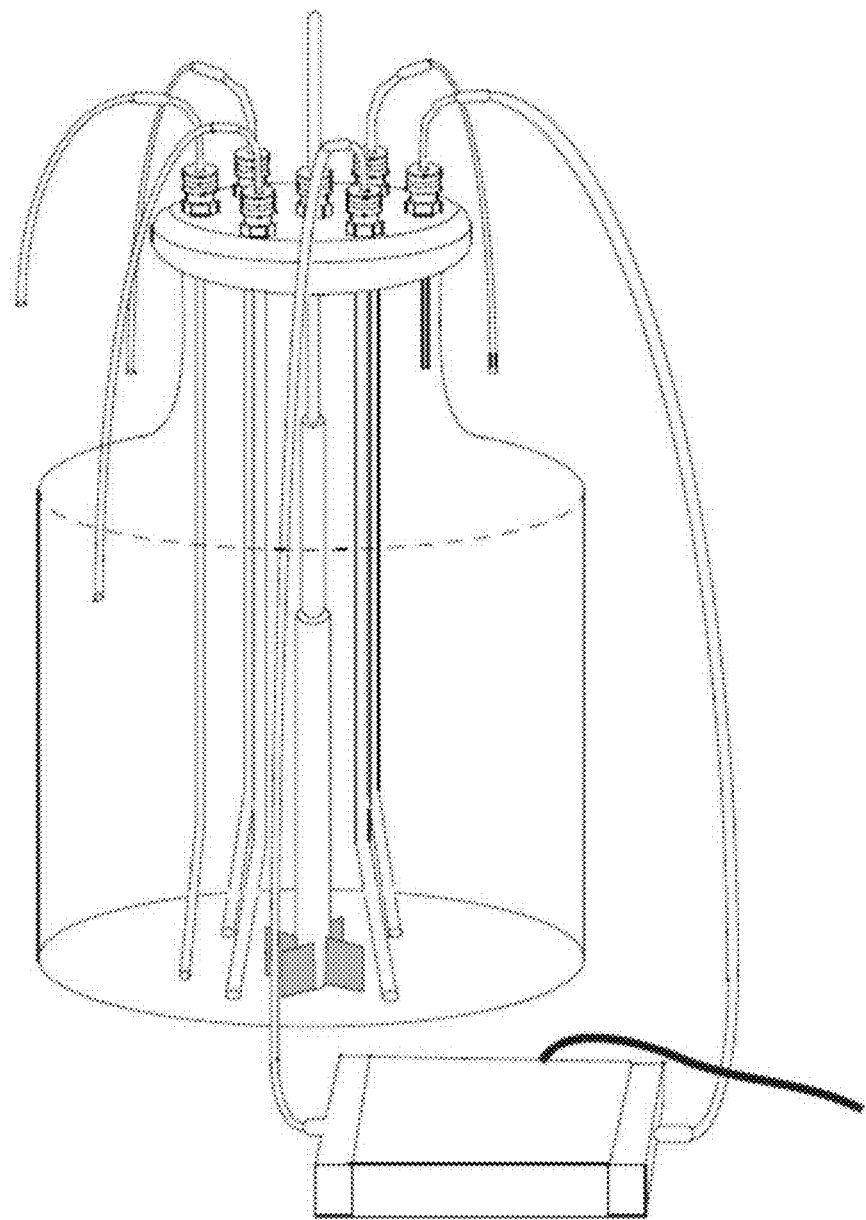
FIG. 11 depicts an exemplary application of the arrangement depicted in FIG. 10 in use with a laboratory or industrial bioreactor.

FIG. 11 depicts an application of the arrangement depicted in FIG. 10 for use with a laboratory or industrial bioreactor. In such an arrangement, it is likely advantageous for the flow microscope to include at least one pump so as to circulate the fluid out from and back into the bioreactor vessel. Such an arrangement may be useful for monitoring the density, development, health, activity, etc of microorganism populations within the fluid in the bioreactor vessel.

OTHER APPLICATIONS

The invention can also be used in a wide range of other applications, such as monitoring in manufacturing processes or monitoring body fluids in medical applications.

It is also noted that the imaging systems about to be described provide a platform for various types of optical microscopic tomography. This opens a very wide set of new possibilities and applications in the areas of microbiology, micro-fabrication, etc.

Exemplary Microscopic Imaging Implementations

The invention provides for small-sized, inexpensive, and innovative electronic imaging arrangements used to provide imaging functions for the flow microscope. A lens-based optical imaging system can be employed typically this would adding to cost, complexity, and size of the device. Alternatively, as discussed below, imaging sensing can be implemented without lenses in a 2-dimensional manner similar to the 1-dimensional imaging arrangements of a document scanner. In these approaches, effectively each image sensor pixel captures immediately emerging light from the fluid or its contents as will be explained. The various arrangements that can be used to leverage and exploit this optical arrangement can also be used to provide a platform for various types of optical microscopic tomography.

To begin, attention is first directed to a representative sample of the state of the art in high-resolution image sensor elements and comparing the direct-contact pixel count and spatial distribution to imaging of some representative one-celled organisms that would be of interest in monitoring environmental water conditions.

FIG. 12a is a table comparing attributes example contemporary high-resolution optical image-sensing element products to the width of example Amoeba sizes. Each row in the table represents an example commercial image sensor product whose resolution (indicated in column 5) ranges from 786,432 pixels to 11.1 million pixels. The spatial distribution of the pixels for each product is compared to the size of larger type of Amoeba, ranging from 700 micro-meters to 1000 micro-meters. The 6th and 7th column of the table represent how many pixels would be sufficient to cover the physical area of the size of one Amoeba.

FIG. 12b is a table comparing attributes example contemporary high-resolution optical image-sensing element products to the width of example Protozoa sizes. This table is similar but directed to various sizes of Protozoa, which typically ranges from 10 to 1000 micro-meters. The 6th, 7th, and 8th column of the table represent how many pixels would be sufficient to cover the physical area of the size of one Protozoa.

FIG. 12c is a table comparing attributes example contemporary high-resolution optical image-sensing element products to the width of example Rotifer sizes. The size of one type of Rotifer typically ranges 100 to 500 micro-meters, and that of another type ranges from 50 to 2000 micrometers. The 6th, 7th, and 8th columns of the table represent how many pixels would be sufficient to cover the physical area of the size of one Rotifer.

In summary, the current state of the art in image sensor products can produce "direct contact" images that would display at the following sizes on contemporary computer monitors:

Protozoa 10 μm in size
    Andanta Ultra-High Res CCD with 11.1 mega-pixel
        13.05 mm (0.51") on a Windows system
        17.40 mm (0.69") on an Apple/Macintosh system
    Megaplus ER 11000 with 96 mega-pixel
        293.99 mm (11.57") on a Windows system
        391.98 mm (15.43") on an Apple/Macintosh system Amoeba 700 μm in size
    Andanta Ultra-High Res CCD with 11.1 mega-pixel
        913.66 mm (35.97") on a Windows system
        1218.19 mm (47.96") on an Apple/Macintosh system
    Megaplus ER 11000 with 96 mega-pixel
        20579.34 mm (810.21") on a Windows system
        27438.46 mm (1080.25") on an Apple/Macintosh system Rotifiers 2000 μm in size
    Andanta Ultra-High Res CCD with 11.1 mega-pixel
        2610.46 mm (103") on a Windows system
        3480.53 mm (137") on an Apple/Macintosh system
    Megaplus ER 11000 with 96 mega-pixel
        58798.12 mm (2315") on a Windows system
        78395.61 mm (3086") on an Apple/Macintosh system The above calculations are based on Microsoft Windows operating system default display "DPI" of 96 PPI (one pixel occupies 0.2646 millimeters on the display screen) and Apple/Macintosh default of 72 PPI (one pixel occupies 0.3528 millimeters on the display screen).

Thus contemporary image sensors provide adequate resolution to provide usable 2-dimensional contact imaging at the scale of microorganisms of interest.

Additionally it is noted that the resolution and pixel-count of electronic image sensors (CCD, CMOS, photodiode, etc.) continues to improve annually, increasing the number of pixels that can be used to directly observe such microscopic organisms. On the contrary, some of the image sensors of older digital cameras of lower resolution are found to be insufficient. FIG. 13 is a table comparing attributes example contemporary miniature inexpensive cell-phone camera image-sensing element products to the width of example Amoeba sizes. The 6th and 7th column of the table represent how many pixels would be sufficient to cover the physical area of the size of one Amoeba, and such numbers are significantly lower than the models of camera discussed in earlier tables.

Figure 14A:
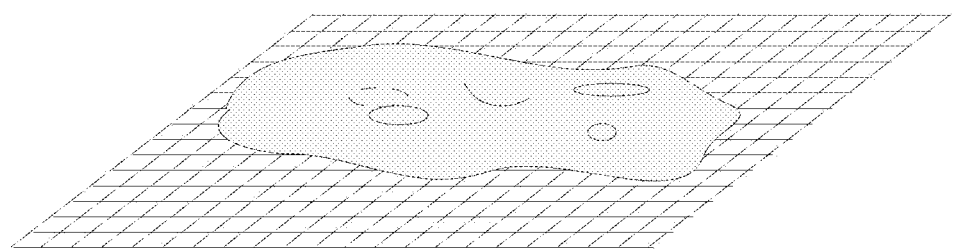
FIG. 14a depicts an exemplary single-cell organism in comparison with an exemplary image sensor pixel array spacing.
Figure 14B:
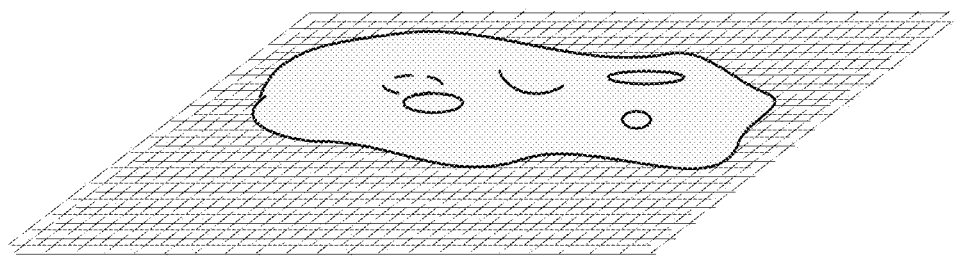
Figure 14C:
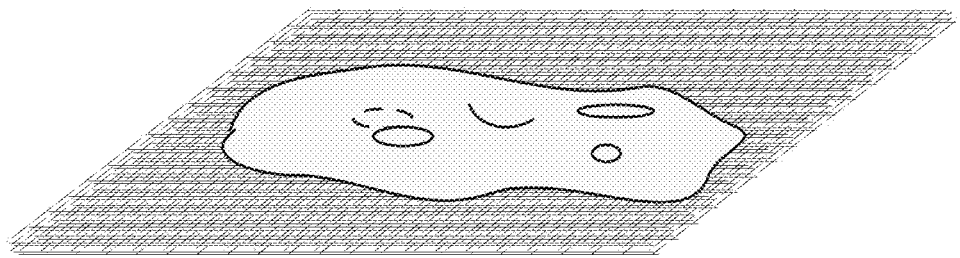

Further as to the use of contemporary image sensors for 2-dimensional contact imaging at the scale of microorganisms of interest, for the sake of illustration FIG. 14a depicts an exemplary single-cell organism in comparison an exemplary image sensor pixel array spacing, while FIG. 14b depicts the exemplary single-cell organism in comparison an exemplary image sensor pixel array spacing of twice the resolution and FIG. 14c depicts the exemplary single-cell organism in comparison an exemplary image sensor pixel array spacing of four times the resolution.

Figure 15:
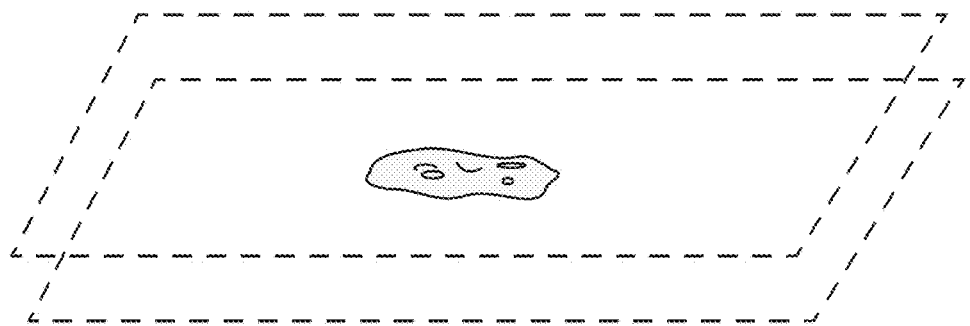
FIG. 15 depicts an exemplary single-cell organism in a fluid region between a planar illumination surface (top) and a parallel planar image sensing surface (bottom).

Attention is now directed to FIG. 15 which depicts an exemplary single-cell organism in a fluid region between a planar illumination surface (top) and a parallel planar image sensing surface (bottom). The planar illumination surface may be a uniformly lit optically diffused light source, a structured collimated light source, etc.

Figure 16:
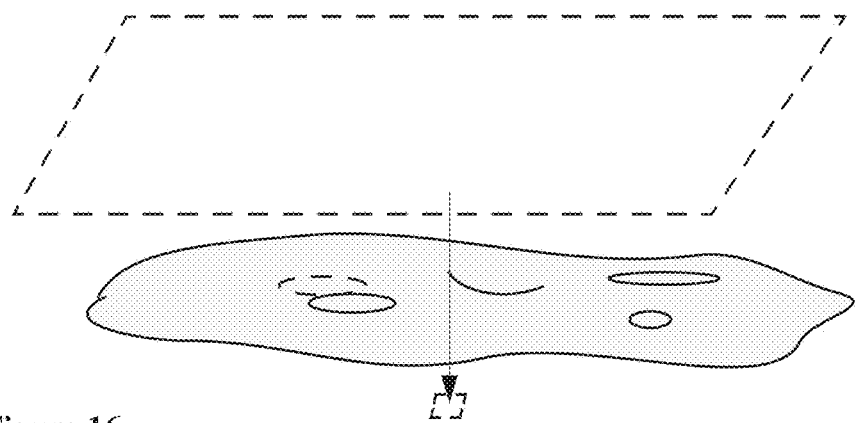
FIG. 16 depicts an exemplary straight light path through an exemplary translucent single-cell organism in a fluid region from an exemplary first area of the planar illumination surface to an exemplary pixel in the image sensor.
Figure 17:
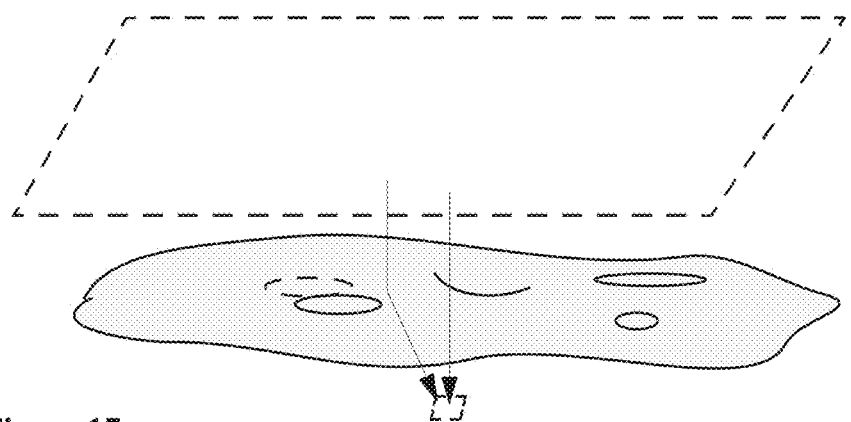
FIG. 17 depicts an augmentation of FIG. 16 also including an exemplary bent light path through an exemplary translucent single-cell organism in a fluid region from an exemplary second area of the planar illumination surface to an exemplary pixel in the image sensor.

FIG. 16 depicts an exemplary straight light path through an exemplary translucent single-cell organism in a fluid region from a first area of the planar illumination surface to a pixel in the image sensor. Such a light path would be produced by either a collimated or a optically diffused light source. As a next step, FIG. 17 depicts an augmentation of FIG. 16 which also includes a bent light path through the translucent single-cell organism in a fluid region from an second area of the planar illumination surface to a pixel in the image sensor. The image sensor pixel received the sum of both light paths, thus contributing to a lack of sharpness of the captured image and potentially other effects. It is noted that there is a huge distribution of such bent light paths, even with a collimated light source.

Figure 18:
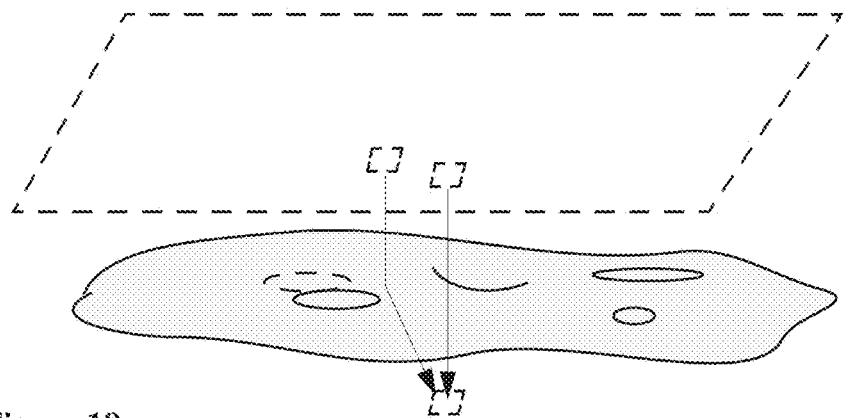
FIG. 18 depicts an adaptation of the situation depicted in FIG. 17 wherein the planar illumination surface comprises individual light-emitting pixels, one which serves as the exemplary first area of the planar illumination surface and the other of which serves as the exemplary second area of the planar illumination surface.
Figure 19:
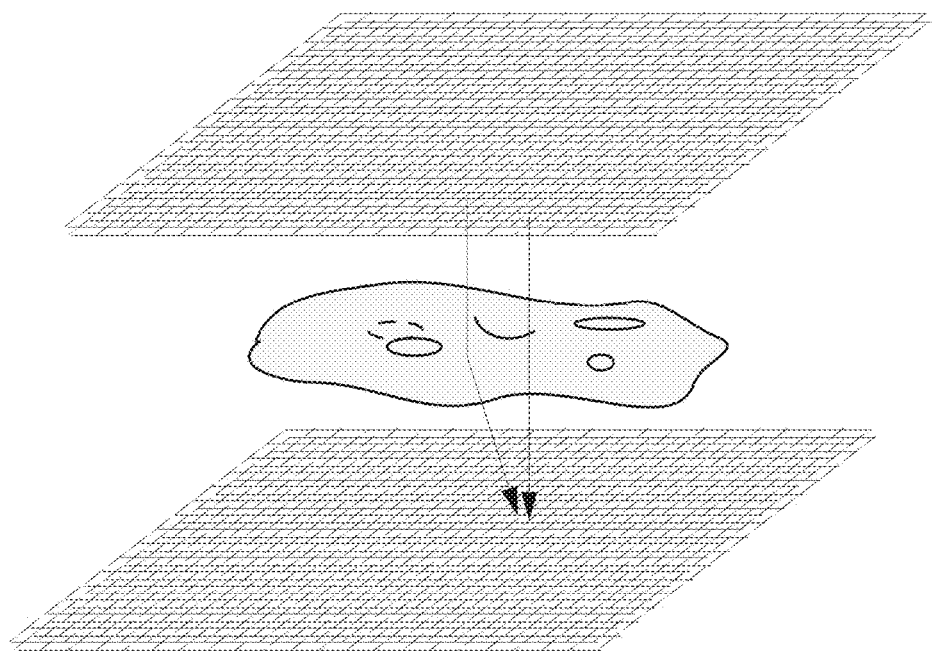
FIG. 19 depicts a larger scale view of the situation depicted in FIG. 18 wherein the planar illumination surface is an array of light-emitting elements and areas of both the planar illumination array and the image sensor array are depicted.

To address this, FIG. 18 depicts an adaptation of the situation depicted in FIG. 17 wherein the planar illumination surface comprises individual light-emitting pixels, one which serves as the first area of the planar illumination surface and the other of which serves as the second area of the planar illumination surface. Such a pixilated light-emitting planar illumination surface, if configured so that each light-emitting pixel could be sequenced on and off independently, can be used to create sequenced interpretation of the light measured at the image sensing pixel, distinguishing a straight light path from each of the many possible bent light paths. (It is noted that some light from the straight light path may diffuse, reflect, and/or refract within or from various constituents of the micro-organism or microscopic object and still end up incident on the same image sensing pixel as the straight path does). FIG. 19 depicts a larger scale view of the situation depicted in FIG. 18 wherein the planar illumination surface is an array of light-emitting elements and areas of both the planar illumination array and the image sensor array are depicted. The high-density array of light-emitting elements may comprise light-emitting diodes (LEDs), thin-film/printed organic light-emitting diodes (OLEDs), thin-film/printed organic light-emitting transistors (OLETs), etc. In various implementations the resolutions and spatial layout of the array of light-emitting elements may match, exceed, or be less than that of the image sensor pixel array as may be advantageous for reasons of function, cost, performance, etc. Further, the high-density array of light-emitting elements may comprise light-emitting elements of various wavelengths as may be advantageous in producing traditional optical color images and/or special scientific images. For example, should the microorganisms be provided with fluorescent markers prior to or within the flow microscope, ultraviolet wavelengths can be included (noting that ultraviolet LEDs are currently commercially available from manufacturers such as SET Inc., Photon Systems, etc.).

It is also noted that LEDs behave as (wavelength sensitive) photodiodes. Thus, an LED array can be used as an image sensing array. Additionally, individual elements in an LED array can be switched between idle mode, light-emitting mode, and light sensing mode. Such an arrangement, if used as an image sensor, can be sequentially operated to produce reflected-light contact imaging. In an implementation, the illuminating LED array is used both as a sequentially scanned light source and, via sequencing and/or multiplexing, as a reflective-imaging light sensor.

The parallel surfaces depicted in FIG. 15 (and carrying through in subsequent discussion) are LED arrays.

Figure 20:
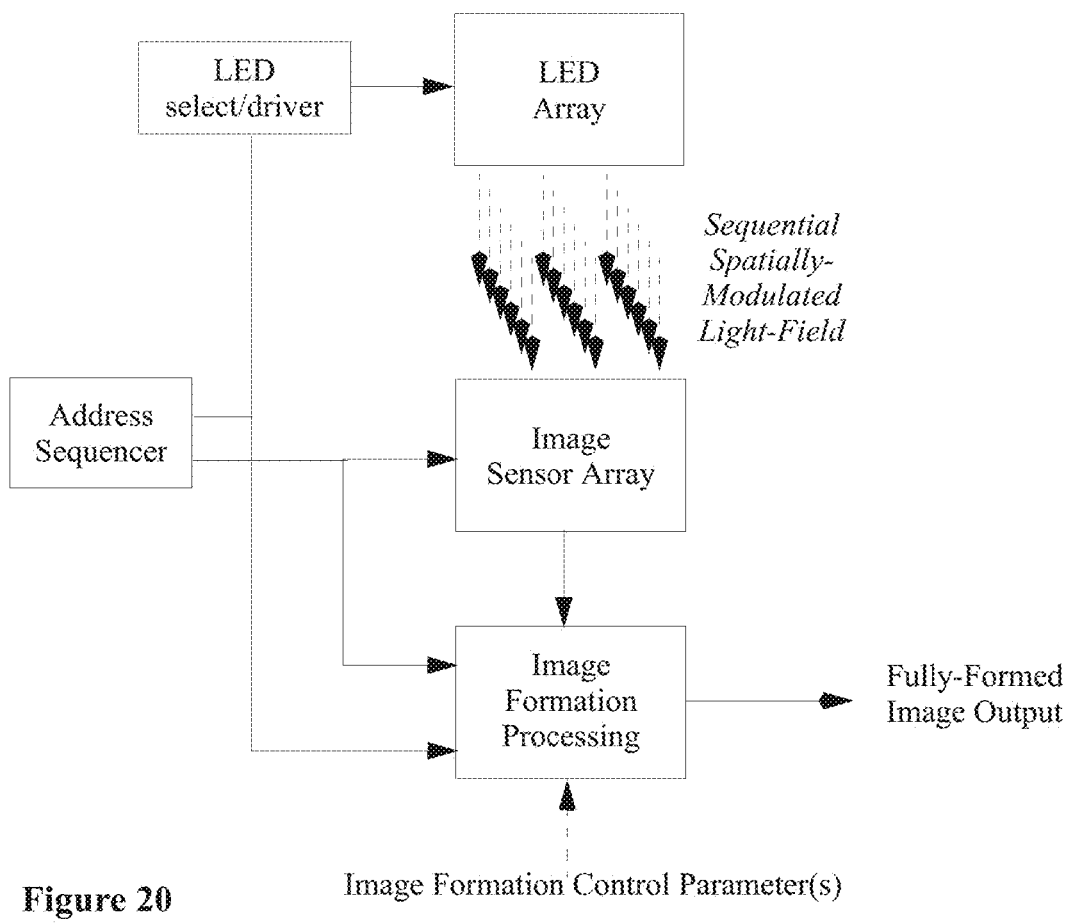
FIG. 20 depicts an exemplary embodiment of a synthetic image formation system employing the optical arrangement depicted in FIG. 19, the embodiment providing a fully-formed image output.
Figure 21:
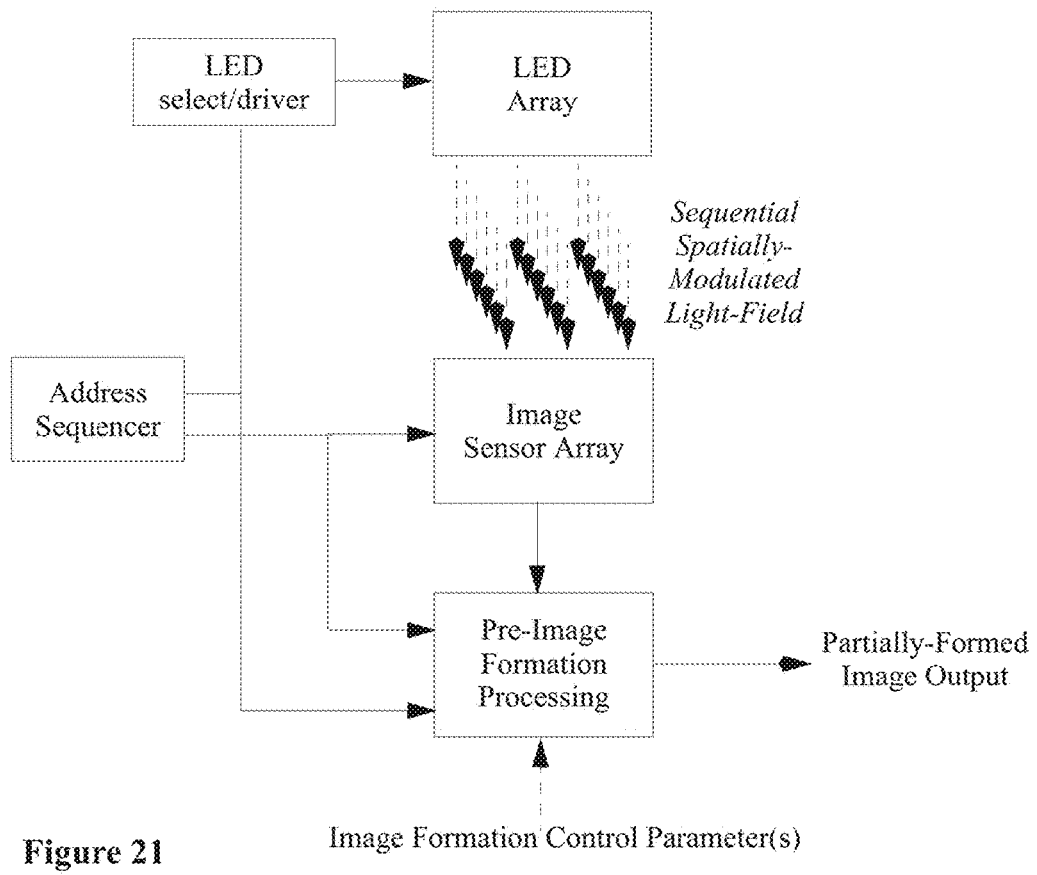
FIG. 21 depicts an exemplary embodiment of a synthetic image formation system employing the optical arrangement depicted in FIG. 19, the embodiment providing a partially-formed image output.
Figure 22:
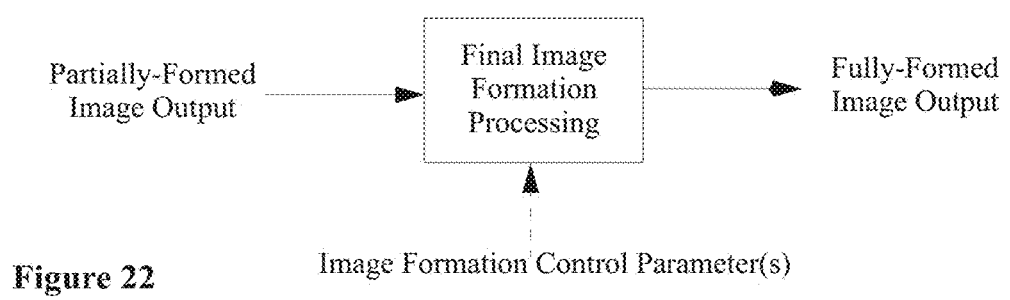
FIG. 22 depicts an exemplary arrangement wherein the partially-formed image output provided by an embodiment such as the exemplary depicted in FIG. 21 is further processed in a subsequent processing step by another processor so as to provide a fully-formed image output.

Referring to the arrangements described in at least terms of FIGS. 20-22, of particular interest is that by combining the temporal sequencing of individual light-emitting pixels with measurements at the optical sensor, the arrangements described above provide:

A means for obtaining a reasonably clear "traditional" optical transmission microscope type of image; and, even more interestingly The data measurement framework with which to implement various types of computed optical tomography.

The first-listed item well-serves the aforementioned applications in environmental science and bioreactor monitoring. The second—list item, i.e. the ability to perform a range of various types of computed optical tomography, provides a wide range of additional potential applications.

FIG. 20 depicts a synthetic image formation system employing the optical arrangement depicted in FIG. 19. In principle the arrangement may be used for traditional optical transmission microscope imaging as well as at least some forms of computed tomography imaging. This arrangement provides a fully-formed image output. Depending on the performance of various components, the system can produce individual or sequences of still images or live video-rate image streams.

Alternatively, FIG. 21 depicts a synthetic image formation system employing the optical arrangement of FIG. 19, and provides a partially-formed image output. FIG. 22 depicts an arrangement wherein the partially-formed image output provided is further processed in a subsequent processing step of another processor to provide a fully-formed image output.

Exemplary Electronic, Signal, and Power Implementations

Figure 23:
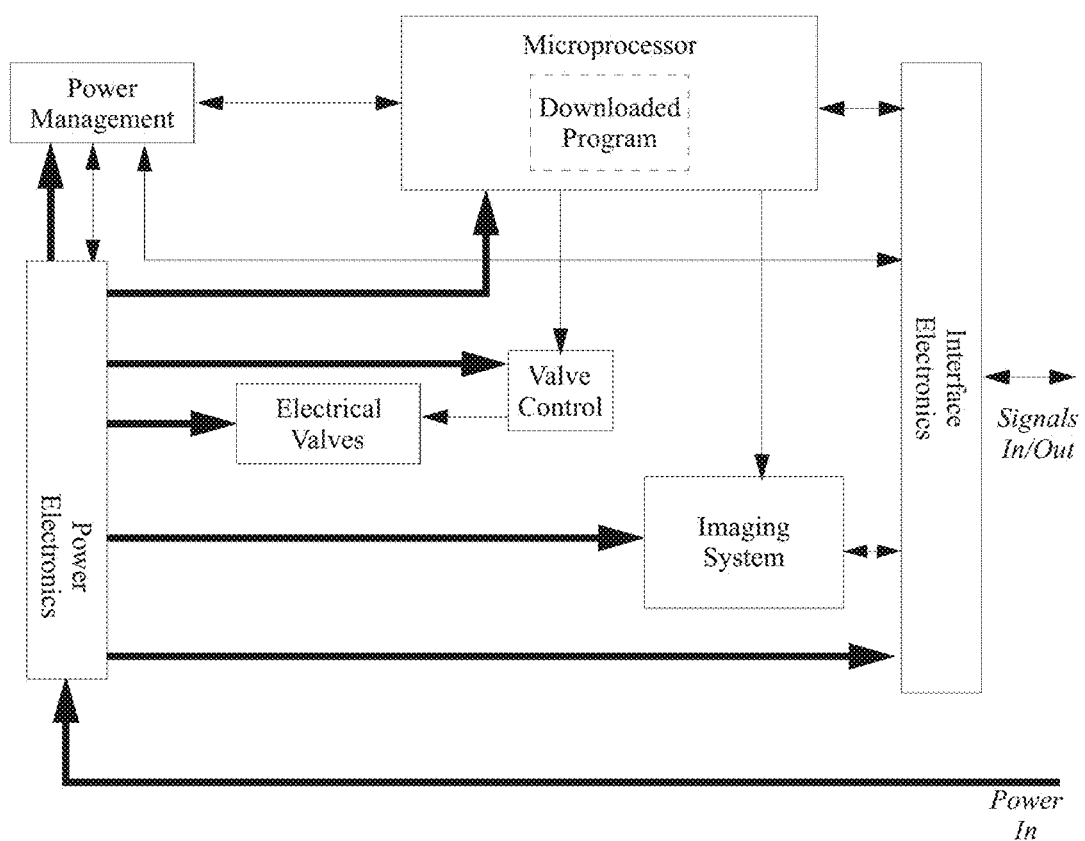
FIG. 23 depicts an exemplary embodiment of the internal elements, signal flows, and power flows for the invention.

FIG. 23 depicts the internal elements, signal flows, and power flows for the invention. Particularly in deployed environmental monitoring situations, power usage and management can be critical. Valves may be impulse-actuated or motor-actuated (rather than constant-duty solenoid) to limit power consumption.

In a deployment, solar power may be used to charge batteries or high-Faraday capacitors for use in power management for the flow microscope and/or associated technologies such as telemetry transmitters, transceivers, transponders, recording devices, beacons, associated sensor devices, etc.

A vane or turbine pump in the observed fluid flow path in the flow microscope device may be used as a generator for energy harvesting from water current flows through the device.

A parallel flow path through the flow microscope device may be used to operate a dedicated electrical generator for energy harvesting from water current flows through the device.

Figure 24:
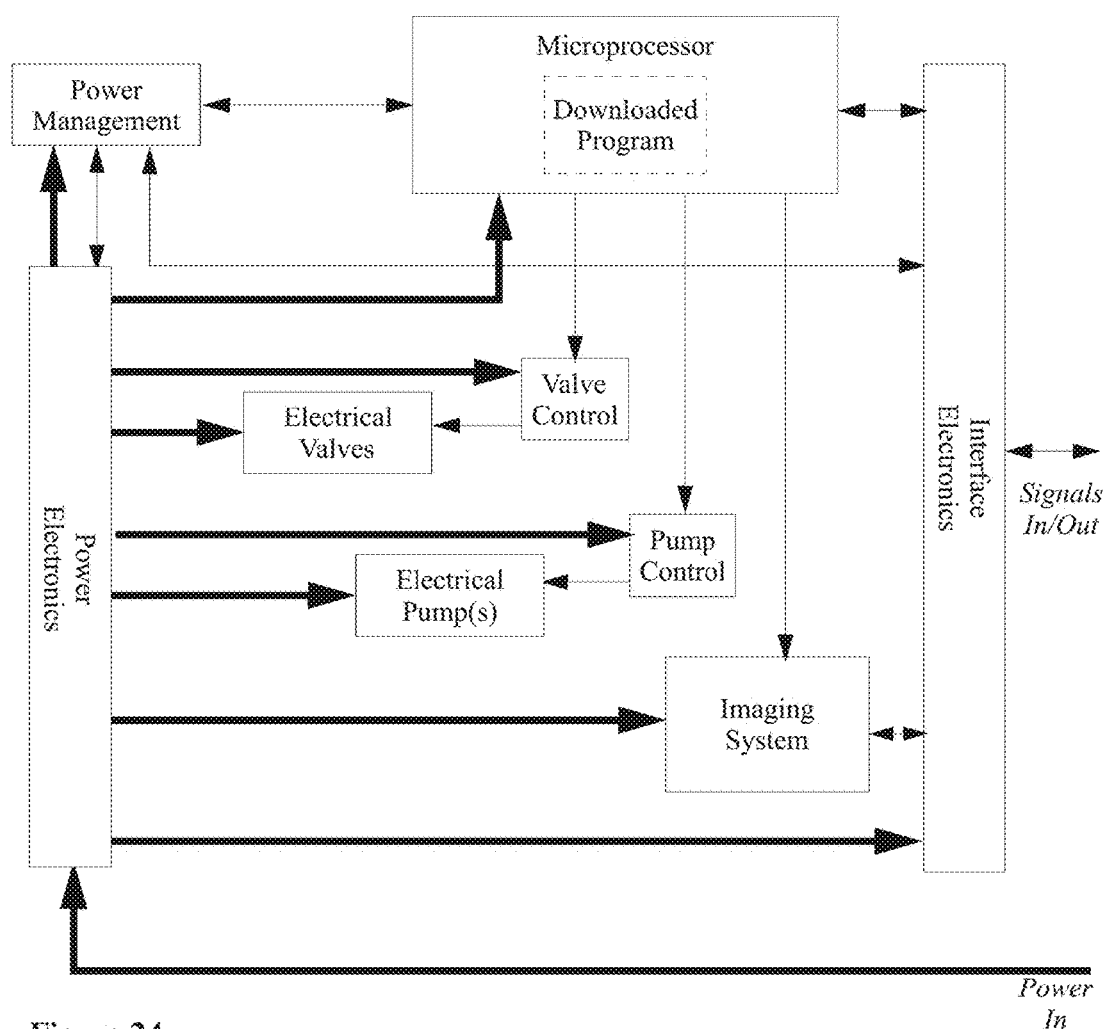
FIG. 24 depicts an augmentation to that depicted in FIG. 23 wherein controlled pumps are added.
Figure 25:
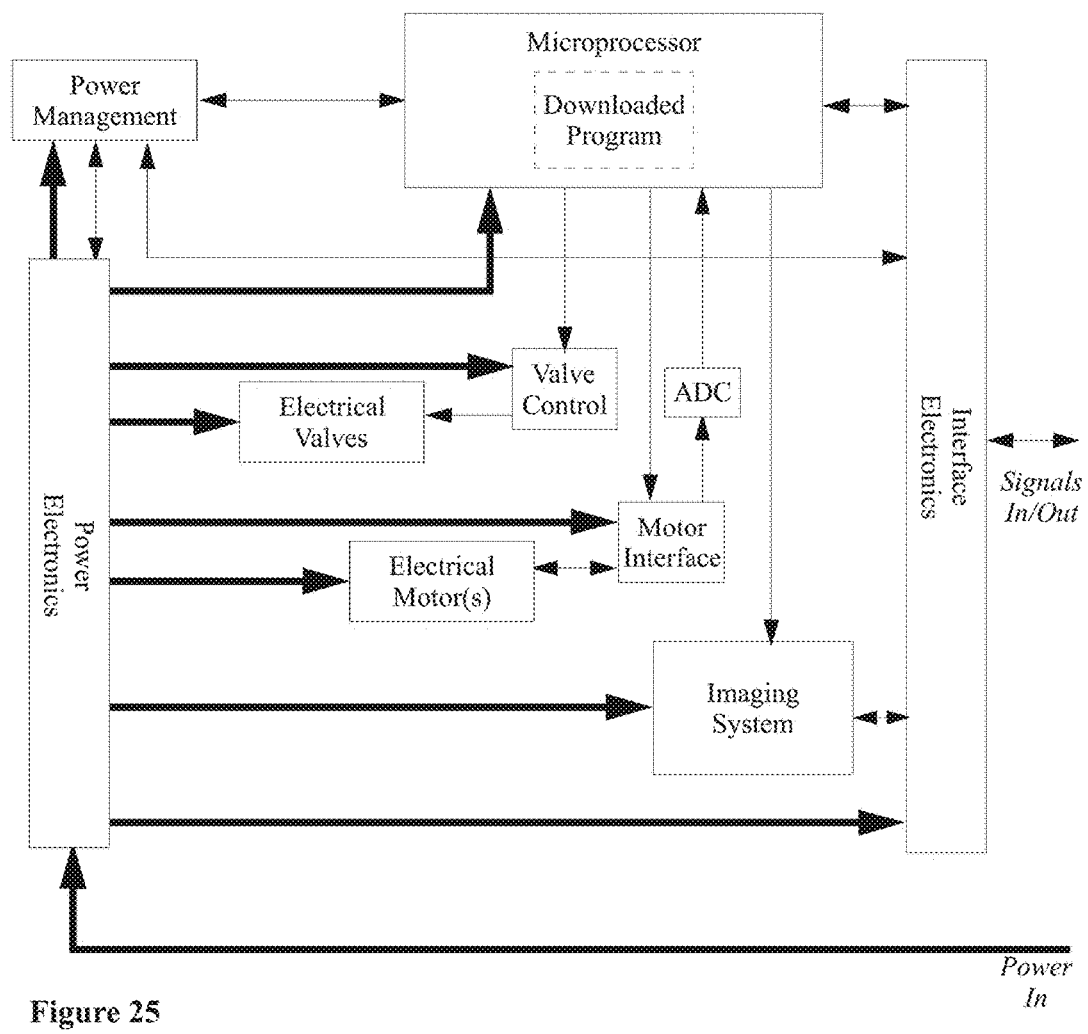
FIG. 25 depicts an augmentation to that depicted in FIG. 23 wherein controlled motors are added and analog signals relating to motor operation are processed by an Analog-to-Digital converter and forwarded to the microprocessor.
Figure 26:
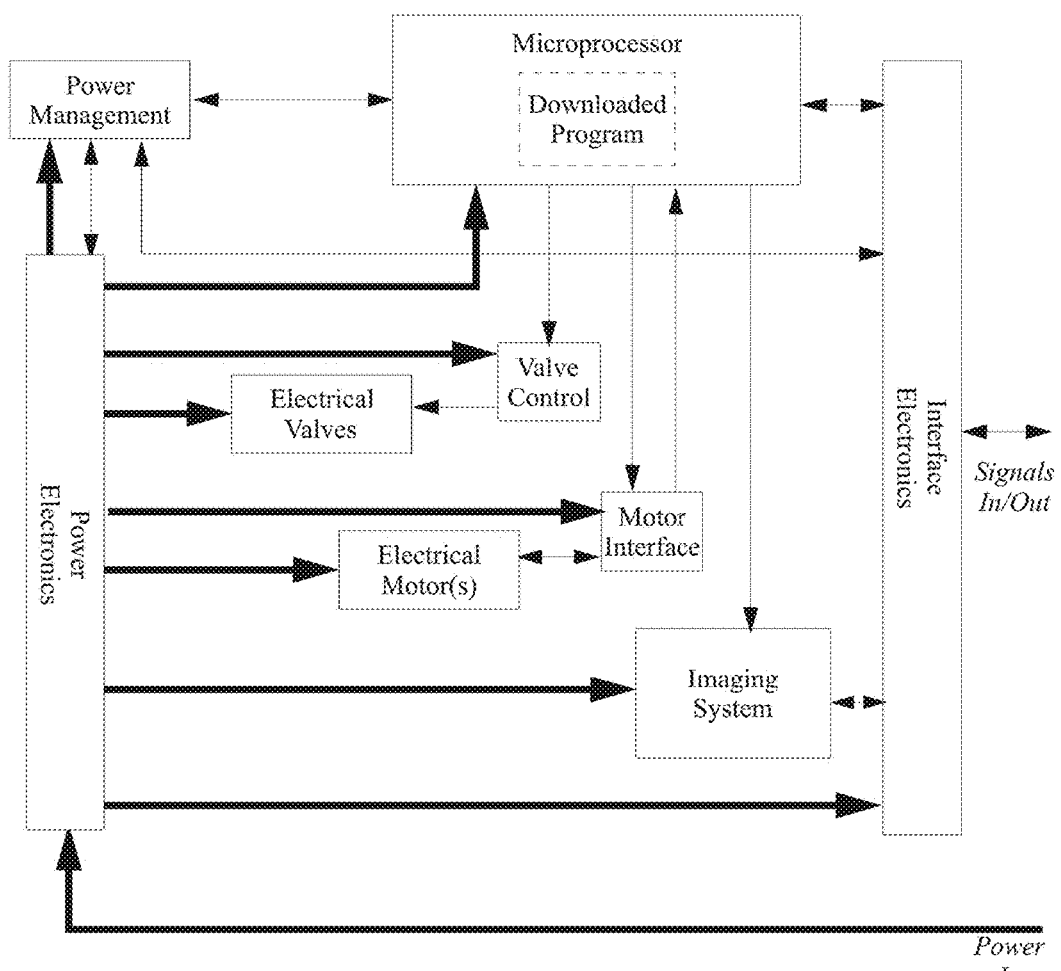
FIG. 26 depicts an augmentation to that depicted in FIG. 23 wherein controlled motors are added and signals relating to motor operation are directly forwarded to the microprocessor; depending on implementation, the signals relating to motor operation may be analog, digital, or both.

FIG. 24 depicts an augmentation to that depicted in FIG. 23 wherein controlled pumps are added. FIG. 25 depicts an augmentation to that depicted in FIG. 23 wherein controlled motors are added and analog signals relating to motor operation are processed by an Analog-to-Digital converter and forwarded to the microprocessor. Each such motor can be a pump motor. Such a pump motor can be monitored during motor operation (for example, monitoring measured operating current) or during idle operation (to serve as a flow meter) and/or in power harvesting motor (to monitor energy generated). FIG. 26 depicts an augmentation to that depicted in FIG. 23 wherein controlled motors are added and signals relating to motor operation are directly forwarded to the microprocessor; depending on implementation, the signals relating to motor operation may be analog, digital, or both. Should the signals be analog, the microprocessor may be of a mixed-signal type (such as a low-power 8051 mixed-signal microprocessor). Examples of digital signal that could be provided include rotation counters, temperature sensor chips, etc.

While the invention has been described in detail with reference to disclosed embodiments, various modifications within the scope of the invention will be apparent to those of ordinary skill in this technological field. It is to be appreciated that features described with respect to one embodiment typically can be applied to other embodiments.

The invention can be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. Therefore, the invention properly is to be construed with reference to the claims.

In the following description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention.

In the following description, numerous specific details are set forth to provide a thorough description of various embodiments. Certain embodiments may be practiced without these specific details or with some variations in detail. In some instances, certain features are described in less detail so as not to obscure other aspects. The level of detail associated with each of the elements or features should not be construed to qualify the novelty or importance of one feature over the others.

1. Light Sourcing and Light Sensing

Figure 27:
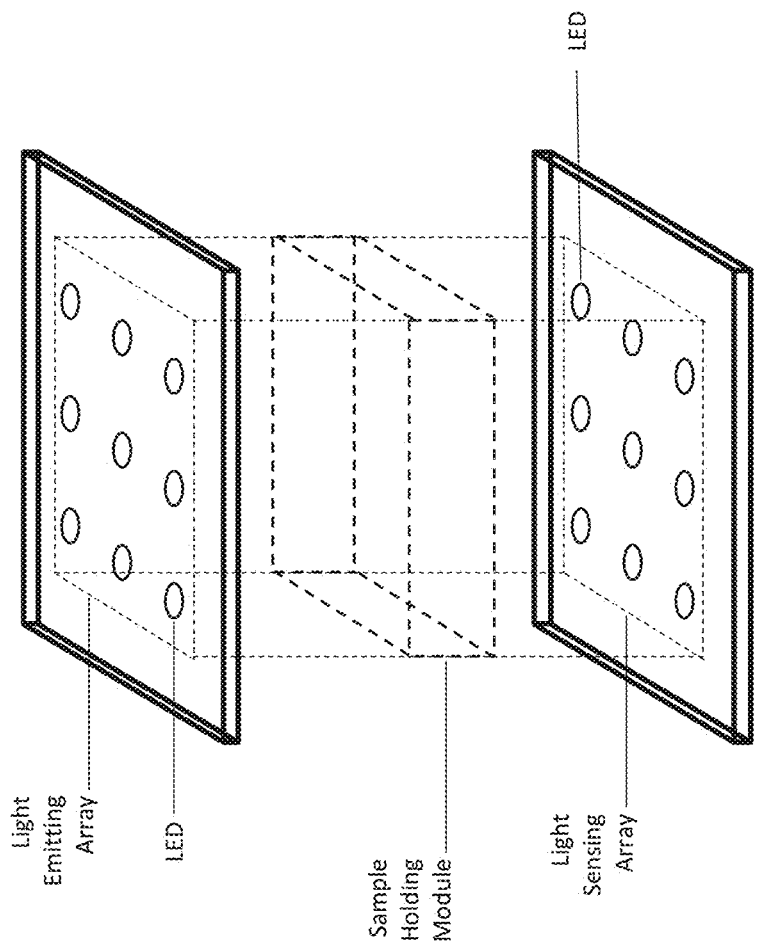
FIG. 27 shows an example embodiment of a planar light emitting and light sensing arrangement in an optical tomography system.

FIG. 27 shows an example embodiment of a planar light emitting and light sensing arrangement in an optical tomography system, depicting various elements of the system such as light emitting and light sensing arrays, each comprised of LEDs, and a holding module. FIG. 27 is illustrative in its depiction of an embodiment of the present invention but not restrictive.

Light sourcing or emitting and light sensing arrangements of the present invention can be an array of light emitting (light emitter) or light sensing (light sensor) elements. In an example embodiment, as shown in FIG. 27, a planar 2-dimensional light sensing or light sensor array and a planar 2-dimensional light emitting or light emission array face each other in a parallel arrangement configured so each sensor in the light sensor plane can receive light emitted by at least one light emitter or light emitting element in the light emitter plane. In a planar arrangement, the light emitting and light sensing arrays have n by n or $n^2$ LEDs and there will be at most $n^4$ light paths because each light path is defined by a pairing of light emitting and light sensing LEDs and there are $n^2 \times n^2 = n^4$ possible pairings of light emitting to light sensing LEDs. The quantity and arrangement of light emitting and light sensing elements can vary depending on the geometric arrangement.

1.1 Light Sourcing and Light Sensing Technologies

Light emitting and light sensing elements may comprise light-emitting diodes (LEDs), thin-film/printed organic light-emitting diodes (OLEDs), thin-film/printed organic light-emitting transistors (OLETs), etc. In various implementations the resolutions and spatial layout of the array of light-emitting elements may match, exceed, or be less than that of the image sensor pixel array as may be advantageous for reasons of function, cost, performance, etc. Further, the high-density array of light-emitting elements may comprise light-emitting elements of various wavelengths as may be advantageous in producing traditional optical color images and/or special scientific images, i.e., ultraviolet LEDs. It is also noted that LEDs behave as (wavelength sensitive) photodiodes. Thus, an LED array can be used as an image sensing array. Additionally, individual elements in an LED array can be switched between inactive (or idle) mode, light-emitting mode, and light-sensing mode.

Figure 28:
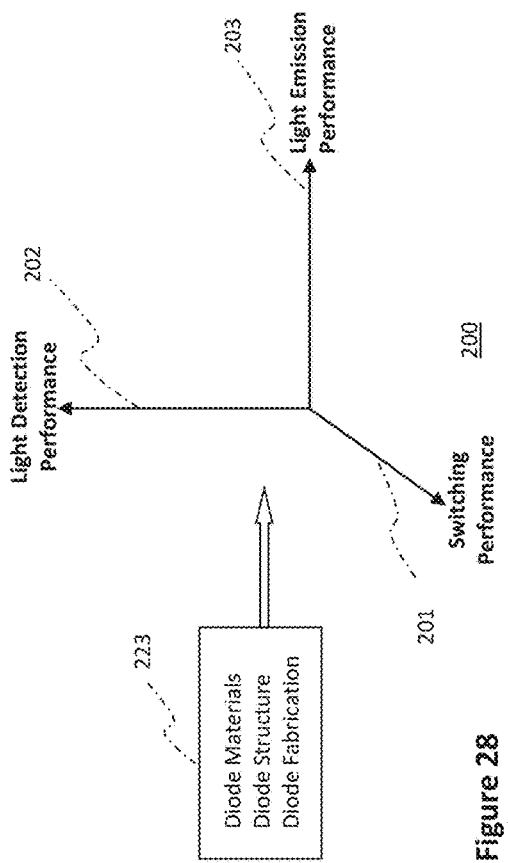
FIG. 28 depicts an optimization space for semiconductor diodes comprising attributes of signal switching performance, light emitting performance, and light detection performance.
Figure 29:
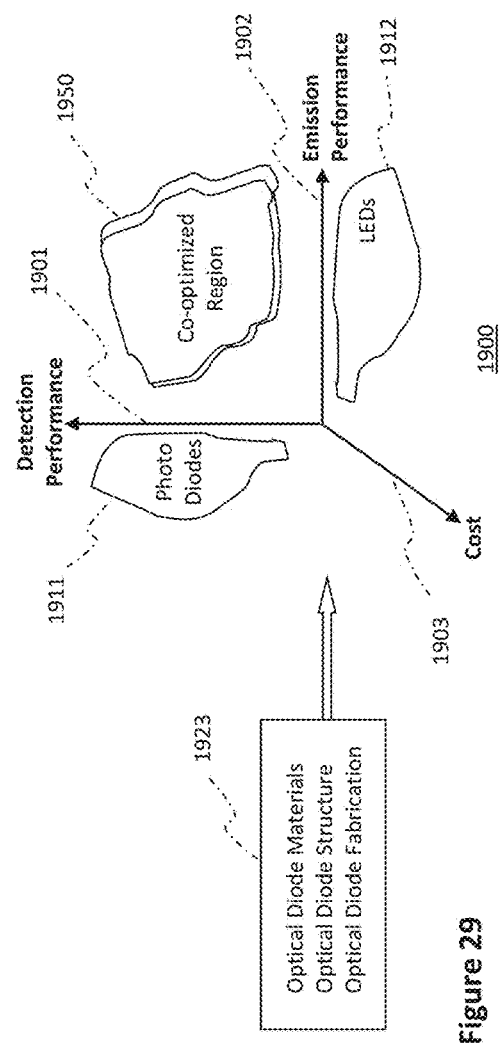
FIG. 29 depicts an exemplary metric space of device realizations for optoelectronic devices and regions of optimization and co-optimization.

Such an arrangement, if used as an image sensor, can be sequentially operated to produce reflected-light contact imaging. In an implementation, the illuminating LED array is used both as a sequentially scanned light source and, via sequencing and/or multiplexing, as a reflective-imaging light sensor. High resolution sensors or organic light sensors that are not LEDs especially in planar geometry arrangement may also be implemented in certain embodiments of the present invention. In some embodiments, LEDs with both emitting and sensing properties require co-optimizing of both sets of properties. In other embodiments, LEDs with strictly emitting properties or LEDs with strictly detecting properties might be advantageous to optimize performance. For example, as illustrated in pending U.S. patent application Ser. No. 13/180,345, FIG. 28 depicts an optimization space for semiconductor diodes comprising attributes of signal switching performance, light emitting performance, and light detection performance. Specific diode materials, diode structure, and diode fabrication approaches can be adjusted to optimize a resultant diode for switching function performance (for example, via use of abrupt junctions), light detection performance such as via a P-I-N structure comprising a layer of intrinsic semiconducting material between regions of n-type and p-type material, or light detection performance. FIG. 29 depicts an exemplary metric space of device realizations for optoelectronic devices and regions of optimization and co-optimization. Specific optoelectrical diode materials, structure, and fabrication approaches can be adjusted to optimize a resultant optoelectrical diode for light detection performance such as via a P-I-N structure comprising a layer of intrinsic semiconducting material between regions of n-type and p-type material versus light emission performance versus cost Optimization within the plane defined by light detection performance and cost traditionally result in photodiodes while optimization within the plane defined by light emission performance and cost traditionally result in LEDs. Specific optoelectrical diode materials, structure, and fabrication approaches can be adjusted to co-optimize an optoelectrical diode for both good light detection performance and light emission performance versus cost. A resulting co-optimized optoelectrical diode can be used for multiplexed light emission and light detection modes. These permit a number of applications of the present invention.

FIG. 30*a* shows an example schematic diagram of a light-emitting LED. In contrast to FIG. 30*a*, FIG. 30*b* shows an example schematic diagram of a light-sensing LED in a reverse-bias arrangement. FIG. 30*c* shows an example schematic diagram of a light-sensing LED measuring decay time. Pending U.S. patent application Ser. No. 13/180,345 illustrates that light sensing is typically performed by photosite CCD (charge-coupled device) elements, phototransistors, CMOS photodetectors, and photodiodes. Photodiodes are often viewed as the simplest and most primitive of these, and typically comprise a PIN (P-type/Intrinsic/N-type) junction rather than the more abrupt PIN (P-type/N-type) junction of conventional signal and rectifying diodes. However, virtually all diodes are capable of photovoltaic properties to some extent. In particular, LEDs, which are diodes that have been structured and doped specific types of optimized light emission, can also behave as (at least low-to moderate performance) photodiodes. Each LED in an array of LEDs can be alternately used as a photodetector or as a light emitter. At any one time, each individual LED would be in one of three states, a light emission mode, a light detection mode, or an inactive (or idle) mode as may be advantageous for various operating strategies. The state transitions of each LED may be coordinated in a wide variety of ways to afford various multiplexing, signal distribution, and signal gathering schemes as may be advantageous.

1.2 Multiplexing

A variety of methods can be implemented for the multiplexing circuitry for LED arrays utilized in the present invention. As illustrated in pending U.S. patent application Ser. No. 13/180,345, for rectangular arrays of LEDs, it is typically useful to interconnect each LED with access wiring arranged to be part of a corresponding matrix wiring arrangement. The matrix wiring arrangement is time-division multiplexed. Such time-division multiplexed arrangements can be used for delivering voltages and currents to selectively illuminate each individual LED at a specific intensity level (including very low or zero values so as to not illuminate).

Figure 31:
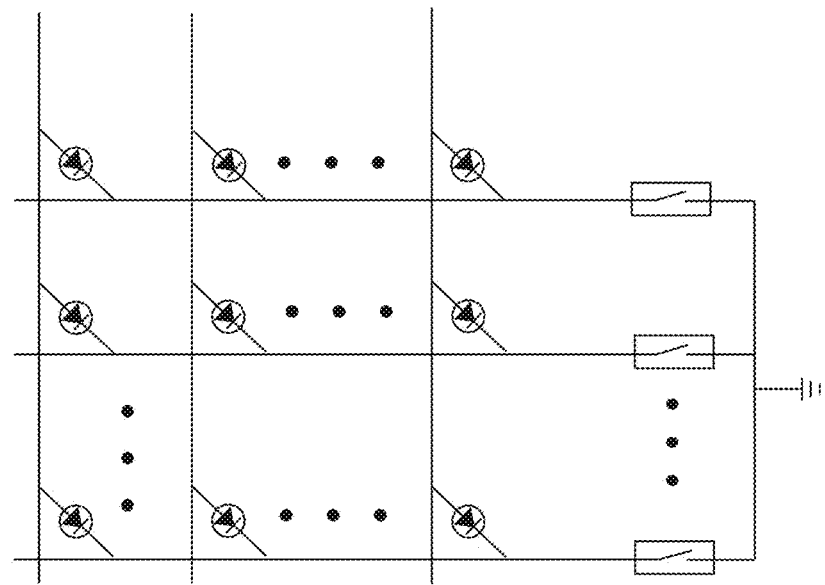
FIG. 31 depicts an example multiplexing arrangement for a two-dimensional array of LEDs.

An example multiplexing arrangement for a two-dimensional array of LEDs is depicted in FIG. 31. Here each of a plurality of normally-open analog switches are sequentially closed for brief disjointed intervals of time. This allows the selection of a particular subset (here, a column) of LEDs to be grounded while leaving all other LEDs in the array not connected to ground. Each of the horizontal lines then can be used to connect to exactly one grounded LED at a time. The plurality of normally-open analog switches in FIG. 31 may be controlled by an address decoder so that the selected subset can be associated with a unique binary address, as suggested in FIG. 32. The combination of the plurality of normally-open analog switches together with the address decoder form an analog line selector. By connecting the line decoder's address decoder input to a counter, the columns of the LED array can be sequentially scanned.

Figure 32:
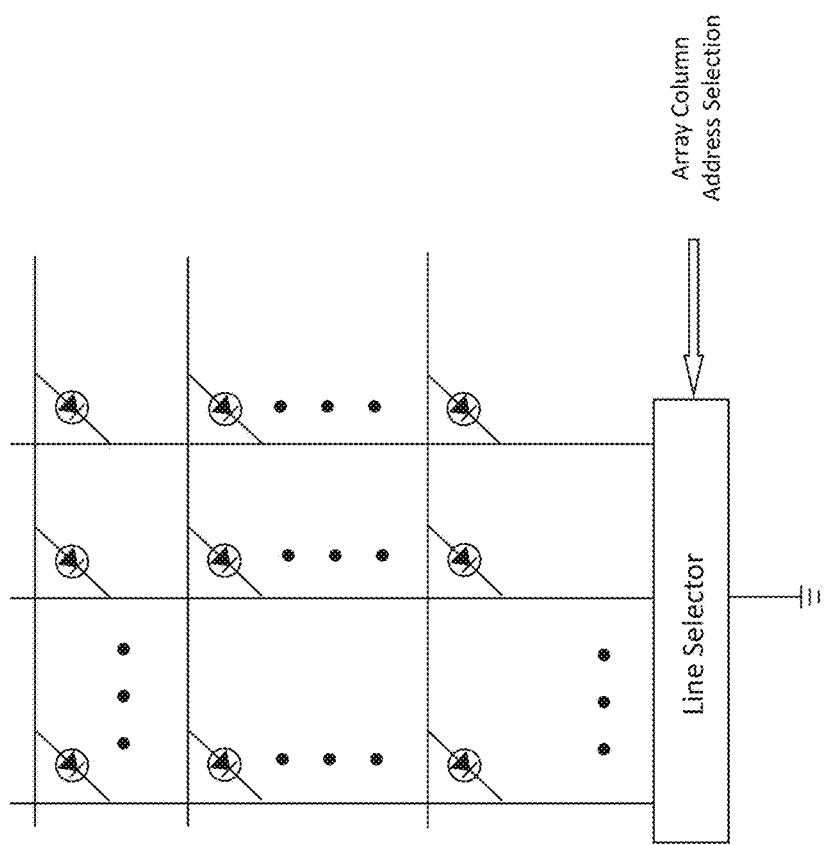
FIG. 32 depicts an adaptation of the arrangement depicted in FIG. 31 that is controlled by an address decoder so that the selected subset can be associated with a unique binary address.
Figure 33:
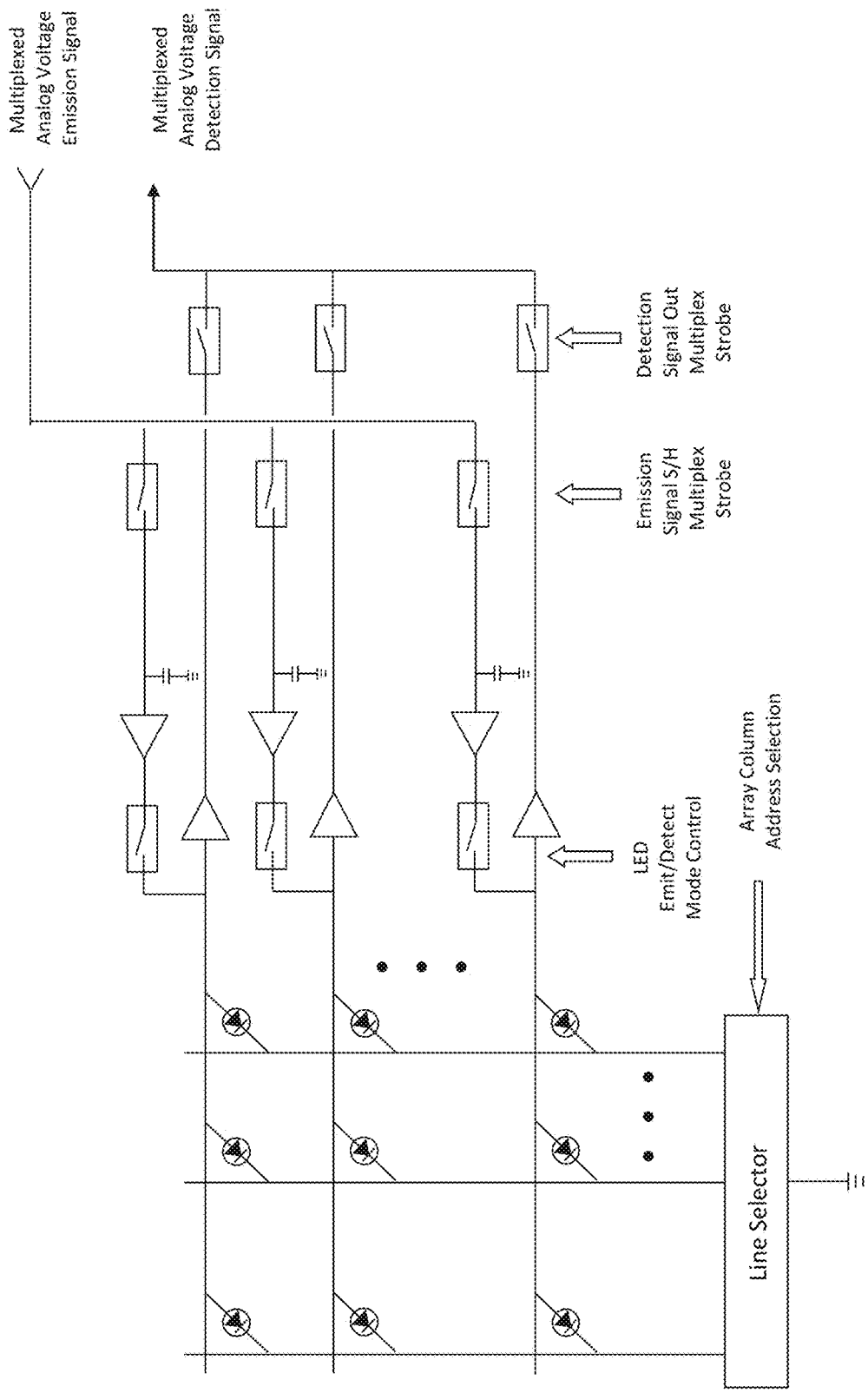
FIG. 33 depicts an exemplary adaptation of the arrangement of FIG. 32 together to form a highly scalable LED array display that also functions as a light field detector.

FIG. 33 depicts an exemplary adaptation of the arrangement of FIG. 32 together to form a highly scalable LED array display that also functions as a light field detector. The various multiplexing switches in this arrangement can be synchronized with the line selector and mode control signal so that each LED very briefly provides periodically updated detection measurement and is free to emit light the rest of the time. A wide range of variations and other possible implementations are possible and implemented in various embodiments of the present invention.

Figure 34:
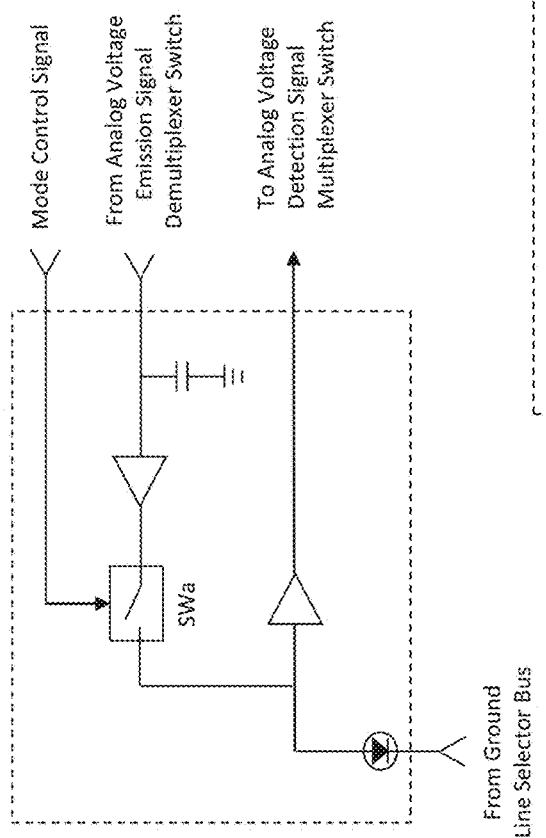
FIGS. 34 and 35 depict exemplary functional cells that may be used in a large scale array.
Figure 35:
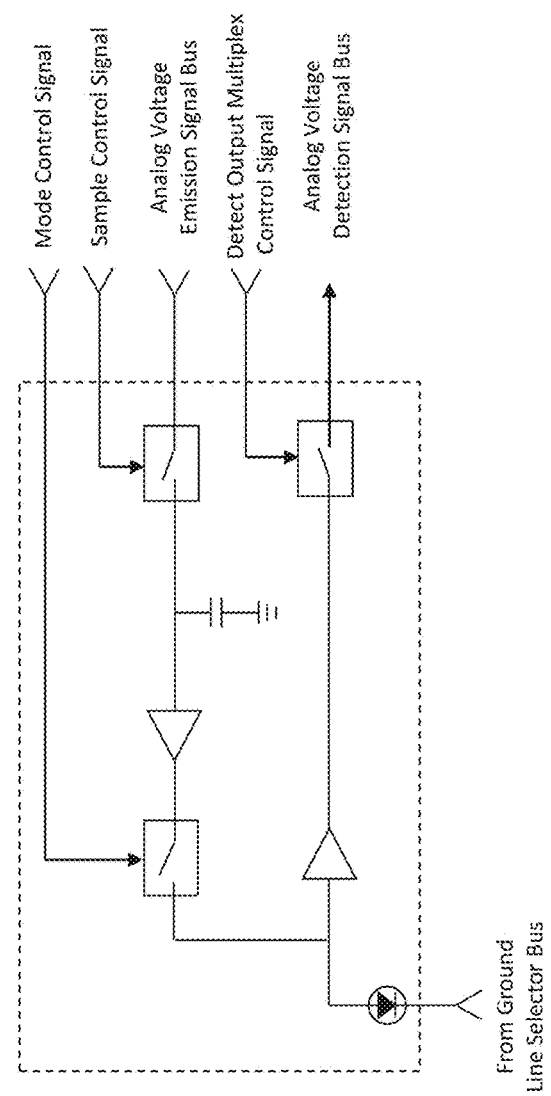

Such time-division multiplexed arrangements can alternatively be used for selectively measuring voltages or currents of each individual LED. Further, the illumination and measurement time-division multiplexed arrangements themselves can be time-division multiplexed, interleaved, or merged in various ways. As an illustrative example, the arrangement of FIG. 33 can be reorganized so that the LED, mode control switch, capacitor, and amplifiers are collocated, for example as in the illustrative exemplary arrangement of FIG. 34. Such an arrangement can be implemented with, for example, three MOSFET switching transistor configurations, two MOSFET amplifying transistor configurations, a small-area/small-volume capacitor, and an LED element (that is, five transistors, a small capacitor, and an LED). This can be treated as a cell which is interconnected to multiplexing switches and control logic. A wide range of variations and other possible implementations are possible and the example of FIG. 33 is in no way limiting. For example, the arrangement of FIG. 33 can be reorganized to decentralize the multiplexing structures so that the LED, mode control switch, multiplexing and sample/hold switches, capacitor, and amplifiers are collocated, for example as in the illustrative exemplary arrangement of FIG. 35. Such an arrangement can be implemented with, for example, three MOSFET switching transistor configurations, two MOSFET amplifying transistor configurations, a small-area/small-volume capacitor, and an LED element (that is, five transistors, a small capacitor, and an LED). This can be treated as a cell whose analog signals are directly interconnected to busses. Other arrangements are also possible.

The discussion and development thus far are based on the analog circuit measurement and display arrangement of FIG. 36 that in turn leverages the photovoltaic properties of LEDs. With minor modifications clear to one skilled in the art, the discussion and development thus far can be modified to operate based on the analog circuit measurement and display arrangements of FIG. 37 and FIG. 38 that leverage the photocurrrent properties of LEDs.

Figure 41:
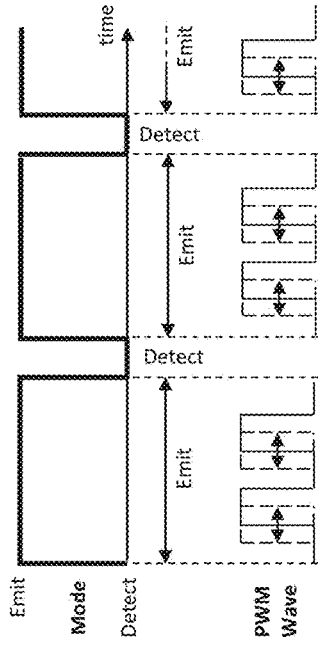
FIGS. 40-42 depict adaptations of the digital circuit measurement and display arrangements into an example combination.
Figure 42:
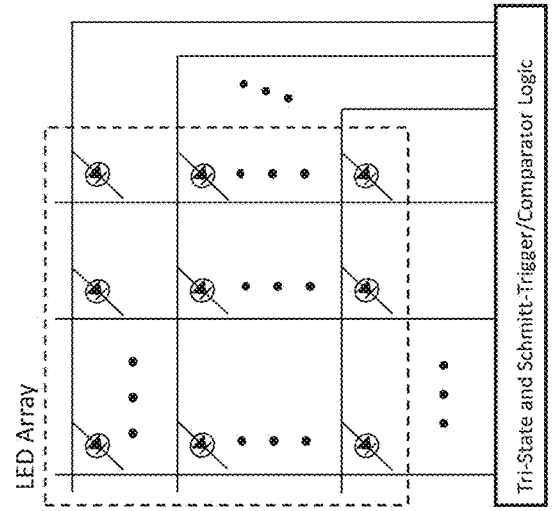
Figure 40:
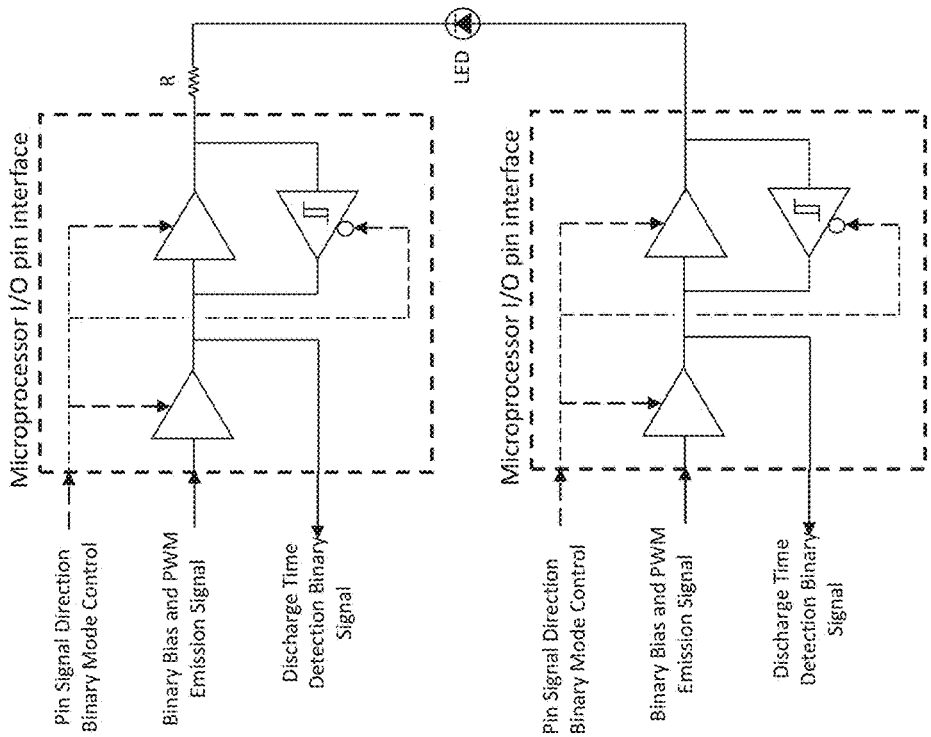

FIG. 40, FIG. 41, and FIG. 42 depict an example of how the digital circuit measurement and display arrangement of FIG. 39 (that in turn leverages discharge times for accumulations of photo-induced charge in the junction capacitance of the LED) can be adapted into the construction developed thus far. FIG. 40 adapts FIG. 39 to additional include provisions for illuminating the LED with a pulse-modulated emission signal. Noting that the detection process described earlier in conjunction with FIG. 39 can be confined to unperceivably short intervals of time, FIG. 41 illustrates how a pulse-width modulated binary signal may be generated during LED illumination intervals to vary LED emitted light brightness. FIG. 42 illustrates an adaptation of the tri-state and Schmitt-trigger/comparator logic akin to that illustrated in the microprocessor I/O pin interface that may be used to sequentially access subsets of LEDs in an LED array as described in conjunction with FIG. 31 and FIG. 32.

FIGS. 43-45 depict exemplary state diagrams for the operation of the LED and the use of input signals and output signals described above. From the viewpoint of the binary mode control signal there are only two states: a detection state and an emission state, as suggested in FIG. 43. From the viewpoint of the role of the LED in a larger system incorporating a multiplexed circuit arrangement such as that of FIG. 33, there may a detection state, an emission state, and an idle state (where there is no emission nor detection occurring), obeying state transition maps such as depicted in FIG. 44 or FIG. 45. At a further level of detail, there are additional considerations. To emit light, a binary mode control signal can be set to "emit" mode (causing the analog switch to be closed) and the emission light signal must be of sufficient value to cause the LED to emit light (for example, so that the voltage across the LED is above the "turn-on" voltage for that LED). If the binary mode control signal is in "emit" mode but the emission light signal is not of such sufficient value, the LED will not illuminate. This can be useful for brightness control (via pulse-width modulation), black-screen display, and other uses. In some embodiments, this may be used to coordinate the light emission of neighboring LEDs in an array while a particular LED in the array is in detection mode. If the emission light signal of such sufficient value but the binary mode control signal is in "detect" mode, the LED will not illuminate responsive to the emission light signal. This allows the emission light signal to be varied during a time interval when there is no light emitted, a property useful for multiplexing arrangements. During a time interval beginning with the change of state of the binary mode control signal to some settling-time period afterwards, the detection output and/or light emission level may momentarily not be accurate. To detect light, the binary mode control signal must be in "detect" mode (causing the analog switch to be open). The detected light signal may be used by a subsequent system or ignored. Intervals where the circuit is in detection mode but the detection signal is ignored may be useful for multiplexing arrangement, in providing guard-intervals for settling time, to coordinate with the light emission of neighboring LEDs in an array, etc.

FIG. 46 depicts an exemplary state transition diagram reflecting the above considerations. The top "Emit Mode" box and bottom "Detect Mode" box reflect the states of an LED from the viewpoint of the binary mode control signal as suggested by FIG. 43. The two "Idle" states (one in each of the "Emit Mode" box and "Detect Mode" box) of FIG. 46 reflect (at least in part) the "Idle" state suggested in FIG. 44 and/or FIG. 45. Within the "Emit Mode" box, transitions between "Emit" and "Idle" may be controlled by emit signal multiplexing arrangements, algorithms for coordinating the light emission of an LED in an array while a neighboring LED in the array is in detection mode, etc. Within the "Detect Mode" box, transitions between "Detect" and "Idle" may be controlled by independent or coordinated multiplexing arrangements, algorithms for coordinating the light emission of an LED in an array while a neighboring LED in the array is in detection mode, etc. In making transitions between states in the boxes, the originating and termination states may be chosen in a manner advantageous for details of various multiplexing and feature embodiments. Transitions between the groups of states within the two boxes correspond to the vast impedance shift invoked by the switch opening and closing as driven by the binary mode control signal. In FIG. 46, the settling times between these two groups of states are gathered and regarded as a transitional state.

As mentioned earlier, the amplitude of light emitted by an LED can be modulated to lesser values by means of pulse-width modulation (PWM) of a binary waveform. For example, if the binary waveform oscillates between fully illuminated and non-illuminated values, the LED illumination amplitude will be perceived roughly as 50% of the full-on illumination level when the duty-cycle of the pulse is 50%, roughly as 75% of the full-on illumination level when the duty-cycle of the pulse is 75%, roughly as 10% of the full-on illumination level when the duty-cycle of the pulse is 10%, etc. Clearly the larger fraction of time the LED is illuminated (i.e., the larger the duty-cycle), the brighter the perceived light observed emitted from the LED.

It is further understood that depending on the embodiments of light sourcing and sensing arrangements of the present invention, various combinations and modifications of multiplexing circuitry can be implemented to achieve the desired result. It is further understood that such multiplexing circuitry can further be combined and modified to better utilize the properties of flexible materials onto which the light LEDs, OLEDs, etc. are printed.

1.3 Light Sourcing and Light Sensing Geometries

Figure 47B:
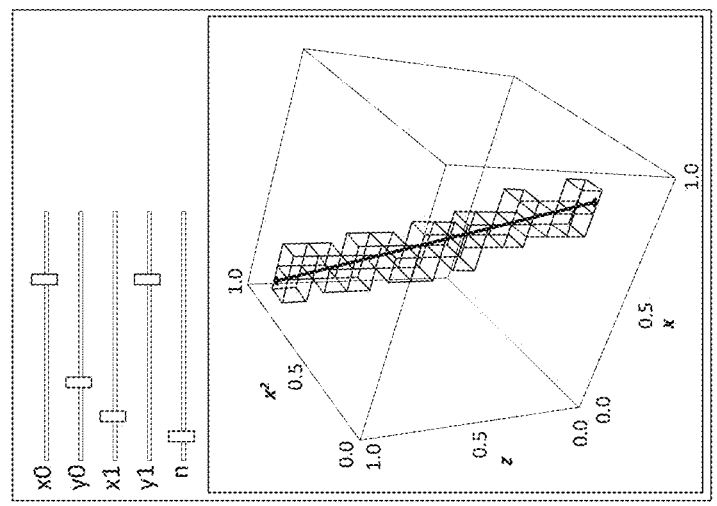
Figure 74A:
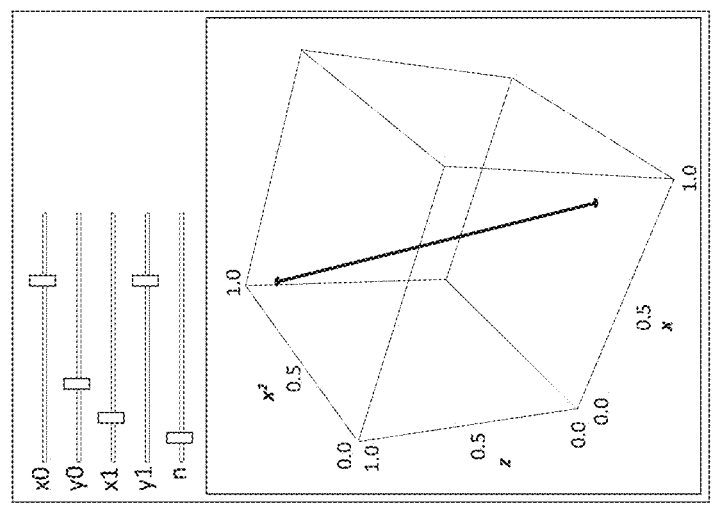
FIG. 74a depicts an exemplary graphical rendering in a visualizer module of a light path between a light emission plane and a light sensing plane in three-dimensional space.
Figure 75A:
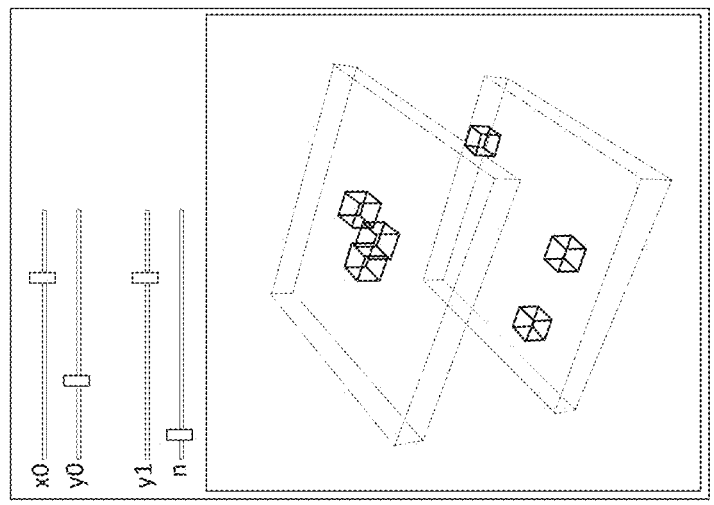
FIG. 75a depicts an exemplary graphical rendering in a visualizer module of discretized planes in a discretized space, shown with voxels activated by multiple light paths.
Figure 75B:
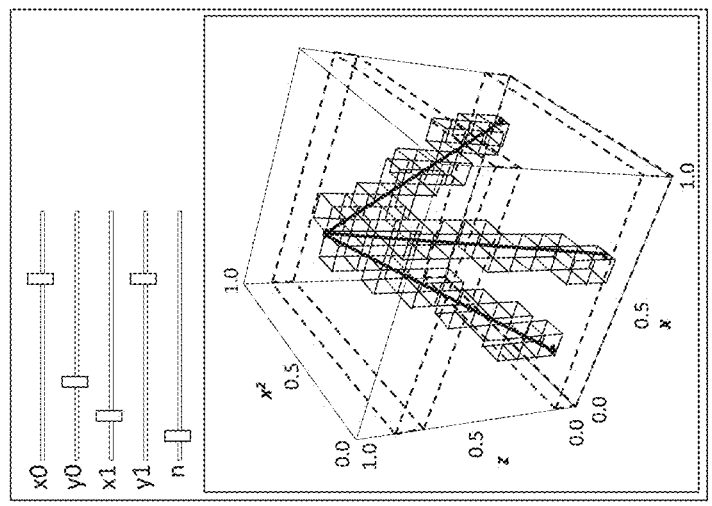
FIG. 75b depicts an exemplary graphical rendering in a visualizer module of a cross-sectional view of a voxel arrangement in a discretized space.

FIGS. 47a-47d shows exemplary geometries of light emitting and light sensing arrangements for various optical tomography systems. Various light emitting and light sensing arrangement geometries suitable for optical tomography include, but are not limited to planar, cylindrical, spherical, or warped (i.e., flexible). For example, FIG. 47a shows an example light emitting and light sensing arrangement with planar geometry. FIG. 47b shows an example light emitting and light sensing arrangement with cylindrical geometry. FIG. 47c shows an example light emitting and light sensing arrangement with spherical geometry. FIG. 47d shows an example light emitting and light sensing arrangement with warped, or flexible geometry. In certain embodiments, one plane or one half of the arrangement may act as a light sensing array and the other plane or half may act as a light emitting or light emission array, or both planes or both halves may have both light emitting and light sensing capabilities. Depending on the physical characteristics of the object or specimen, the medium in which the object is located, size, opacity, etc., various geometric arrangements may be advantageous and may be implemented in different embodiments of the present invention. It is also noted that in certain embodiments of the invention, flexible, printable materials can be used to achieve a variety of geometric arrangements of the present invention.

1.3 Discretization of 3-D Space in Measurement Volume

FIG. 48 shows an example embodiment of a discretized space between a planar light emitting and light sensing arrangement in an optical tomography system. In order to calculate the transparency of an object placed between a light emitting and light sensing arrangement with high resolution, a set of mathematical equations for processing can be generated. To generate mathematical equations, space between the light emitting and light sensing arrangement is discretized, such as into a plurality of cubes, or voxels, as depicted in FIG. 48, which shows an example embodiment of a discretized space between a planar light emitting and light sensing arrangement in an optical tomography system. These cubes act as 3D pixels, or voxels, and are interrogated to generate a full reconstruction of the object. Just as a camera captures a 2D image by interrogating and replicating the color of each pixel in the image, the present invention renders a 3D model of an object by interrogating and replicating the opacity of each voxel in the object.

Figure 49B:
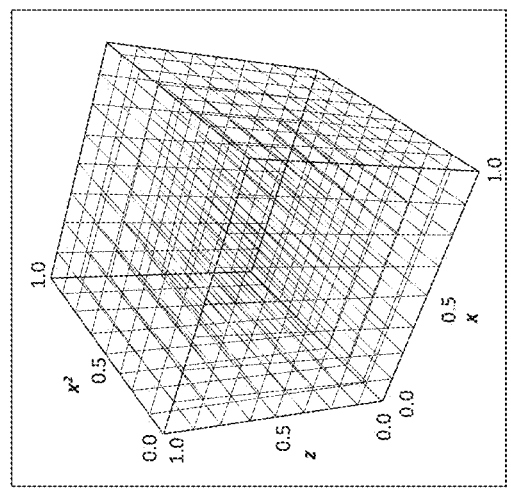
FIG. 49b shows an example of a discretized three-dimensional space between a planar light emitting and light sensing arrangement.
Figure 49A:
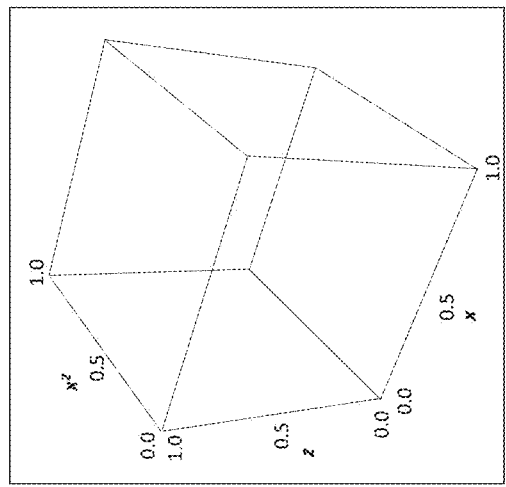
FIG. 49a shows an example of three-dimensional space between a planar light emitting and light sensing arrangement.

FIG. 49a shows an example of three-dimensional space between a planar light emitting and light sensing arrangement. FIG. 49b shows an example of a discretized three-dimensional space between a planar light emitting and light sensing arrangement. Generally, an increase in the discretization of the space into smaller units provides a more detailed calculation of the transparency of the object and hence, a higher resolution. The set of equations and associated computations will vary in complexity based on the geometry of the arrangement.

Figure 50C:
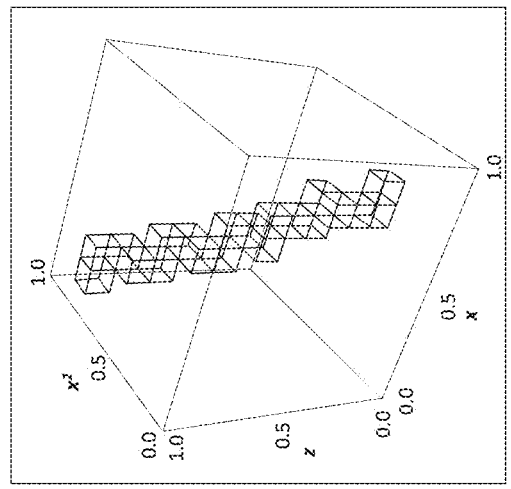
FIG. 50c further depicts an exemplary activation of discrete voxels intersected by the light path in discretized three-dimensional space.
Figure 50B:
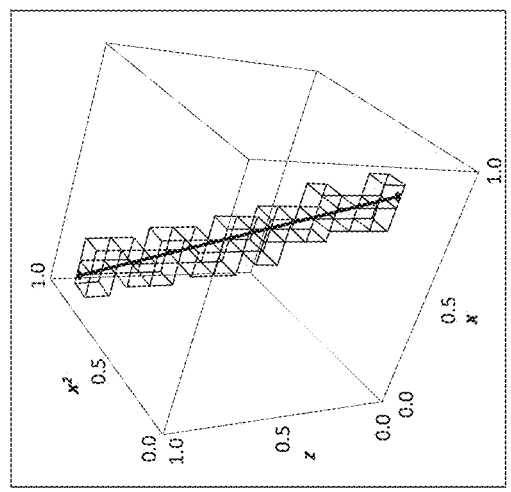
FIG. 50b depicts an exemplary activation of discrete voxels intersected by the light path in discretized three-dimensional space.
Figure 50A:
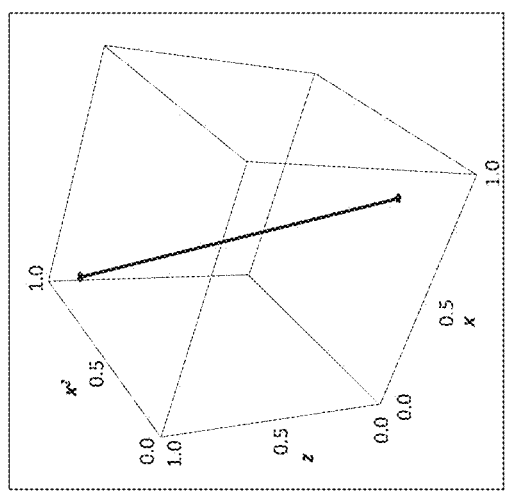
FIG. 50a depicts an exemplary light path between a light emission plane and a light sensing plane in three-dimensional space.
Figure 51B:
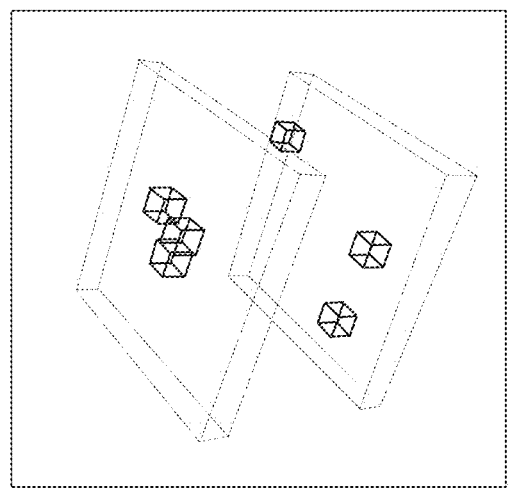
FIG. 51b depicts an exemplary cross-sectional view of a voxel arrangement in a discretized space.
Figure 51A:
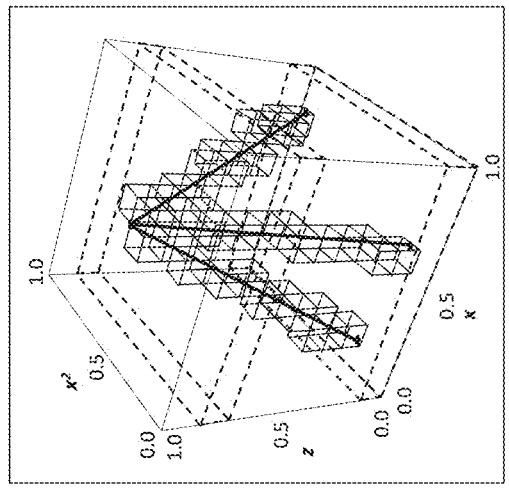
FIG. 51a depicts discretized planes in a discretized space, shown with voxels activated by multiple light paths.

In an example embodiment, the space between the light emitting and light sensing arrangement is divided into voxels as in FIG. 49b. One LED on the light emitting array would transmit every possible light path (as a cone of light) through the discretized space between the emitting LED and each light sensing element on the light sensing array. For example, FIG. 50a depicts an exemplary light path between a light emitting plane and a light sensing plane in three-dimensional space. FIG. 50b depicts an exemplary activation of discrete voxels intersected by the light path in discretized three-dimensional space. FIG. 50c further depicts an exemplary activation of discrete voxels intersected by the light path in discretized three-dimensional space. Additionally, FIG. 51a depicts discretized planes in a discretized space, shown with voxels activated by multiple light paths. FIG. 51b depicts an exemplary cross-sectional view of a voxel arrangement in a discretized space. For each light path such as those shown in FIG. 51a, the present invention will calculate which voxels the light path intersects, calculate the length of the light path passing through each voxel, and calculate the opacity of each voxel that the light path intersects. In a planar arrangement, the light emitting and light sensing arrays have n by n or $n^2$ LEDs and there will be at most $n^4$ light paths because each light path is defined by a pairing of light emitting and light sensing LEDs and there are $n^2 \times n^2 = n^4$ possible pairings of light emitting to light sensing LEDs. Consequently, there are also $n^4$ number of equations. Further, the number of voxels will vary from a minimum of $n^2$ wherein the distance between light emitting and sensing arrays is at a minimum and a maximum of $n^4$, wherein the number of unknowns are equal to the number of equations.

It is important to keep in mind the fact that this model is a gross approximation and oversimplification. It assumes that a light path between a light-emitting and light-sensing LED is an infinitesimally small line when in reality each light path is actually a whole group of light arrays with cylindrical thickness. This adds a second-order complexity to the calculations which can be implemented in certain embodiments of the present application. But briefly, because each light path now has thickness, one must account for the fact that a light path may intersect several voxels in one place at a time. Therefore when calculating the intersection length of the light path through each voxel, there are more parameters to consider.

1.4 Light Absorption Processes

Calculating the transmittance of a light path passing through several voxels can be calculated using Beer's law, which states that the transmission factor (fraction of light transmitted) for a path of length l and attenuation constant, a, is given by $T=e^{-al}$. Each voxel has an associated a value and a specific l value for every intersecting path of light, whereas each path of light has an associated T value. That means, for any given light path, there is one associated T value but n number of a and l values for n number of intersected voxels. In an example embodiment of the present invention, there are $n^3$ voxels and at most $n^4$ light paths, which yields a system of equations with $n^3$ unknown a values and at most $n^4$ transmittance equations (derived from Beer's Law). If all the T and l values are known for each equation within the system of equations, the a values can be calculated for each voxel. Because the system of equations is overdetermined (there are more equations than unknown variables), the a values should be calculated preferably using a pseudo-inverse technique to minimize the error. The calculated a values define the opacity for each voxel. Once the opacity of each voxel for the three dimensional space is calculated, the opacity of each voxel for the object also becomes known, and this data allows for the reconstruction of a three dimensional visualization of the object.

Figures 52A, 52B:
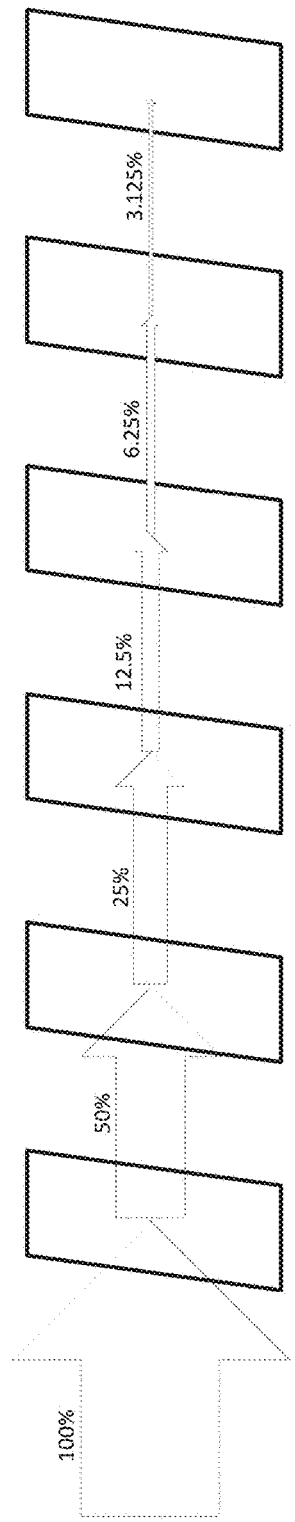
FIG. 52a depicts an example cascade of identical light transmission loss layers illustrating Beer's law.
FIG. 52b depicts an example set of data based on FIG. 52a showing a relationship between path length of light and light transmittance.

Some aspects of Beer's Law can further be illustrated by FIGS. 52a-52b. FIG. 52a depicts an example cascade of identical light transmission loss layers illustrating Beer's law. As seen in Beer's law, the opacity of each voxel and the length of a light path traveling through that voxel affect the transmission loss of the light. For example, changing either the opacity factor or changing the length by a factor of 2 can decrease the fraction of light transmitted. FIG. 52b depicts an example set of data based on FIG. 52a showing a relationship between path length of light and light transmittance, wherein it is apparent that as the light path length increases, the transmittance of light decreases.

Beer's Law can also be described by FIGS. 53a and 53b. In contrast to FIG. 52a, FIG. 53a depicts an example cascade of non-uniform light loss transmission through objects of different thicknesses. FIG. 53b depicts an example set of data based on FIG. 53a showing a relationship between transmittance and percentage of light loss, wherein it is apparent that as the transmittance increases depending on the non-uniform thickness of objects, the percentage of correspondingly increases or decreases. Since Beer's Law is not a linear relationship but rather a relationship of exponential decay ($T=e^{-at}$), this means that depending on how many voxels are chosen to discretize a 3-D object or space, there will be different calculated T values. The more finely discretized the space, or in other words, the smaller the voxels are, the more voxels each light path must intersect to get from the light-emitting array to the light-sensing array. The more voxels it intersects, the more the light gets attenuated, and the smaller the transmission value is.

2. First Model for Transmission-Based Tomography Computations

To better illustrate the above descriptions, this section explains a novel model of transmission-based tomography of 3-dimensional objects having at least partially transparent structures and surface boundaries (leveraging various associated conditions).

2.1 Indexing of Light Sensor Array and Light Emission Array

First assume a planar 2-dimensional light sensor array and a planar 2-dimensional light-emission array facing each other in a parallel arrangement configured so each sensor in the light sensor plane can receive light emitted by at least one light emitting element in the light emitting plane. Each light sensor element in the light sensor array has a unique index of the form $\{n_s, m_s\}$, where $n_s \in \{1, 2, \ldots, N_s\}$ and $m_s \in \{1, 2, \ldots, M_s\}$, and each light-emitting element has a unique index of the form $\{n_e, m_e\}$, where $n_e \in \{1, 2, \ldots, N_e\}$ and $m_e \in (1, 2, \ldots, M_e)$; accordingly the light sensor array comprises a total of $N_s M_s$ light-sensing elements and the light emitting array comprises a total of $N_e M_e$ light emitting elements.

2.2 Paths Between a Sensor in Light Sensor Array and Emitter in Light Emission Array Vs. Paths Between an Emitter in Light Emission Array and a Sensor in Light Sensor Array Each ordered quadruple, denoted by $$\{\{n_e, m_e\}, \{n_s, m_s\}\}$$

comprising a specific emitting light and sensing light in their respective arrays, defines a light path within the 3-dimensional discretized lattice. Think of the emitting light as the beginning of the light path and the sensing light as the destination of the light path. This path will be denoted by $$P(\{\{n_e, m_e\}, \{n_s, m_s\}\})$$

2.3 Intersection of Paths with Transparent Voxels

The 3-dimensional discretized lattice between the light emitting and light sensing arrays consists of a 3-dimensional array of voxels. In an exemplary case, two n by n arrays of lights, one emitting and one sensing, facing each other at n distance apart will be discretized into n3 adjacent individual cubes or voxels. These cubes are denoted by $C_{ijk}$, where ijk denotes a specific index for each cube with the following ranges:

$$\bigcup_{\substack{i \in \{1,2,\ldots,N\} \\ j \in \{1,2,\ldots,N\} \\ k \in \{1,2,\ldots,N\}}} C_{ijk}$$

The light path determined by $\{\{n_e, m_e\}, \{n_s, m_s\}\}$ intersects a small subset of the $N^3$ cubes. A path that intersects cube $C_{ijk}$ travels through cube $C_{ijk}$ along a line segment inside the cube, and the length of this line segment (which typically varies from cube to cube along the path) can be denoted as $L_{ijk}$. As an example, FIG. 50c depicts an exemplary activation of discrete voxels intersected by the light path in discretized three-dimensional space.

2.4 Total Transparency of a Path Intersecting Transparent Cubes

Again, a path that intersects cube $C_{ijk}$ travels through cube $C_{ijk}$ along a line segment inside the cube, and the length of this line segment (which typically varies from cube to cube along the path) can be denoted as $L_{ijk}$.

There is a transmittance value for light, denoted as $T_{ijk}$, that is associated with each cube $C_{ijk}$ and the length of the light path $L_{ijk}$ through the cube $C_{ijk}$. Each cube has an associated attenuation constant $a_{ijk}$. In general this attenuation constant can vary with light wavelength, temperature, light polarization, and other factors. However for simplification dependency these factors will be omitted. As described above, according to Beer's law, the transmittance value T (fraction of light transmitted) for a path of length/ and attenuation constant of value a is given by, $$T = e^{-al}$$

Thus for each cube $C_{ijk}$ intersected by the path $P\{\{n_e, m_e\}, \{n_s, m_s\}\}$ with a path segment of length $L_{ijk}$, the transmittance value will be given by $$T_{ijk}(L_{ijk}) = e^{-a_{ijk} L_{ijk}}$$

Thus the transmittance value of the total path can be calculated as the product of the transmittance values of each cube $C_{ijk}$ in the path:

$$T(P(\{\{n_e, m_e\}, \{n_s, m_s\}\})) = \prod_{\{i, j \cdot k\} \in P(\{\{n_e, m_e\}, \{n_s, m_s\}\})} T_{ijk}(L_{ijk})$$

$$= \prod_{\{i, j \cdot k\} \in P(\{\{n_e, m_e\}, \{n_s, m_s\}\})} e^{-a_{ijk} L_{ijk}}$$

2.5 Aperture Effects of Individual Light Sensors and Light Emitters

An important additional consideration is the aperture effects of individual light sensors and light emitters. If uniform manufacturing with adequate tolerances can be assumed, additional mathematical models can be included (dependent, for example, on the angle of emitter or incident light paths). Alternately and advantageously, the system can be calibrated in a simpler approach. Amplitude measurements of the light can be made for each light path and stored with the sensing lights in the sensing array when there is no object placed between the light sensing and light emitting arrays. These measurements establish a "base case" scenario that can then be used to provide calibrating normalization factors for other non-base case scenarios. These path-by-path normalization factors associated with these aperture effects simply scale the measurement values used in the linear equations. For example, if a specific sensing light $\{n_s,m_s\}$ detects a light amplitude of $A_0$ for path $P(\{\{n_e,m_e\},\{n_s,m_s\}\})$ without an object, and a light amplitude of $A_1$ with an object, then the normalized amplitude $A=A_1/A_0$.

Ideally the light emitter emits light for a path P with unit amplitude; for such an ideal case:

(measured received light amplitude)=(emitted light amplitude)·(transparency of path)

with (emitted light amplitude)=1 and (transparency of path)=$T(P)$ giving $T(P)$=(measured received light amplitude)

However, the emitted light amplitude can be expected to vary from path to path. Thus because of aperture effects it is more accurate to formulate the emitted light amplitude as a function of the path P, that is $A_{emit}(P)$. This gives $T(P) \cdot A_{emit}(P)$=(measured received light amplitude)

Similar path-dependent aperture effects can typically occur at the sensor as well. This can again be denoted with Asense(P). Including this consideration gives $T(P) \cdot A_{emit}(P) \cdot A_{sense}(P)$=(measured received light amplitude)

One can consolidate the two path-dependent aperture attenuations into a single function A(P), that is $A(P)=A_{emit}(P) \cdot A_{sense}(P)$.

Such a function A(P) can be measured empirically for a given specific implementation. Once known one can then write (for values of A(P)>0) the relation $$T(P) = \frac{\text{(measured received light amplitude)}}{A(P)}$$

Figure 54B:
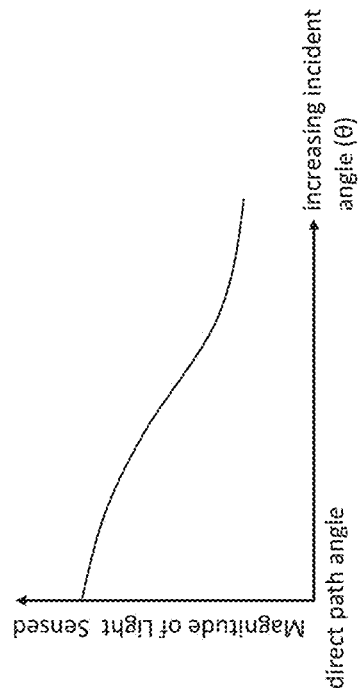
FIG. 54b depicts an example graph showing the relationship between magnitude of light sensed by a light sensing arrangement and the incident angle of the light path.
Figure 54A:
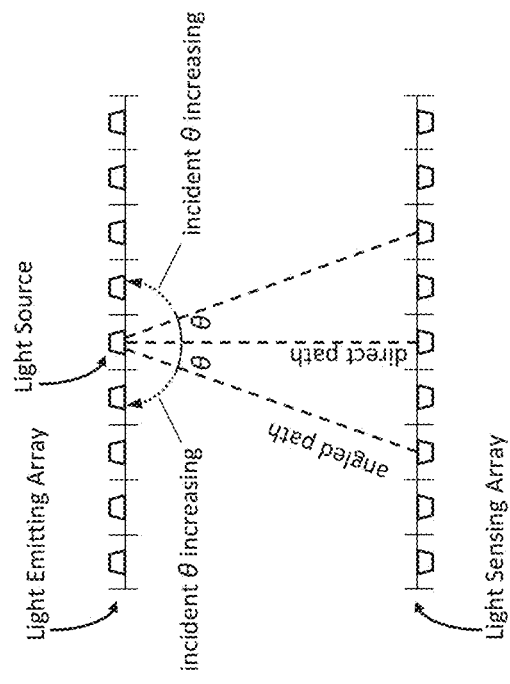
FIG. 54a depicts example aperture effects between a light emitting and light sensing arrangement in an optical tomography system.

FIG. 54a depicts example aperture effects between a light emitting and light sensing arrangement in an optical tomography system. FIG. 54b depicts an example graph showing the relationship between magnitude of light sensed by a light sensing arrangement and the incident angle of the light path. In reference to both FIGS. 54a and 54b, aperture effects can be described by the phenomenon that as the incident angle increases creating an angled path of light as opposed to a direct path of light, the amount of light sensed decreases.

Figure 55:
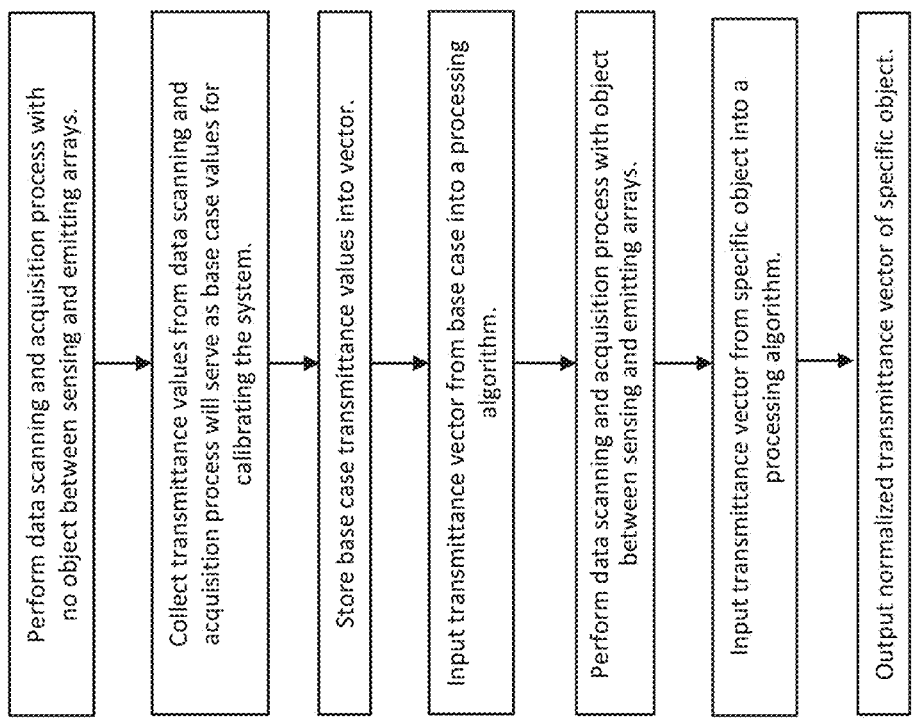
FIG. 55 depicts an exemplary empirical aperture measurement and normalization flow chart to account for aperture effects that may occur between light emitting and light sensing arrangement in discretized three-dimensional space.

FIG. 55 depicts an exemplary empirical aperture measurement and normalization flow chart to account for aperture effects that may occur between light emitting and light sensing arrangement in discretized three-dimensional space. In other terms, FIG. 55 illustrates an example process of how the system is calibrated to account for aperture effects. An algorithm designed to normalize data takes in two inputs, a transmittance vector of a base case scenario when no object is present between sensing and emitting arrays and, a transmittance vector of a specific scenario when a specific object is being imaged. The algorithm uses the base case scenario to normalize the transmittance vector of the specific scenario for more accurate measurements and calculations. A variety of software programming languages and environments can be used to implement the steps described in the flow chart and may be later adapted for scattering effects.

2.6 Use of Logarithms to Transform Total Transparency of a Path into a Linear Equation Taking the log of the above equation results in $$\log\left(\frac{\text{measurement}(P)}{A(P)}\right) = \log(T(P))$$

giving $\log(\text{measurement}(P))-\log(A(P))=\Sigma \log(T(P))=\Sigma \log(T_{ijk}(L_{ijk}))\{i,j,k\}\epsilon P(\{\{n_e,m_e\},\{n_s,m_s\}\})$ $=\Sigma \log(e^{-a_{ijk}L_{ijk}})\{i,j,k\}\epsilon P(\{\{n_e,m_e\},\{n_s,m_s\}\})$ $=-\Sigma a_{ijk}L_{ijk} \{i,j,k\}\epsilon P(\{\{n_e,m_e\},\{n_s,m_s\}\})$

2.7 Use of Multiple Paths to Build a System of Linear Equations

Groups of equations such as constructed above $\log(\text{measurement}(P))-\log(A(P))=-\Sigma a_{ijk}L_{ijk}\{i,j,k\}\epsilon P(\{\{n_e,m_e\},\{n_s,m_s\}\})$ can be used to create a system of equations. That is, a selected group of paths together form a collection P* of paths $P^*=\{P(\{\{n_e,m_e\},\{n_s,m_s\}\})\}$.

For each path P∈P* (each P is P ($\{\{n_e,m_e\},\{n_s,m_s\}\}$)), a transmittance value T(P) can be measured, and the collection of lengths $\{L_{ijk}\}$ for each cube intersected by the light path can be calculated with geometry.

2.8 Adequate Number of Equations

The individual attenuation constants $\{a_{ijk}\}$ associated with each cube, or voxel $\{C_{ijk}\}$, can then be treated as unknown variables, which can then be solved for if the collection of paths P* consist of enough linearly-independent equations.

2.9 Over-Specified System of Equations

Figure 56B:
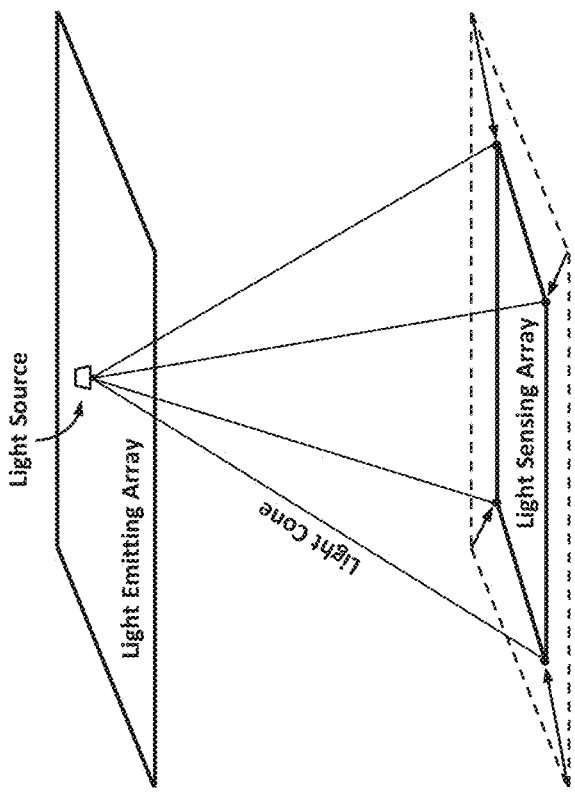
FIG. 56b depicts an exemplary planar geometry light emitting and light sensing arrangement wherein the emitting and sensing planes are of different dimensions.
Figure 56A:
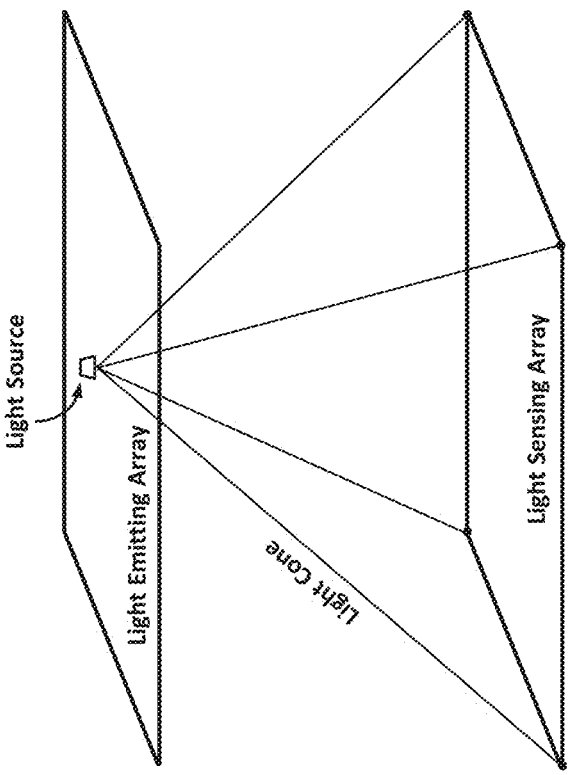
FIG. 56a depicts an exemplary planar geometry light emitting and light sensing arrangement wherein the emitting and sensing planes are of the same dimensions.
Figure 57:
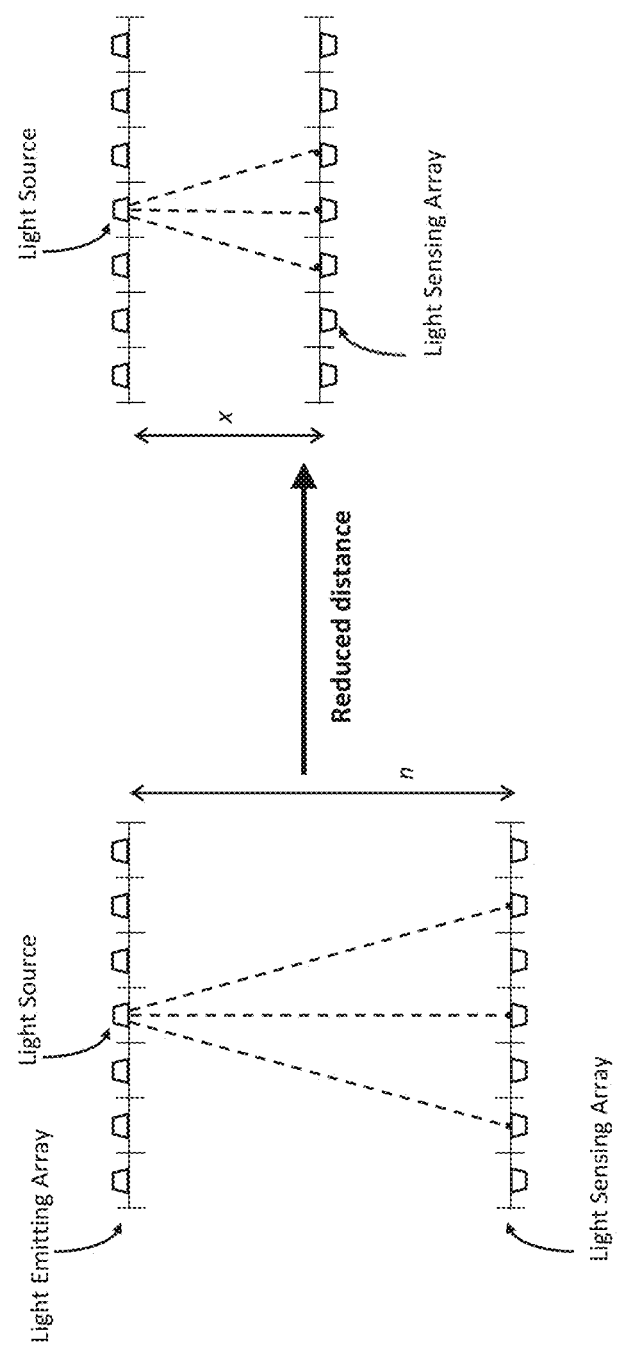
FIG. 57 depicts an exemplary planar geometry light emitting and sensing arrangement wherein the distance between emitting and sensing planes is reduced.

If the measurements can be expected to be noisy or non-ideal, it can be advantageous for the collections of paths P* to have more equations than unknown variables so as to create an over-specified system of (potentially inconsistent)

linear equations. The over-specified system can be solved with a generalized inverse operation such as the Moore-Penrose Generalized Inverse, which finds the solution that minimizes the error. In certain embodiments, however, it may be advantageous to reduce computational processing and increase efficiency, which may be achieved through reducing the number of equations. FIG. 56a depicts an exemplary planar geometry light emitting and light sensing arrangement wherein the emitting and sensing planes are of the same dimensions. FIG. 56b depicts an exemplary planar geometry light emitting and light sensing arrangement wherein the emitting and sensing planes are of different dimensions. In having differing dimensions of the emitting and sensing planes, fewer equations are generated and therefore, computations are reduced. Another way to reduce computational processing is based on FIG. 57. FIG. 57 depicts an exemplary planar geometry light emitting and light sensing arrangement wherein the distance between emitting and sensing planes is reduced, thereby reducing the number of light paths and overall computational processing.

2.10 Example Sizings and Coordination of Indexing

The mathematics is simpler if $n_e = n_s$ and $m_e = m_s$ and if the light sensor plane and light emitter planes are consistent and aligned so that the sensor element indices, emitter element indices, and cube indices are subsets of a common indexed lattice. However, the invention provides for a wide range of variations, array sizes, configurations, and other choices for the light sensor arrays and a wide range of different variations, array sizes, configurations, and other choices for the light emission arrays.

3. Example Physical Implementation

Now we will illustrate in greater detail the software and hardware implementation of the invention including an example of the data path associated with the invention.

3.1 Example Software Implementation

Figure 58:
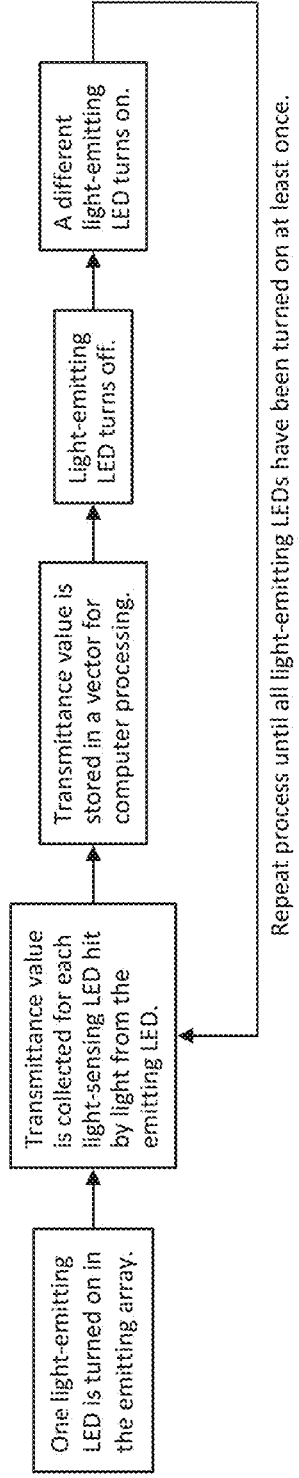
FIG. 58 depicts an exemplary measurement data scanning and acquisition flow chart for data gathered by the light sensing array about an object placed between light emitting and light sensing arrangement in discretized three-dimensional space.

FIG. 58 depicts an example measurement data scanning and acquisition flow chart for data gathered by the light sensing array about an object placed between light emitting and light sensing arrangement in discretized three-dimensional space. A first light-emitting LED is turned on in the emitting array. Then, a transmittance value is collected for each light-sensing LED that senses light from the emitting LED. The transmittance value is then stored in a vector for computer processing. The first light-emitting LED then turns off and a different light-emitting LED turns on. This process repeats until all light-emitting LEDs have been turned on at least once. In one embodiment, a computer processing system can be used to provide coordinates to control the measurement data scanning and acquisition, including controlling of the LEDs turning on or off. FIG. 58 is exemplary and is not limited by the order shown in the flow chart. A variety of software programming languages and environments can be used to implement the steps described in the flow chart.

Figure 59:
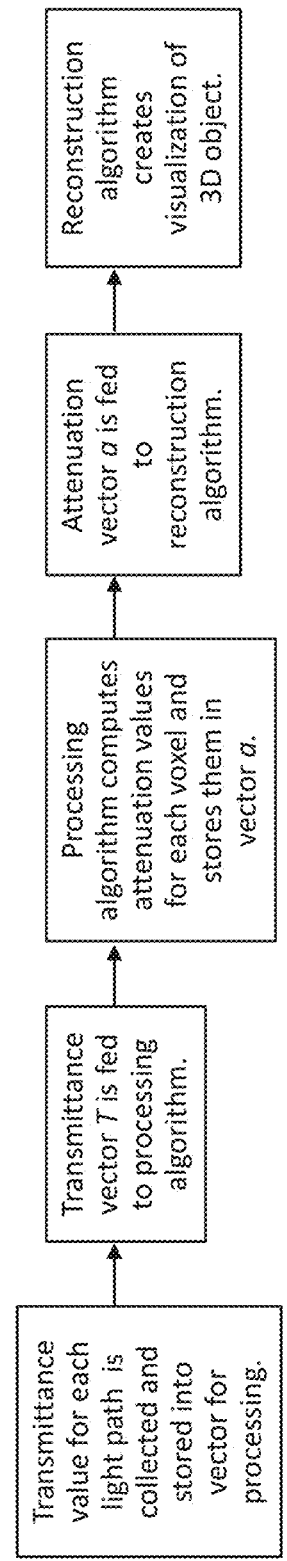
FIG. 59 depicts an exemplary measurement data processing flow chart for data gathered by the light sensing array about an object placed between light emitting and light sensing arrangement in discretized three-dimensional space.

FIG. 59 depicts an exemplary measurement data processing flow chart for data gathered by the light sensing array about an object placed between light emitting and light sensing arrangement in discretized three-dimensional space. In this example, a transmittance value for each light path is collected and stored into a vector T for processing. This vector T is fed to a processing algorithm (i.e., using Matlab™) which computes attenuation values for each voxel and stores them in a vector a. Attenuation vector a is then fed to a 3D reconstruction algorithm (i.e., using Mathematical™), which creates a visualization of the 3D object. FIG. 59 is exemplary and is not limited by the order shown in the flow chart. A variety of software programming languages and environments can be used to implement the steps described in the flow chart.

3.2 Example Hardware Implementation and Data Path

Figure 60:
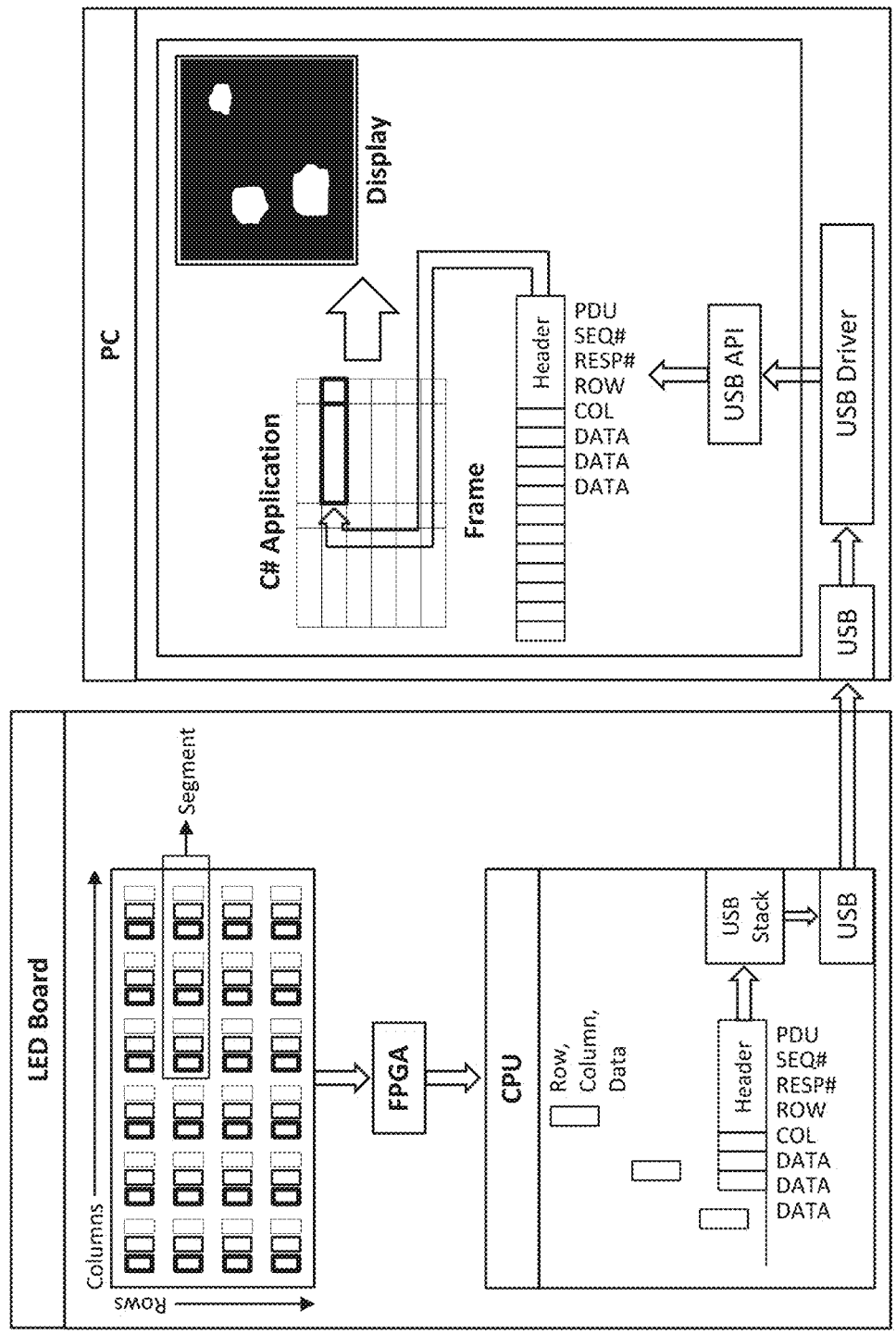
FIG. 60 depicts an example hardware and software architecture implementation in an optical tomography system for a data path.

FIG. 60 depicts an example hardware and software architecture implementation in an optical tomography system for a data path. Data path generally refers to how data is processed from hardware to the software associated with the invention. Referring to FIG. 60, the hardware would typically include but is not limited to the LED sensor array, a field programmable gate array, an embedded processor, a USB stack, USB link, a computer—with a USB driver, USB, API, software for controlling the invention, memory, data storage, a display, etc. The embedded CPU communicates with the FPGA and retrieves from the FPGA the information for each individual sensor. The embedded CPU uses its RAM to assemble all the individual sensor data into a frame. The concept of a frame provides the benefit of "synchronizing" the data elements into the concept of one sensor image or frame, defined by a unique time stamp. That concept can then have additional attributes such as capture settings, sequence number, etc. Technically it is also a natural concept in the USB and Ethernet interfaces, with a natural 1-to-1 mapping. Each frame is then sent by the embedded CPU to the computer via USB or Ethernet. Typically, UDP packets would be a good choice to stream the frames efficiently over a reliable network. If reliability is an issue, TCP can be implemented and a "frame start pattern" can be added to sync/resync to the start of each frame within the byte-oriented TCP stream. The computer software application, can be written in a programming language such as C#/. NET, using a standard Microsoft™ USB driver for the HID device class. Configuring the embedded CPU USB stack to present itself as a HID device has the advantage of being very universally compatible with any operating system and its native drivers. The software application makes calls to the driver layer at regular intervals in order to retrieve any data that may have accumulated in the internal queue of the driver. Then, the application performs some transformations in order to generate the graphical data and display it. This includes linear mapping to color range, application of linear calibration correction, etc.

Figure 61:
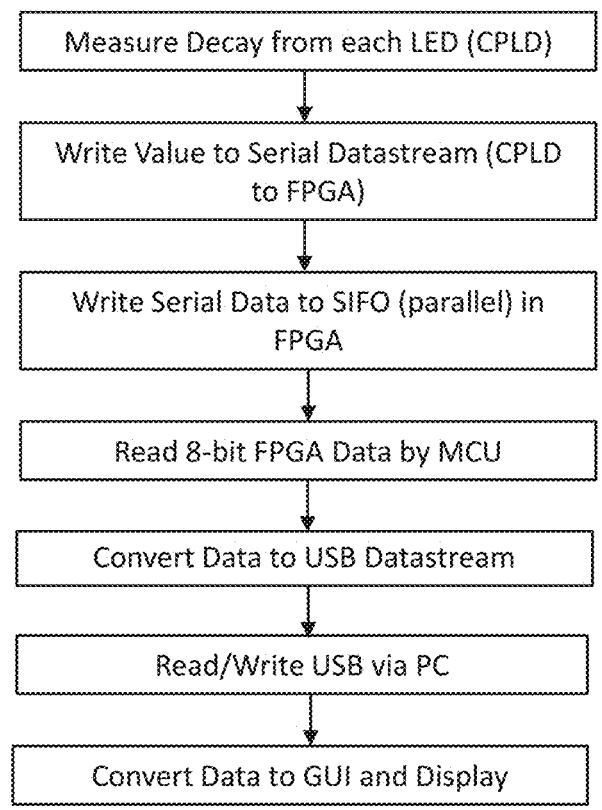
FIG. 61 depicts an example method illustrating steps in the flow of the data path of the invention.

FIG. 61 depicts an example method illustrating steps in the flow of the data path of the invention.

Alternative embodiments using a variety of computing hardware and software can be implemented depending on the amount of data, required performance, etc.

4. Effects of Refraction, Reflection, and Light Scattering

The present application can also be configured to account in various degrees for various aspects of the effects of refraction, reflection, and light scattering.

FIG. 62a depicts an example of refraction of a light path transmitted through a transparent object between light emitting and light sensing arrangement.

FIG. 62b depicts an example of light scattering of a light path transmitted through a translucent object between light emitting and light sensing arrangement.

Figure 62C:
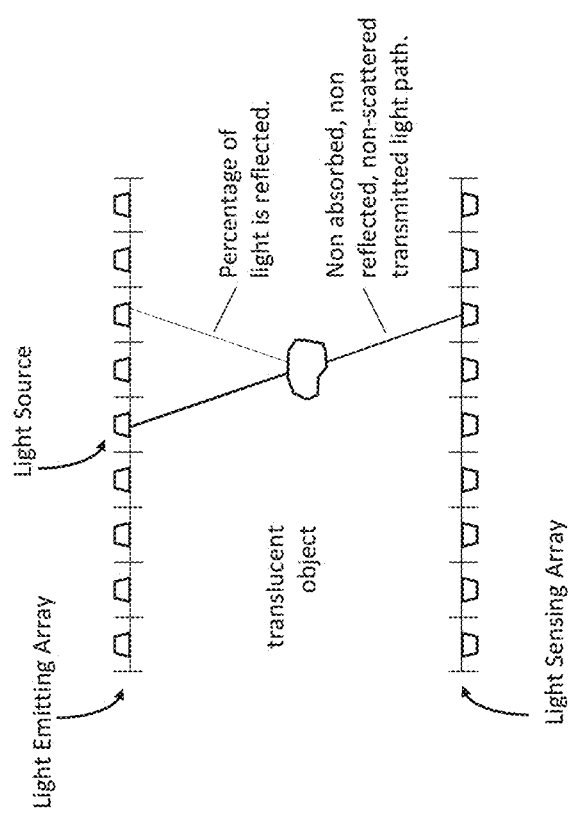
FIG. 62c depicts an example of reflection of a light path through a transparent object between light emitting and light sensing arrangement.

FIG. 62c depicts an example of reflection of a light path through a transparent object between light emitting and light sensing arrangement.

5. Cylindrical Geometry Arrangements

5.1 Cylindrical Light Emitting and Sensing Arrangement

Figure 63C:
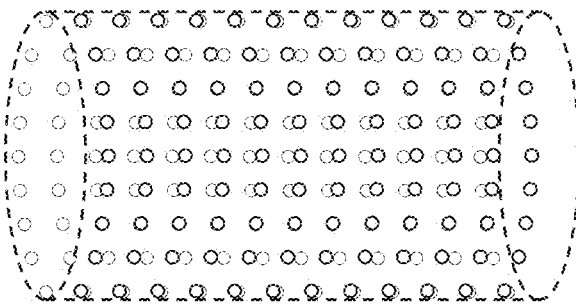
FIG. 63c depicts the LED arrangement of FIG. 63b with an arrangement of LEDs on a front side and back side of the cylindrically shaped system.
Figure 63B:
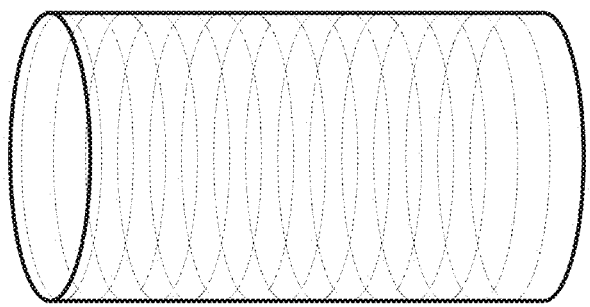
FIG. 63b depicts the arrangement of FIG. 63a with a row-like arrangement of LEDs in a cylindrically shaped system.
Figure 63A:
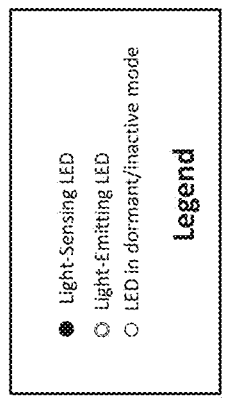
FIG. 63a depicts an example light emitting and light sensing arrangement with cylindrical geometry in an optical tomography system.

As mentioned previously, various embodiments of the invention can include a variety of geometric arrangements. One example of alternate geometric arrangements of value are those that are cylindrical. FIG. 63a depicts an example light emitting and light sensing arrangement with cylindrical geometry in an optical tomography system. FIG. 63b depicts the arrangement of FIG. 63a with a row-like arrangement of LEDs in a cylindrically shaped system. FIG. 63c depicts the LED arrangement of FIG. 63b with an arrangement of LEDs on a front side and back side of the cylindrically shaped system. FIG. 63d depicts an example side view of emitting LED from the back side of the cylindrically shaped system to the front side. FIG. 63e depicts an example emitting LED emitting light in and among LEDs in an emitting array from the back side of the cylindrically shaped system to the front side wherein a plurality of sensing LEDs sense the emitted light among LEDs in a sensing array. FIG. 63f depicts an example emitting LED emitting light from the back side of the cylindrically shaped system to the front side wherein a plurality of sensing LEDs sense the emitted light.

Figure 63H:
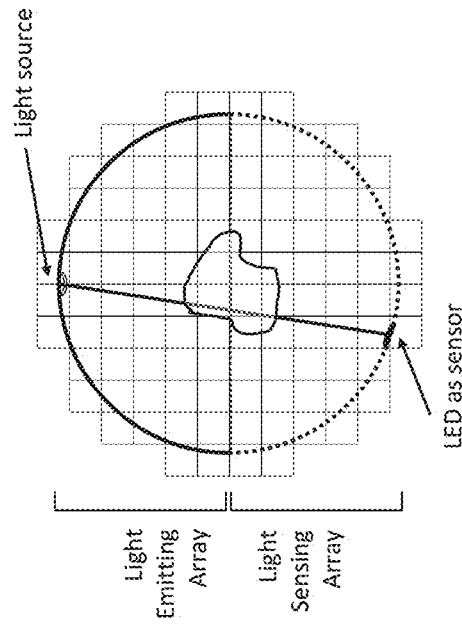
FIG. 63h depicts a top view of an example discretization of a light emitting and light sensing arrangement with cylindrical geometry in an optical tomography system.
Figure 63G:
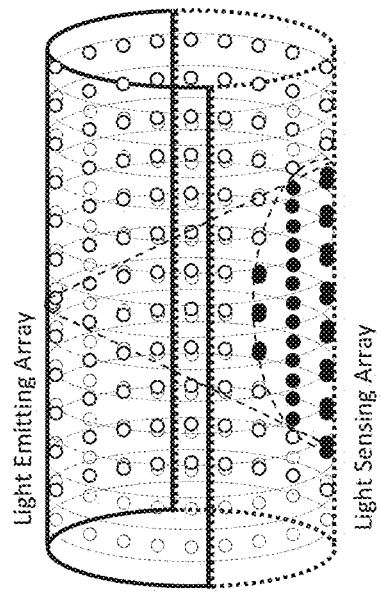
FIG. 63g depicts a more detailed and rotated view of the cylindrical arrangement of FIG. 63a, showing an emitting array and a sensing array.

A cylindrical arrangement can have a variety of embodiments. An example embodiment is FIG. 63g, which depicts a more detailed and rotated view of the cylindrical arrangement of FIG. 63a, showing an emitting array and a sensing array. Each of the two arrays form curved planes based on the curvature of the shape of the cylindrical structure implemented and shows an axis about which the cylinder is formed, for illustration purposes. FIG. 63g further shows a row-like arrangement of LEDs in more detail than FIG. 63b.

As with the planar light sensing and light emitting arrangement described earlier, the cylindrical arrangement can also be discretized into cubes, or voxels, but without perfect alignment with the curvature of the cylindrical structure. FIG. 63h depicts a top view of an example discretization of a light emitting and light sensing arrangement with cylindrical geometry in an optical tomography system. In FIG. 63h, it can be seen that the voxels lying both inside and outside the cylindrical structure, do not have precise alignment with the curvature of the cylindrical structure since the voxels lying both inside and outside the cylindrical arrangement do not perfectly align with the curvature of the cylindrical structure, the resulting attenuation constants for these voxels lying inside and outside the cylindrical arrangement will be an approximation, and will provide less accurate visualization of the object when the object is closer to the edge of the cylinder, as opposed to the object being placed towards the center of the cylindrical arrangement. Another approach that can be applied is to prorate the volume of the voxels that lie at the edge of the cylinder. This would provide an approximation with greater accuracy. Specifically, based on Beer's law, there is less accuracy because the $l_{ijk}$ values for the voxels lying inside and outside the cylindrical boundary of the cylindrical arrangement will be typically be an approximation since the length of light path passing through these voxels is only passing through part of the voxel. The effect of such approximations can be accounted for by various methods such as prorating the lengths light paths or ensuring there is no imagable subject matter in the However, for many applications a cylindrical arrangement may be advantageous as opposed to a planar arrangement, due to the curvature of the cylindrical arrangement, providing a more detailed view of the object, since the LEDs are arranged at an angle, providing a greater number of direct light paths through the object. In other words, due to the curvature of the cylindrical arrangement, the number of direct light paths traveling through the object is optimized and since a direct path light has the greatest brightness, this increases the accuracy of the measurements taken by the system.

Further, in a cylindrical arrangement, LEDs can be co-optimized for both emitting and sensing properties in order to provide a 360 scan of the object, distinguishing it further from the planar arrangement described above.

While the planar arrangement view may be advantageous for planar objects such as a sample that has be sliced or flattened so as to be accommodated on a microscope slide, a cylindrical arrangement might provide for better resolution for spherical objects such as a sample examined without slicing or flattening.

The mathematical computations involved with a cylindrical arrangement are very similar to those of a planar arrange and still use Beer's Law. Again, Beer's Law defines the relationship between the transmittance of light with the length of a light path through an object and that object's opacity. Because of the different geometry, however, this law must be applied to different parameters. In the cylindrical case, we define three parameters: c, n, and A. The variable c represents the number of LEDs in a single row of LEDs in the cylindrical arrangement, n represents the number of rows of LEDs in the cylindrical arrangement, and A represents the number of voxels per row of LEDs (these as depicted in FIG. 63g), Therefore, in a cylindrical case, the number of voxels is equal to A*n and the maximum number of equations is given by $(n*(c/2))^2$ because there are $n*(c/2)$ light-emitting LEDs and $n*(c/2)$ light sensing LEDs. $n*(c/2)*n*(c/2)$ become the total possible number of pairings between each light-emitting and light-sensing LED; each pair defines a light path.

To apply Beer's Law, similar to the planar case, one must calculate the intersection path length of light for each light path. To do this, one must first define the position of each light-emitting LED and light-sensing LED in space. In a planar geometry, this is simpler because the z coordinates for the light-emitting and light-sensing planes are constant, so it is only necessary to calculate the x and y coordinates. In a cylindrical geometry, the z coordinates are no longer constant for each LED array because they are curved. Therefore, it is necessary to calculate the x, y, and z coordinates dependently. Such a calculation often can be simpler when using polar coordinates and then convert polar to Cartesian coordinates. Once the coordinates for each light-emitting and light-sensing LED is defined, it becomes very simple to calculate which voxels each light path intersects and the length of light that intersects each voxel, and it is exactly the same as the planar case.

Figure 64:
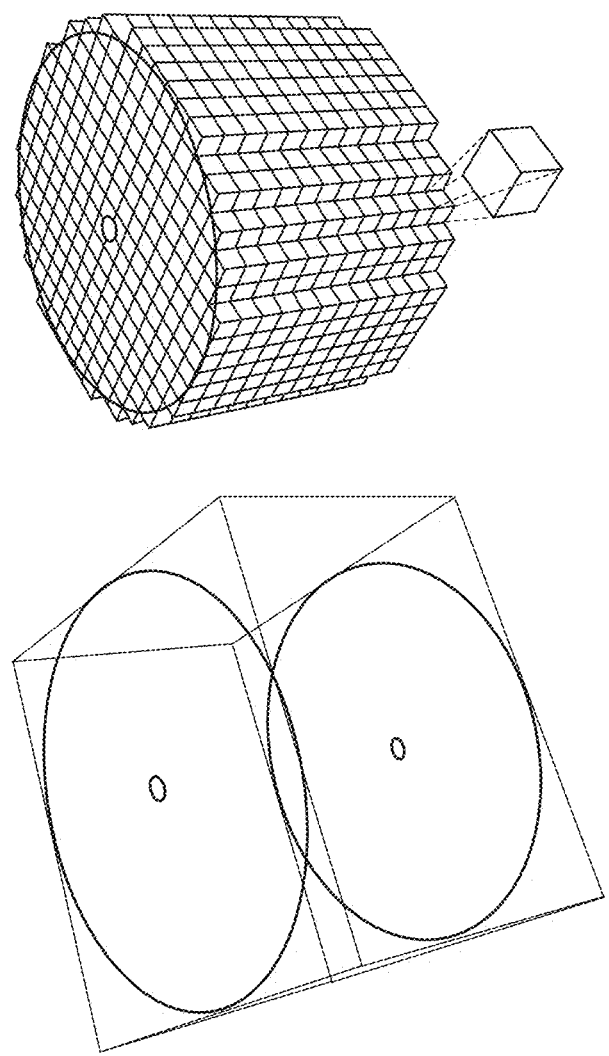
FIG. 64 shows an example embodiment of a discretization of space in a cylindrical light emitting and light sensing arrangement in an optical tomography system.
Figure 65A:
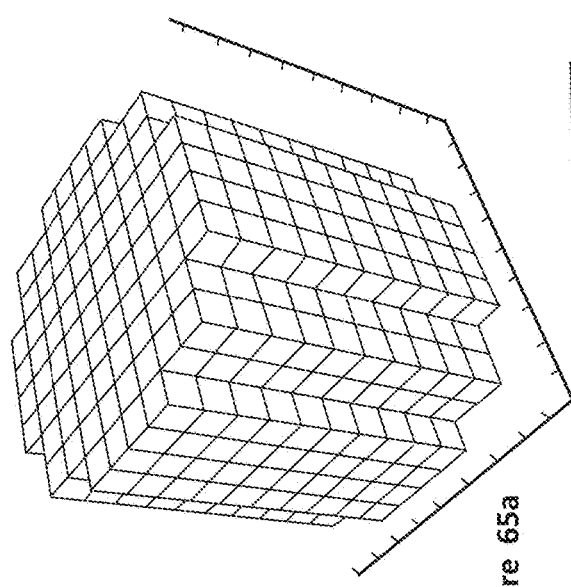
FIGS. 65a-65c show multiple views of an example embodiment of a discretization of space for a cylindrical light emitting and light sensing arrangement in an optical tomography system.
Figure 65B:
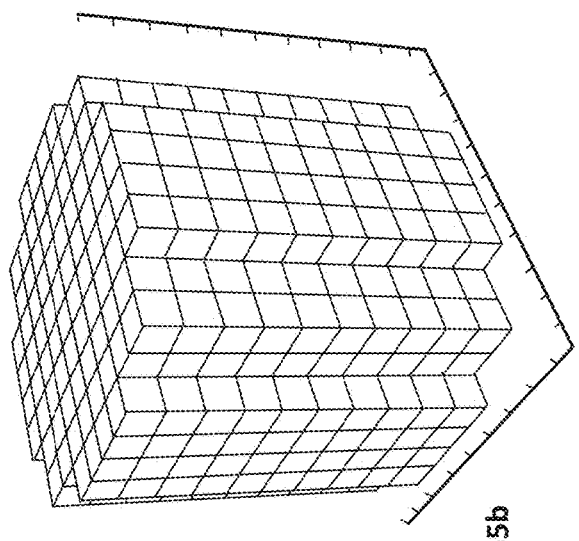
Figure 65C:
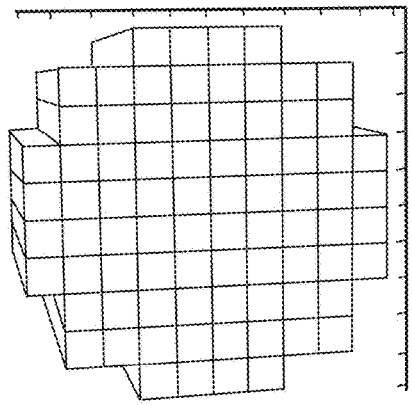
Figure 66B:
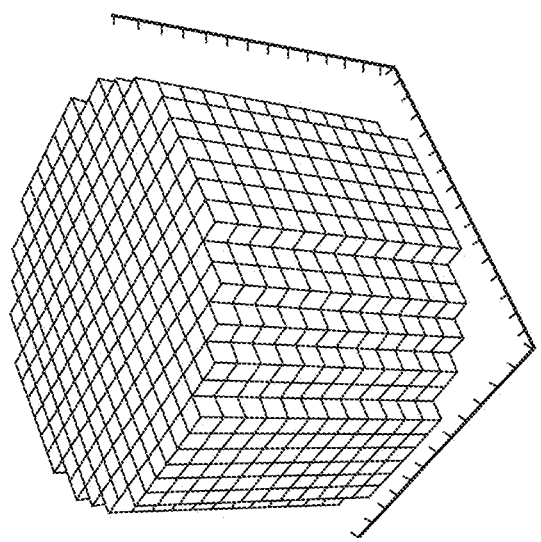
Figure 66A:
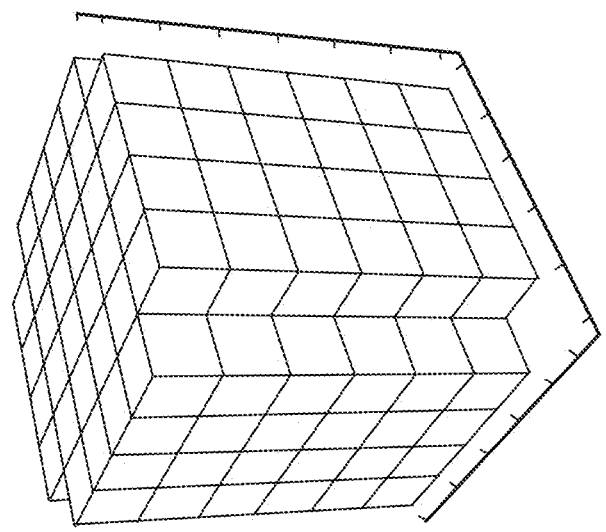
Figure 67B:
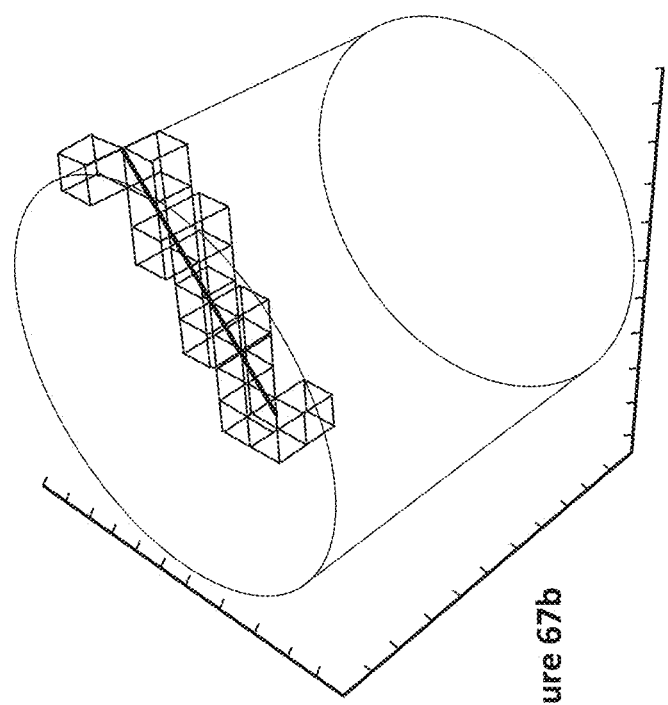
FIGS. 67a-67b depict an exemplary activation of discrete voxels intersected by a light path in discretized three-dimensional space in a cylindrical arrangement in an optical tomography system.
Figure 67A:
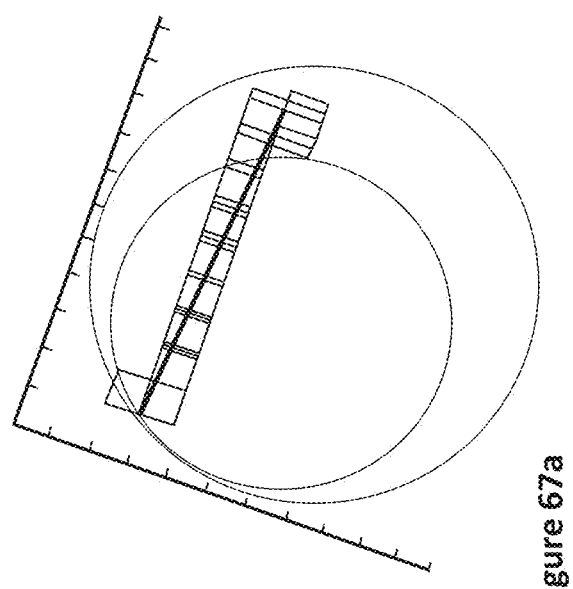

To better illustrate discretization of a cylindrical arrangement, FIG. 64 shows an example embodiment of a discretization of space in a cylindrical light emitting and light sensing arrangement in an optical tomography system. Further, FIGS. 65a-65c show multiple views of an example embodiment of a discretization of space for a cylindrical light emitting and light sensing arrangement in an optical tomography system. The amount of discretization may vary depending on the object being imaged, accuracy of approximation desired, etc. FIGS. 66a-66b show an example embodiment of a discretization of space for a cylindrical light emitting and light sensing arrangement in an optical tomography system, wherein FIG. 66b shows increased discretization. As shown in the planar arrangement above, FIGS. 67a-67b depict an exemplary activation of discrete voxels intersected by a light path in discretized three-dimensional space in a cylindrical arrangement in an optical tomography system. Although the principle behind discretization remains generally the same whether the arrangement is planar or cylindrical, the computations and approximations associated with a specific measurement using a particular geometric arrangement can vary as illustrated above.

6. Example Holding Arrangements and Modules

The present invention can comprise a holding module for a variety of implementations and applications.

Figure 68B:
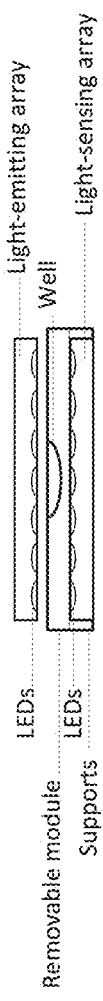
Figure 68A:
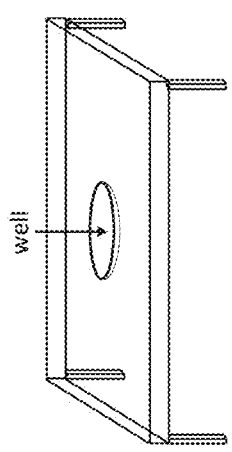
FIG. 68a illustrates an example sample holding module, as a slide with a well for a planar light emitting and light sensing arrangement in an optical tomography system for cytometry.

FIG. 68a illustrates an example sample holding module, as a slide with a well for a planar light emitting and light sensing arrangement in an optical tomography system for cytometry. In one embodiment, the holding module in FIG. 68a, is a well embedded into a transparent removable module with leg-type acting as supports for the removable module, which extend outside the boundaries of the LED arrays. In other embodiments, the holding module in FIG. 68a, as well the support structure may have different dimensions.

FIG. 68b illustrates a side view of the example holding module of FIG. 68a.

Figure 69B:
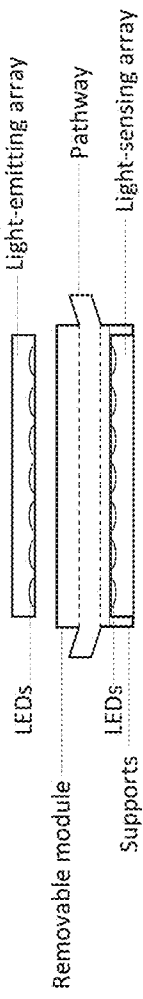
Figure 69A:
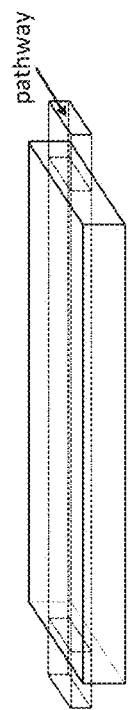
FIG. 69a illustrates an example holding module, as a pathway for a planar light emitting and light sensing arrangement in an optical tomography system.

FIG. 69a illustrates an example holding module, as a pathway for a planar light emitting and light sensing arrangement in an optical tomography system. FIG. 69b illustrates a side view of the example holding module of FIG. 69a. The portions of pathway that extend past the 2 arrays may be parallel with the arrays, or may also be angled, as shown in FIG. 69b, to prevent compromise of samples (spilling, etc.) from gravity or other factors. The configuration in FIG. 69a may be useful in flow cytometry and microfluidic applications.

Figure 70A:
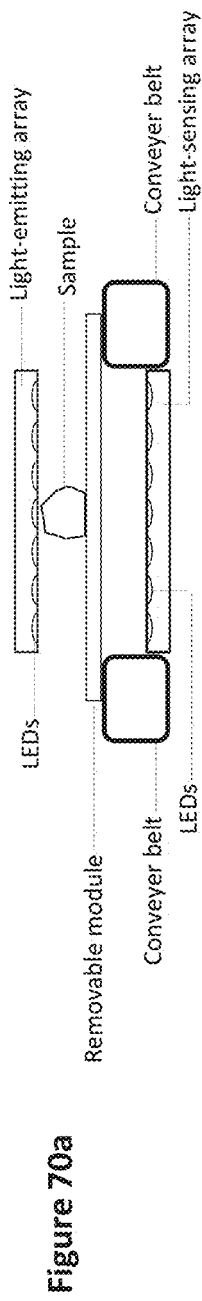
FIG. 70a illustrates an example holding module, as a belt configuration for a planar light emitting and light sensing arrangement in an optical tomography system.
Figure 70B:
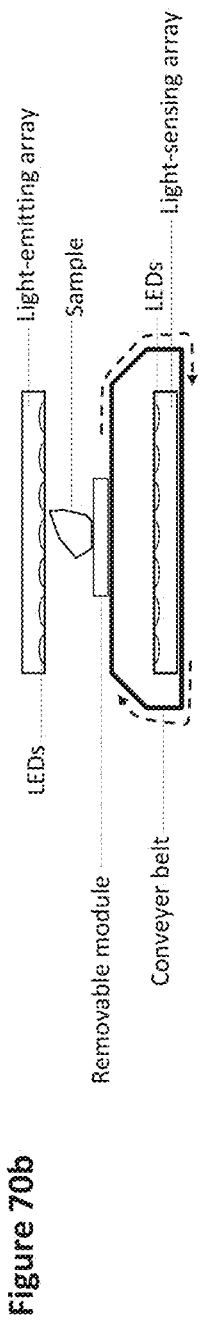

FIG. 70a illustrates an example holding module, as a belt configuration for a planar light emitting and light sensing arrangement in an optical tomography system. In FIG. 70a, a belt configuration, as seen front the front or back, with two conveyer belts, a transparent removable module that travels through the light-emitting and light-sensing arrays by way of 2 or more conveyor belts, which can extend outside the boundaries of the LED arrays to prevent corrupting a scan of the object. The sample can be deposited onto the module by way of a well, a pathway, or simply placed onto the module, in a way similar to a microscope slide.

Figure 71B:
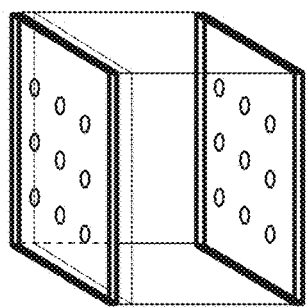
FIG. 71b illustrates another example holding module, as a shell configuration for a planar light emitting and light sensing arrangement in an optical tomography system.
Figure 71C:
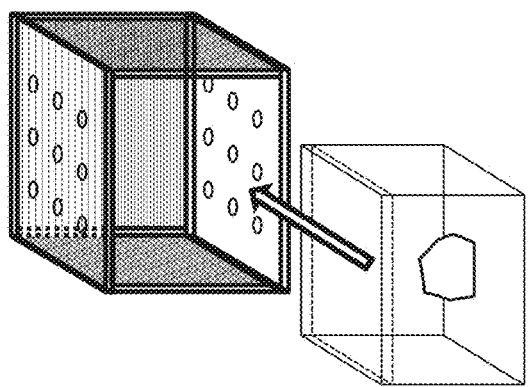
FIG. 71c illustrates yet another example holding module, as a shell configuration for a planar light emitting and light sensing arrangement in an optical tomography system.
Figure 71A:
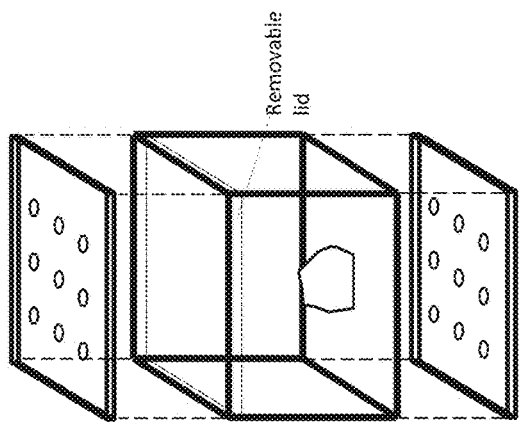
FIG. 71a illustrates an example holding module, as a shell configuration for a planar light emitting and light sensing arrangement in an optical tomography system.

FIG. 71a illustrates an example holding module, as a shell configuration for a planar light emitting and light sensing arrangement in an optical tomography system. The shell configuration illustrated in FIG. 71a a transparent removable module in the form of a transparent enclosure, which can have a variety of shapes depending on the harnessing of the module to the light emitting and sensing arrangement. One embodiment of this configuration is a cube with a removable lid, into which a sample can be inserted.

FIG. 71b illustrates another example holding module comprising a shell configuration for a planar light emitting and light sensing arrangement in an optical tomography system. The shell configuration illustrated in FIG. 71b comprises a transparent removable module in the form of a transparent enclosure, which can then be inserted between the arrays for scanning, in a stackable arrangement, as demonstrated by this figure which can have a variety of shapes depending on the harnessing of the module to the light emitting and sensing arrangement.

FIG. 71c illustrates yet another example holding module comprising a shell configuration for a planar light emitting and light sensing arrangement in an optical tomography system. In the configuration in FIG. 71c, the removable module holding a sample can be of a variety of sizes, and can be inserted into the configuration.

Figure 72B:
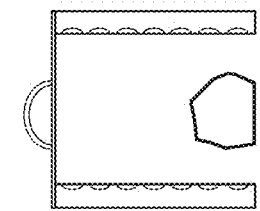
FIG. 72b illustrates an example holding module, as a hook configuration for a planar light emitting and light sensing arrangement in an optical tomography system.
Figure 72C:
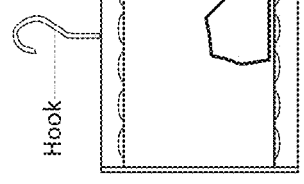
FIG. 72c illustrates the example holding module of FIG. 72a, wherein the handle is placed at a different location.
Figure 72E:
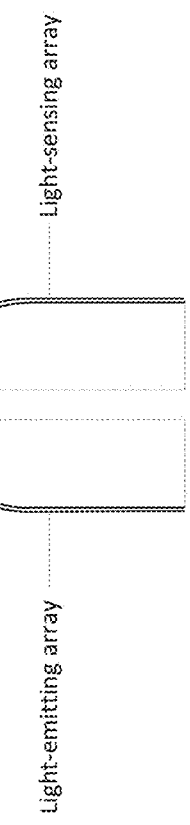
FIG. 72e illustrates the light emitting and sensing arrays of the holding module of FIG. 72d.
Figure 72A:
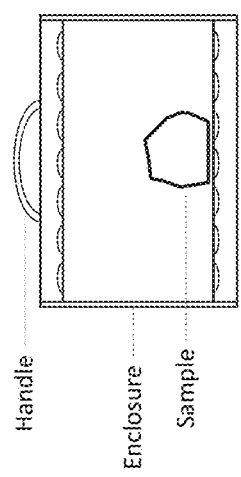
FIG. 72a illustrates an example holding module, as a handle configuration for a planar light emitting and light sensing arrangement in an optical tomography system.

FIG. 72a illustrates an example holding module comprising a handle configuration for a planar light emitting and light sensing arrangement in an optical tomography system. In the configuration of FIG. 72a, the removable module holding a sample may be of any size, and can be inserted into the configuration. Such an arrangement may be applied to a variety of configurations, to increase ease-of-use outside the traditional environment of a lab.

FIG. 72b illustrates an example holding module comprising a hook configuration for a planar light emitting and light sensing arrangement in an optical tomography system.

FIG. 72c illustrates the example holding module of FIG. 72a, wherein the handle is placed at a different location. Many other types of handle arrangements are anticipated and provided for by the invention, including wand, paddle, and various "dustpan"-like configurations.

Figure 72D:
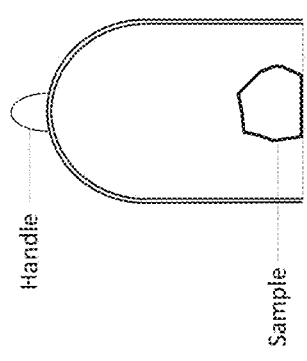
FIG. 72d illustrates an example holding module, as a bell configuration.
Figure 73B:
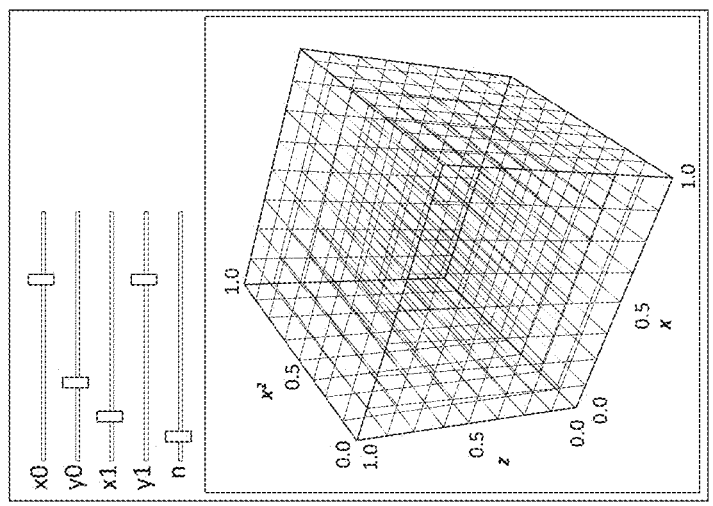
FIG. 73b shows an example graphical rendering in a visualizer module of a discretized three-dimensional space between a planar light emitting and light sensing arrangement.
Figure 73A:
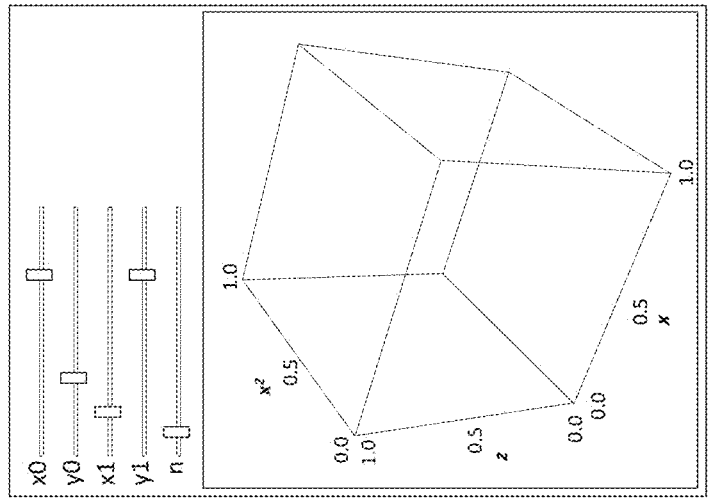
FIG. 73a shows an example graphical rendering in a visualizer module of three-dimensional space between a planar light emitting and light sensing arrangement.
Figure 74C:
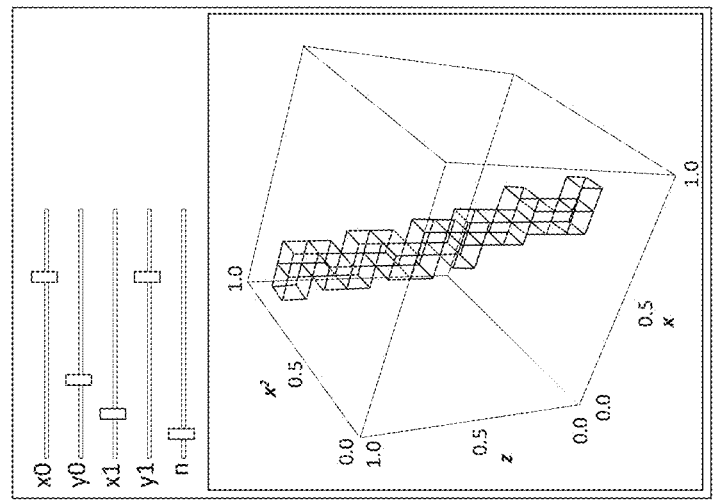
FIG. 74c further depicts an exemplary graphical rendering in a visualizer module of an activation of discrete voxels intersected by the light path in discretized three-dimensional space.

FIG. 72d illustrates an example holding module, a comprising a "bell-jar"-like configuration. FIG. 72e illustrates the light emitting and sensing arrays of the holding module of FIG. 72d. In the case of the bell-shaped configuration, the light-emitting LEDs and light-sensing arrays may be arranged in such a way that one half of the bell comprising of light-emitting LEDs, and the other half comprising of light-sensing LEDs, as shown in this figure. In the form of a bell configuration, the arrangement may be placed over a sample.

The configurations of the holding modules can be adapted and combined in various ways depending on the application and size of the objects to be inserted. The holding modules can be made of various materials in order to optimize performance and maintain or improve the accuracy of measurements by the system.

7. Light-Path Visualizers

The present invention can further comprise a visualizer module which may have image viewing, editing, and processing capabilities for handling 3D data, voxel operations, local filtering, morphology, etc. The visualizer module can comprise various controls via a graphical user interface of the module, associated with varying the view and dimensions of the visual rendering. The visualization module can also include controls and sliders associated with mathematical properties of the visual rendering. FIGS. 73a, 73b, 74a, 74b, 74c, 75a, and 75b depict various exemplary graphical renderings in a visualizer module. For example, as can be seen in FIGS. 73a, 73b, 74a, 74b, 74c, 75a, and 75b, coordinates associated with discretized space can be controlled via sliders on the top portion of a viewing window. Of course, the visualizer controls shown here are only exemplary and can be modified depending on the functionality desired.

8. Example Applications

The present invention can be utilized in a variety of applications, such as in microscopy, microplates, fluorescence detection, microfluidics, cytometry, and flow cytometry. Other applications are anticipated and provided for by the invention.

8.1 Microscopy

Microscopy involves the use of microscopes and other related imaging systems in the study of small organisms, samples, and other objects that cannot be seen without magnification by the unaided eye. Microscopy has several branches, including for example optical microscopy and electron microscopy, each of which in turn have various subbranches.

The present invention can be readily applied to the branch of optical microscopy, which images samples using properties of light. In the traditional sense, optical microscopes use a single or multiple lenses to magnify a sample so that it becomes visible to the naked eye.

Various embodiments of the present invention, as described, can be such that they do not use lenses. The invention, as applied to microscopy can image lighter, transparent samples. The resolution, determined by the size of the LEDs being used within the sensing and emitting arrays, also has potential to be high with the use of printed OLEDs (organic light-emitting diodes). Printed OLEDs are currently used to achieve the high-resolution of TV and phone screens, so it is entirely feasible to print OLEDs at the same fine resolution to recreate a high-resolution three-dimensional model of a microscopic object.

The invention's ability to three-dimensionally model an object will have very important applications in life sciences. Cells and cellular components, which are naturally transparent, can easily be imaged and modeled with the invention at very high-resolution. Currently there are similar microscopy technologies that also achieve three-dimensional modeling, including confocal microscopy, which also uses a scanning point of light. However, the cost of these technologies can be prohibitively high. The present invention has the potential to achieve the same resolution and same detailed three dimensional modeling at a much lower cost.

Being able to image a full three-dimensional model of a cell or organism will also be invaluable when paired with fluorescence microscopy techniques. In fluorescent microscopy, certain fluorescent chemical compounds when combined with for example, antibodies, can be utilized as biological probes, to stain specific targets (i.e., cells, organelles, organisms, etc.) being imaged. This technique is powerful for identifying the regions and structures within a cell or organism that have specific properties and chemical compositions.

It is understood that one skilled in the art can apply a different geometric configurations and/or other different arrangements to form alternate embodiments.

8.2 Fluorescence Detection Example

Figure 76:
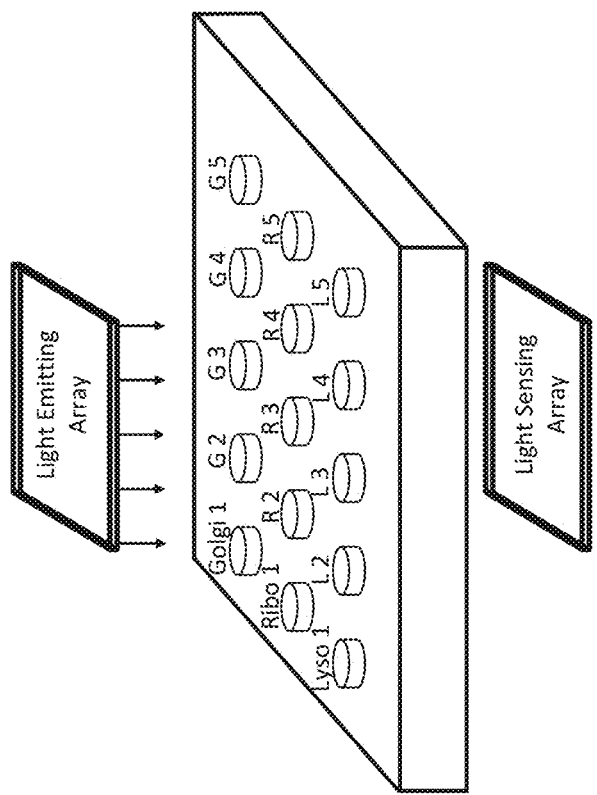
FIG. 76 depicts an example embodiment of a fluorescence detection application with a planar light emitting and light sensing arrangement in an optical tomography system.

One could also use fluorescence techniques to mark specific regions with a cell or organism and then use the invention to image, model, and locate the fluorescing regions. If ultraviolet (UV) excitation is utilized, to block unwanted effects of UV stimulation, a UV filter can also be applied to the invention. FIG. 76 depicts an example embodiment of a fluorescence detection application with a planar light emitting and light sensing arrangement in an optical tomography system. As shown in FIG. 76, varying target-specific fluorescent dyes are applied to samples in the wells of a microplate. Specific organelles are recognized after their emitted fluorescent light is sensed. In this embodiment, a planar tomography configuration is depicted. Cylindrical and other arrangements for each well may also be applied.

It is understood that one skilled in the art can apply a different geometric configurations and/or other different arrangements to form alternate embodiments.

8.3 Cytometry and Flow Cytometry Example

Cytometry refers to the methods that are used to measure various characteristics of a cell, including cell size, current stage of the cell cycle, DNA content, and protein content. This is another very fitting application for the present invention. Cells are naturally transparent, making it very easy to derive a high-resolution three-dimensional model of the cell's interior contents and exterior membrane using our imaging techniques. This model can be used to accurately measure the three-dimensional shape of the cell, and can easily be examined for DNA form and count to determine the stage of the cell cycle. Again, fluorescent markers can be coupled with the invention to identify proteins and other chemicals within the cell. Similar to microscopy, the present invention can achieve microscopic resolution using printable OLEDs.

In one embodiment, the present application can also be applied to flow cytometry as well. Flow cytometry is the method of imaging cells as they move (or flow) in a liquid through the microscope. It is generally used for quickly amassing large amounts of data about a large number of cells. The invention could be adapted to allow for quick imaging of moving objects to obtain high-resolution videostreams of cells.

Figure 77:
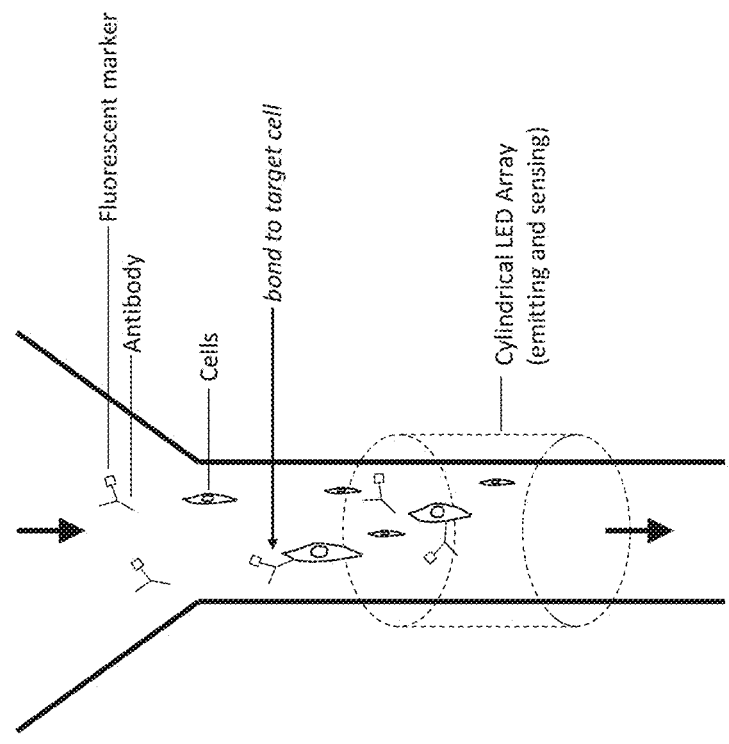
FIG. 77 depicts an example embodiment of a flow cytometry application with a cylindrical light emitting and light sensing arrangement in an optical tomography system.

FIG. 77 depicts an example embodiment of a flow cytometry application with a cylindrical light emitting and light sensing arrangement in an optical tomography system. Antibodies with fluorescent markers attach to specific target cells. Specific targets are recognized after light emitted from the fluorescent marker is sensed. Planar and other arrangements may also be applied.

It is understood that one skilled in the art can apply a different geometric configurations and/or other different arrangements to form alternate embodiments.

8.4 Microplate Example

Figure 78A:
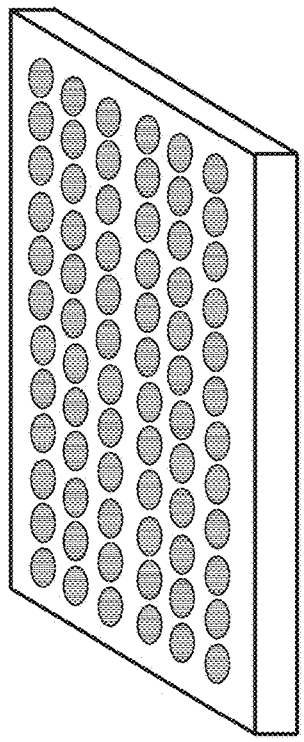
FIG. 78a illustrates an example embodiment of the present invention as a microplate.
Figure 78B:
Figure 80:
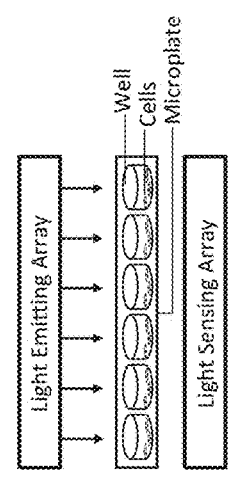
FIG. 80 depicts another example embodiment microplate with a planar light emitting and light sensing arrangement in an optical tomography system.
Figure 79:
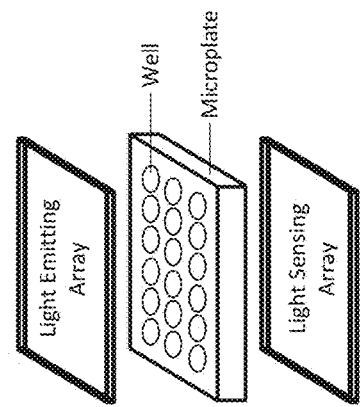
FIG. 79 depicts an example embodiment of a microplate with a planar light emitting and light sensing arrangement in an optical tomography system.

Microplates are also a suitable application for the present application. In one embodiment, cylindrical geometry may be utilized in an embodiment of the present invention with microplates. FIG. 78a illustrates an example embodiment of the present invention as a microplate. FIG. 78b illustrates a side view of FIG. 78a. A cylindrical geometric arrangement of the present invention can be useful as implemented in individual wells of a microplate arrangement commonly used in chemical and life science settings. Such an application can provide a more powerful and detailed approach to imaging the sample within a well. In one embodiment, the light emitting and sensing arrays of the present application can be arranged with planar geometry as depicted in FIG. 78. FIG. 79 depicts an example embodiment of a microplate with a planar light emitting and light sensing arrangement in an optical tomography system. FIG. 80 depicts another example embodiment microplate with a planar light emitting and light sensing arrangement in an optical tomography system.

In another embodiment, a microplate with a planar light emitting and light sensing arrangement can be applied to each well of the microplate in an optical tomography system as depicted in FIG. 81a.

In other embodiments, printing LEDs to form emitting and sensing arrays onto flexible and printable material could leverage the cylindrical geometry in the shape and scale of microplates. For example, FIG. 81b depicts an example embodiment of a microplate with a cylindrical light emitting and light sensing arrangement applied to each well of the microplate in an optical tomography system. Having a cylindrical arrangement can increase the angles from which the sample is scanned, as illustrated above generally for cylindrical arrangements.

It is understood that one skilled in the art can apply a different geometric configurations and/or other different arrangements to form alternate embodiments.

8.5 Culture Dish and Petri Dish Example

Either cylindrical or planar arrangements of the present application can also be applied to culture or Petri dishes commonly used in lab settings. For example, FIG. 82a depicts an example embodiment of a culture dish with a planar light emitting and light sensing arrangement in an optical tomography system. In yet another embodiment, FIG. 82b depicts an example embodiment of a culture dish with a cylindrical light emitting and light sensing arrangement in an optical tomography system.

It is understood that one skilled in the art can apply a different geometric configurations and/or other different arrangements to form alternate embodiments.

8.6 Microfluidic Example

Figure 83:
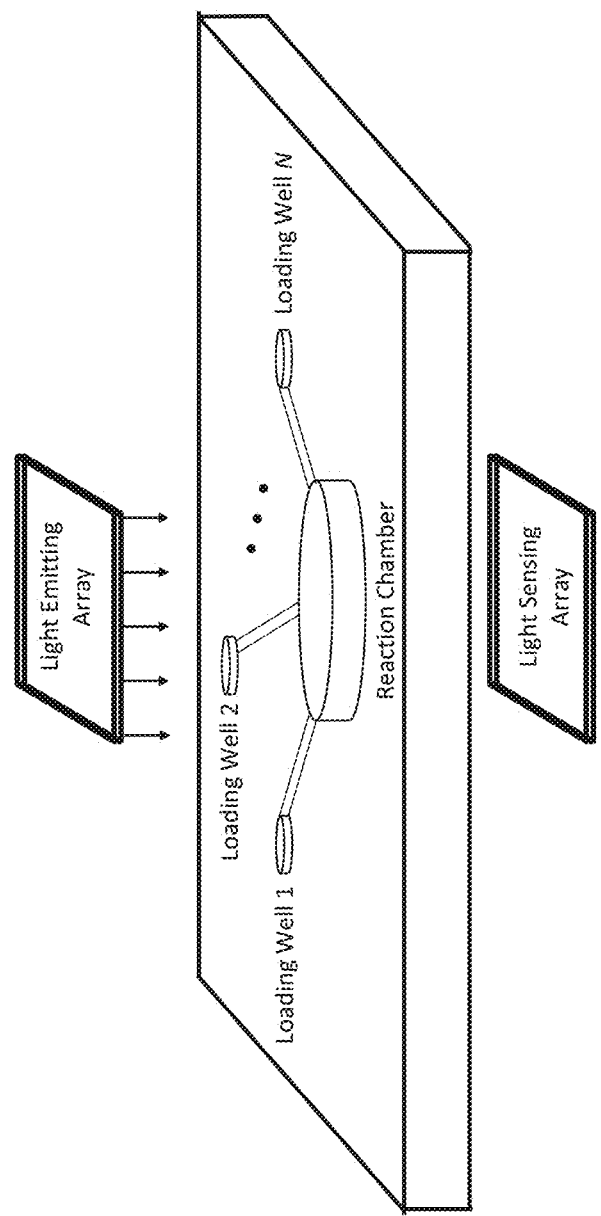

The present application also can be applied to microfluidic applications. As an example, FIG. 83 depicts an example microfluidic plate with a planar light emitting and light sensing arrangement in an optical tomography system. In FIG. 83, a planar geometry arrangement is applied to a reaction chamber on a microfluidic plate, used to detect reaction of substances in the reaction chamber.

It is understood that one skilled in the art can apply a different geometric configurations and/or other different arrangements to form alternate embodiments.

8.7 Incubation Chamber Example

Figure 84:
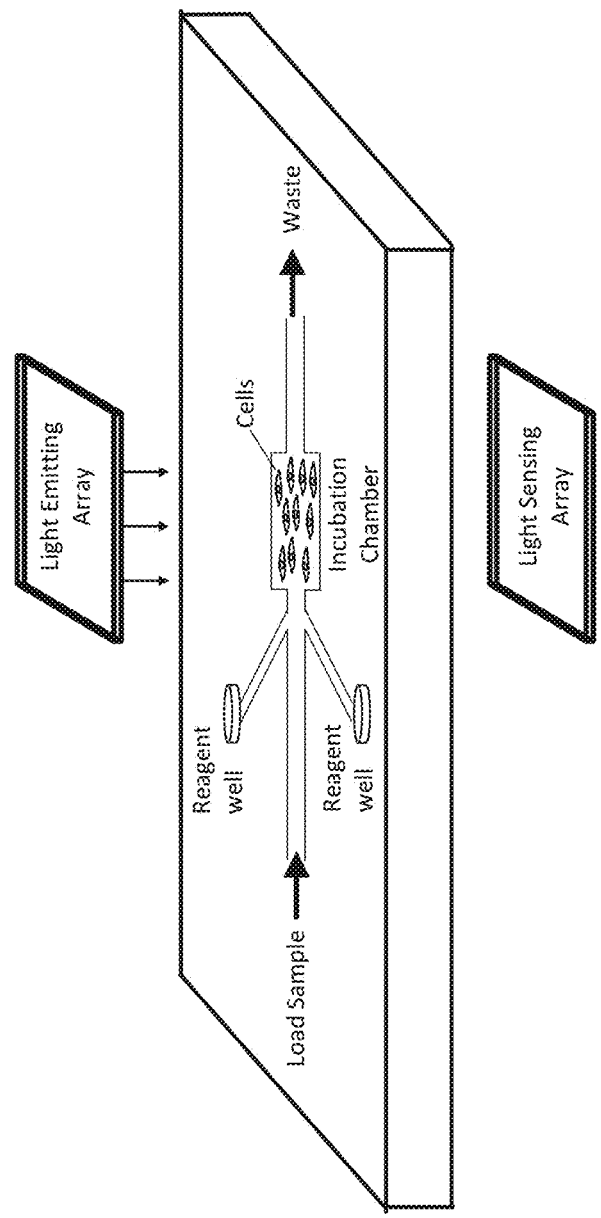

FIG. 84 depicts another example microfluidic plate with a planar light emitting and light sensing arrangement in an optical tomography system. FIG. 84 shows how the optical tomography system of the present application is used to scan the change in culture in a microfluidic incubation chamber. Although a planar configuration is applied to the microfluidic plate, other geometric arrangements can also be implemented.

In yet another embodiment, the present application can also be applied to a microfluidic structure or assembly found on lab-on-a-chip devices.

It is understood that one skilled in the art can apply a different geometric configurations and/or other different arrangements to form alternate embodiments.

8.8 Culture Chamber Example

Figure 85:
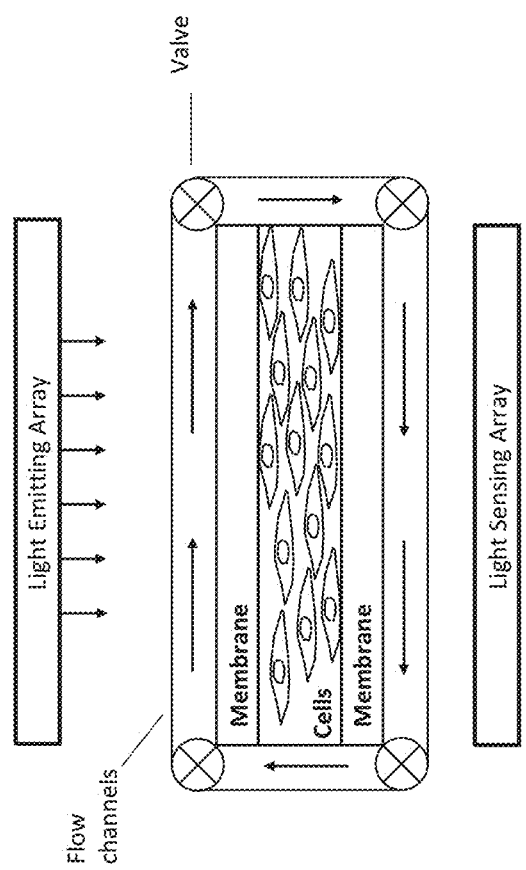

Another biological application of the present application system is shown in FIG. 85, which depicts an example embodiment of a culture chamber, with a planar light emitting and light sensing arrangement in an optical tomography system. FIG. 85 shows the culture chamber enveloped in biological membranes that are selectively-permeable to media that flows through a channel surrounding them, wherein the present application scans the culture chamber. This configuration may embody valves to control media flow.

It is understood that one skilled in the art can apply a different geometric configurations and/or other different arrangements to form alternate embodiments.

Closing

The terms "certain embodiments", "an embodiment", "embodiment", "embodiments", "the embodiment", "the embodiments", "one or more embodiments", "some embodiments", and "one embodiment" mean one or more (but not all) embodiments unless expressly specified otherwise. The terms "including", "comprising", "having" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

While the invention has been described in detail with reference to disclosed embodiments, various modifications within the scope of the invention will be apparent to those of ordinary skill in this technological field. It is to be appreciated that features described with respect to one embodiment typically can be applied to other embodiments.

The invention can be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

In addition, it will be appreciated that the various operations, processes, and methods disclosed herein may be embodied in a machine-readable medium and/or a machine accessible medium compatible with a data processing system (e.g., a computer system), and may be performed in any order (e.g., including using means for achieving the various operations). Accordingly, the specification and drawings are to be regarded in an illustrative rather than a restrictive sense.

Although exemplary embodiments have been provided in detail, various changes, substitutions and alternations could be made thereto without departing from spirit and scope of the disclosed subject matter as defined by the appended claims. Variations described for the embodiments may be realized in any combination desirable for each particular application. Thus particular limitations and embodiment enhancements described herein, which may have particular advantages to a particular application, need not be used for all applications. Also, not all limitations need be implemented in methods, systems, and apparatuses including one or more concepts described with relation to the provided embodiments. Therefore, the invention properly is to be construed with reference to the claims.

We claim:

1. A flow microscope for imaging objects in fluid flows, the flow microscope comprising:
   a fluid conduit comprising a port on each end of a thin flat transparent fluid transport region, the transparent fluid transport region comprising two parallel flat sides;
   a planar illumination surface in contact with one of the flat sides of the transparent fluid transport region; and
   a planar image sensing surface in contact with the other of the flat sides of the transparent fluid transport region, the planar image sensing surface receiving light fields from the planar image illumination, surface and responsively creating electrical image signals;
   wherein light from the planar illumination surface travels into the transparent fluid transport region, producing a resulting light field affected by the fluid and any objects in the fluid,
   wherein the resulting light field is presented to the planar image sensing surface, and
   wherein the planar image sensing surface creates electrical image signals responsive to the resulting light field.

2. The flow microscope of claim 1 wherein the planar illumination surface is electrically powered.

3. The flow microscope of claim 1 wherein the planar illumination surface comprises an array of light-emitting elements.

4. The flow microscope of claim 1 wherein the planar illumination surface comprises an array of light-emitting diodes (LEDs).

5. The flow microscope of claim 1 wherein the planar illumination surface comprises an array of organic LEDs.

6. The flow microscope of claim 1 wherein the planar illumination surface comprises an array of organic LEDs (OLETs).

7. The flow microscope of claim 3 wherein a light-emitting element in the array of light-emitting elements also serves as a light sensor.

8. The flow microscope of claim 7 wherein the array of light-emitting elements also serves as an image sensor.

9. The flow microscope of claim 1 wherein the light-emitting elements in the array of light-emitting elements are illuminated sequentially.

10. The flow microscope of claim 9 wherein the sequential illumination of the light-emitting elements in the array of light-emitting elements is used m image formation.

11. The flow microscope of claim 10 wherein the image formation produces a fully-formed image output.

12. The flow microscope of claim 10 wherein the image formation produces a partially-formed image output.

13. The flow microscope of claim 12 wherein the partially-formed image output is subsequently processed by a processor to produce a fully-formed image output.

14. The flow microscope of claim 10 wherein the image formation produces an output that can be used in optical tomography.

15. The flow microscope of claim 1 further comprising at least one valve.

16. The flow microscope of claim 1 further comprising at least one pump.

17. The flow microscope of claim 16 wherein the pump can also be used to generate electrical power.

18. The flow microscope of claim 16 wherein the pump can also be used to measure the rate of fluid flow through the flow microscope.

19. The flow microscope of claim 1 further comprising power management electronics.

20. The flow microscope of claim 1 further comprising at least one additional sensor.

* * * * *

UNITED STATES PATENT AND TRADEMARK OFFICE
CERTIFICATE OF CORRECTION

PATENT NO. : 9,594,239 B1
APPLICATION NO. : 13/963917
DATED : March 14, 2017
INVENTOR(S) : Lester F. Ludwig et al.

It is certified that error appears in the above-identified patent and that said Letters Patent is hereby corrected as shown below:

On the Title Page

Item (71) Applicant:
Change "Lester F. Ludwig, Belmont CA" to --Lester F. Ludwig, San Antonio, TX--.

Item (72) Inventors:
Change "Lester F. Ludwig, Belmont CA" to --Lester F. Ludwig, San Antonio, TX--.

Signed and Sealed this
Sixteenth Day of May, 2017

Michelle K. Lee
*Director of the United States Patent and Trademark Office*